(12) United States Patent
Segal et al.

(10) Patent No.: US 7,390,884 B2
(45) Date of Patent: Jun. 24, 2008

(54) LYMPHOID CHEMOKINES IN THE DIAGNOSIS, MONITORING AND TREATMENT OF INFLAMMATORY DISEASE

(75) Inventors: Benjamin M. Segal, Rochester, NY (US); Ludmila Bagaeva, Fairport, NY (US)

(73) Assignee: University of Rochester, Rochester, NY (US)

( * ) Notice: Subject to any disclaimer, the term of this patent is extended or adjusted under 35 U.S.C. 154(b) by 174 days.

(21) Appl. No.: 11/119,333

(22) Filed: Apr. 29, 2005

(65) Prior Publication Data
US 2006/0286556 A1 Dec. 21, 2006

Related U.S. Application Data

(60) Provisional application No. 60/566,337, filed on Apr. 29, 2004.

(51) Int. Cl.
*C07K 16/00* (2006.01)
*A61K 39/395* (2006.01)
(52) U.S. Cl. .................................. 530/387.1; 424/130.1
(58) Field of Classification Search ........................ None
See application file for complete search history.

(56) References Cited

U.S. PATENT DOCUMENTS

| | | | |
|---|---|---|---|
| 5,633,149 | A | 5/1997 | Guegler et al. |
| 5,844,084 | A | 12/1998 | Guegler et al. |
| 6,071,701 | A | 6/2000 | Guegler et al. |
| 6,110,695 | A | 8/2000 | Gunn et al. |
| 6,692,920 | B1 | 2/2004 | Guegler et al. |
| 6,852,508 | B1 | 2/2005 | Herrmann et al. |
| 2002/0111290 | A1 | 8/2002 | Homey et al. |
| 2003/0017979 | A1 | 1/2003 | Mack et al. |
| 2003/0026802 | A1* | 2/2003 | Markovitz et al. ....... 424/144.1 |
| 2003/0027136 | A1 | 2/2003 | Goronzy et al. |
| 2003/0124628 | A1 | 7/2003 | Burns et al. |
| 2003/0186889 | A1 | 10/2003 | Forsmann et al. |
| 2004/0018563 | A1 | 1/2004 | Burns et al. |
| 2004/0170628 | A1* | 9/2004 | Lillard et al. ............ 424/145.1 |
| 2004/0191255 | A1 | 9/2004 | Lillard et al. |
| 2004/0214864 | A1 | 10/2004 | Cage et al. |

FOREIGN PATENT DOCUMENTS

| | | |
|---|---|---|
| WO | WO 96/17868 | 6/1996 |
| WO | WO 96/39522 | 12/1996 |
| WO | WO 98/11226 | 3/1998 |
| WO | WO 2004/039956 | 5/2004 |

OTHER PUBLICATIONS

Ajuebor et al., Chemokines as novel therapeutic targets in inflammatory diseases, 2002, Biochemical Pharmacology, vol. 63, pp. 1191-1196.*

Al-Mughales et al., The chemoattractant activity of rheumatoid synovial fluid for human lymphocytes is due to multiple cytokines, 1996, Clinical Experimental Immunology, vol. 106, pp. 230-236.*

Smith et al., Expression of B-cell-attracting chemokine 1 (CXCL 13) by malignant lymphocytes and vascular endothelium in primary central nervous system lymphoma, 2003, BLOOD, vol. 101, No. 3, pp. 815-821.*

Loetscher et al., Homing chemokines in rheumatoid arthritis, 2002, Arthritis Research, vol. 4, pp. 233-236.*

NINDS-NIH, NINDS Multiple Sclerosis Information page, Last Updated Apr. 16, 2007, [Retrived Jul. 23, 2007], Retrived from the internet:<URL: http://www.ninds.nih.gov/disorders/multiple_sclerosis/multiple_sclerosis.htm?css=print>.*

Gold et al., Understanding pathogenesis and therapy of multiple sclerosis via animal models: 70 years of merits and culprits in experimental autoimmune encephalomyelitis research, 2006, Brain: a journal of neurology, vol. 129, Part 8, pp. 1953-1971.*

Friese et al., The value of animal models for drug development in multiple sclerosis, 2006, Brain: a journal of Neurology, vol. 129, Part 8, pp. 1940-1952.*

Bagaeva, et al., "Lymphoid chemokines in central nervous system (CNS) autoimmunity" Poster Presentation Aug. 26, 2003.

Bagaeva, et al., "CXCL13 in the central nervous system (CNS) during experimental autoimmune encephalomyelitis" Poster Presentation Apr. 21, 2004.

Aloisi, et al., *J. Immunol.* 164:1705-1712 (2000).
Alt, et al., *Euro. J. Immunol.* 32:2133-2144 (2002).
Ando, et al., *Cell Immunol.* 124:132-143 (1989).
Ansel, et al., *J. Exp. Med.* 190:1123-1134 (1999).
Ansel, et al., *Nature* 406:309-314 (2000).
Ansel, et al., *Immunity* 16:67-76 (2002).
Bagaeva, et al., *J. Neuroimmunol.* 137:109-116 (2003).
Baranzini, et al., *J. Immunol.* 163:5133-5144 (1999).
Baron, et al., *J. Exp. Med.* 177:57-68 (1993).
Bauer, et al., *Glia* 15:437-446 (1995).
Bauer, et al., *Histochemical Journal* 28:83-97 (1996).
Becher, et al., *J. Clin. Invest.* 110:493-497 (2002).
Biber, et al., *Glia* 34:121-133 (2001).

(Continued)

*Primary Examiner*—Bruce Campell
*Assistant Examiner*—Benjamin P. Blumel
(74) *Attorney, Agent, or Firm*—Fish & Richardson P.C.

(57) ABSTRACT

Experimental autoimmune encephalomyelitis (EAE) is a Th1-mediated autoimmune disease of the central nervous system that is widely used as an animal model of multiple sclerosis (MS). In this study it was demonstrate that CXCL13, a chemokine involved in the development of secondary lymphoid tissues, is expressed in CD11c+ myeloid cells that accumulate in EAE lesions. Blockade or deficiency of CXCL13 ameliorates clinical EAE, both during acute and relapsing stages. CXCL13 deficiency did not inhibit the priming or differentiation of autoimmune effector T-cells in the periphery, but appeared to exert its effects during the effector phase of pathogenesis. These findings indicate that reagents that antagonize or inhibit CXCL13 are useful for the treatment of neuroinflammatory diseases such as MS.

6 Claims, 15 Drawing Sheets

OTHER PUBLICATIONS

Bielekova, et al., *Nat. Med.* 6:1167-1175 (2000).
Boven, et al., *Clin. Exp. Immunol.* 122:257-263 (2000).
Campbell, et al., *J. Cell Biol.* 141:1053-1059 (1998).
Cannella, et al., *Exp. Med.* 172:5121-1524 (1990).
Cella, *J. Exp. Med.* 184:747-752 (1996).
Chen, et al., *J. Immunol.* 168(3):1009-1017 (2002).
Colombo, et al., *J. Immunol.* 164:2782-2789 (2000).
Columba-Cabezas, et al., *Brain Pathology* 12:38-51 (2003).
Correale, et al., *J. of Neurology* 249:375-389 (2002).
Cross, et al., *Lab. Invest.* 63:162-170 (1990).
Cross, et al., *J. Neuroimmunol.* 112:1-14 (2001).
Cyster, *Science* 286:2098-2102 (1999).
Eugster, et al., *Eur. J. Immunol.* 29:626-632 (1999).
Fan, et al., *J. Immunol.* 164(8):3955-3959 (2000).
Fife, et al., *J. Neurosci. Res.* 66:705-714 (2001).
Finke, et al., *Immunity* 17:363-373 (2002).
Fischer and Reichmann, *J. Immunol.* 166(4):2717-2726 (2001).
Forster, et al., *Cell* 87:1037-0147 (1996).
Genain, et al., *Journal of Clinical Investigation* 96:2966-2974 (1995).
Gerritse, et al., *J. Neuroimmunol.* 49:153-159 (1994).
Gommerman, et al., *J. Clin. Invest.* 112:755-767 (2003).
Gunn, et al., *Nature* 391(6669):799-803 (1998).
Gunn, et al., *J. Exp. Med.* 189:451-460 (1999).
Hikino, et al., *Trans. Proc.* 32:2458-2459 (2000).
Hjelmstrom, et al., *Am. J. Path.* 156:1133-1138 (2000).
Iglesias, et al., *Glia* 36:220-234 (2001).
Ishikawa, et al., *J. Exp. Med.* 193:1391-1402 (2001).
Itakura, et al., *J. Immunol.* 166:2071-2079 (2001).
Kanwar, et al., *J. Neuroimmunol.* 103:146-152 (2000).
Karpus and Ransohoff, *Immunology* 161:2667-2671 (1998).
Kawakami, et al., *J. Exp. Med.* 199:185-197 (2004).
Kim, et al., *J. Exp. Med.* 193:1373-1381 (2001).
Korner, et al., *J. Exp. Med.* 186:1585-1590 (1997).
Legler, et al., *J. Exp. Med.* 187:665-660 (1998).
Luther, *PNAS* 97:1269412699 (2000).
Luther, et al., *Immunity* 12:471-481 (2000).
Luther, et al., *J. Immunol.* 169:424-433 (2002).
Luther, et al., *J. Exp. Med.* 197:1191-1198 (2003).
Lyons, et al., *European J. Immunol.* 29:3432-3439 (1999).
Lyons, et al., *Eur. J. Immunol.* 32:1905-1913 (2002).
Magliozzi, et al., *Journal of Neuroimmunology* 148:11-23 (2004).
Marusic, et al., *Neuroscience Lett.* 332:185-189 (2002).
Mazzucchelli, et al., *J. Clin. Inv.* 204:R49-R54 (1999).
McQualter, et al., *J. Exp. Med.* 194(7):873-882 (2001).
Mori, et al., *J. Exp. Med.* 193:207-218 (2001).
Moser and Loetscher, *Nature Immunology* 2(2):123-128 (2001).
Nakano and Gunn, *J. Immunol.* 166(1):361-369 (2001).
Ngo, et al., *J. Exp. Med.* 189:403-412 (1999).
Olschowka, et al., *Mol. Therapy* 7(2):218-227 (2003).
Oppmann, et al., *Immunity* 13:715-725 (2000).
Pashenkov, et al., *J. Neuroimmunol.* 135:154-160 (2003).
Pashenkov, et al., *Brain Pathology* 13:23-33 (2003).
Paterson and Swanborg, "Demyelinating diseases of the central and peripheral nervous systems" In: *Immunological Diseases* ; Samter, ed., pp. 1877-1916, Little, Brown and Company, Boston, MA (1998).
Prineas and Wright, *Lab. Invest.* 38:409-421 (1978).
Prineas, *Science* 203:1123-1125 (1989).
Raine, et al., *Lab. Invest.* 43:150-157 (1980).
Raine, et al., *Lab. Invest.* 51:534-546 (1984).
Raine, et al., *Clinical Immunology & Immunopathology* 57:173-187 (1990).
Raine, et al., *Lab. Invest.* 63:476-489 (1990).
Salomonsson, et al., *Scan. J. Immunol.* 55:336-342 (2002).
Santambrogio, et al., *PNAS* 98:6295-6300 (2001).
Segal and Shevach, *J. Exp. Med.* 184:771-775 (1996).
Segal, et al., *J. Immunol.* 164:5683-5688 (2000).
Segal, et al., *J. Exp. Med.* 187:537-546 (1998).
Selmaj, et al., *Neuroimmunol.* 56:135-141 (1995).
Selmaj, et al., *J. Clin. Invest.* 87:949-954 (1991).
Selmaj, et al., *J. Immunol.* 28:2035-2044 (1998).
Serafini, et al., *American Journal of Pathology* 157:1991-2002 (2000).
Shi, et al., *J. Immunol.* 166:650-655 (2001).
Shu, et al., *Eur. J. Immunol.* 25:1125-1128 (1995).
Simpson, et al., *J. Neuroimmunol.* 84:238-249 (1998).
Skundric, et al., *Lab. Invest.* 71:671-679 (1994).
Skundric, et al., *J. Neuroimmunol.* 46:113-121 (1993).
Spahn, et al., *Eur. J. Immunol.* 29(12):4060-4071 (1999).
Suen, et al., *J. Exp. Med.* 186:1233-1240 (1997).
Suter, et al., *Eur. J. Immunol.* 30:794-802 (2000).
Takemura, et al., *J. Immunol.* 167(2):10721080 (2001).
Theise, et al., *Exp. Hematol.* 30:1333-1338 (2002).
Traugott, et al., *J. Neuroimmunol.* 4:201-221 (1983).
Traugott, et al., *Science* 214:1251-1253 (1981).
Tumanov, et al., *Immunity* 17:239-250 (2002).
Ulvestad, et al., *J. Leukoc. Biol.* 56:732-740 (1994).
Vanderlugt, et al., *J. Immunol.* 164:670-678 (2000).
Vissers, et al., *Eur. J. Immunol.* 31:1544-1549 (2001).
Voskuhl, et al., *Autoimmunity* 15:137-143 (1993).
Wong, et al., *Cell. Immunol.* 123:445-455 (1989).
Yoneyama, et al., *J. Exp. Med.* 193:35-49 (2001).
Bachmann and Kopf, "On the role of the innate immunity in autoimmune disease" *Exp. Med.* 193(12):F47-50 (2001).
Corcione et al., "Recapitulation of B-cell differentiation in the central nervous system of patients with multiple sclerosis" *PNAS* 101:11064-11069 (Jul. 2004).
Haringman et al., "Chemokines in joint disease: the key to inflammation?" *Ann. Rheum. Dis.* 63:1186-94 (2003).
Houshmand and Zlotnik, "Therapeutic applications in the chemokine superfamily" *Curr. Opinion Chemical Bio.* 7:457-60, (2003).
Jenh et al., "Human B cell attracting chemokine 1 (BCA-1; CXCL13) is an agonist for the human CXCR3 receptor" *Cytokine* 15:113-121 (2001).
Schiffer et al., "Short term administration of costimulatory blockade and cyclophosphamide induces remission of systemic lupus erythematosus nephritis in NZB/W $F_1$ mice by a mechanism downstream of renal immune complex deposition" *J. Immunol.* 171(1):489-97 (2003).
Serafini et al., "Detection of B-cell follicles with germinal centers in the meninges of patients with secondary progressive multiple sclerosis" *Brain Pathol.* 14(2):164-74 (2004).
Zheng et al., "CXCL13 neutralization reduces the severity of collagen-induced arthritis" *Arthr. Rheum.* 52:620-6 (Feb. 2005).

* cited by examiner

A

B

LYMPHOID CHEMOKINES IN THE DIAGNOSIS, MONITORING AND TREATMENT OF INFLAMMATORY DISEASE

This application claims benefit of U.S. Provisional Application No. 60/566,337, filed on Apr. 29, 2004, which is incorporated herein by reference in its entirety.

This invention was made with government support under National Institutes of Health Grant NS41562. The government has certain rights in the invention.

BACKGROUND OF THE INVENTION

1. The majority of autoimmune diseases are chronic conditions, characterized by persistent or relapsing inflammation in the target organ. This is certainly true of multiple sclerosis (MS), an inflammatory disease of central nervous system (CNS) white matter, which generally presents with recurrent episodes of neurological dysfunction followed by a secondary stage of gradually worsening disability. Experimental autoimmune encephalomyelitis (EAE), an animal model with strong pathological similarities to MS, also follows a relapsing, progressive clinical course (Raine, C. S., et al. 1984. *Laboratory Investigation* 51:534-546).

2. In the human disease multiple sclerosis (MS) and the animal model, experimental autoimmune encephalomyelitis (EAE), chronic or relapsing inflammation in the central nervous system (CNS) results in destruction of the myelin sheath. EAE is induced in naïve mice by the adoptive transfer of $CD4^+$ T-cells specific for myelin proteins (Raine, C. S., et al. 1984. *Laboratory Investigation* 51:534-546). Once these effector cells cross the blood-brain-barrier, they activate resident microglia and recruit peripheral leukocytes to the CNS (Bauer, J., et al. 1995. *Glia* 15:437). Perivascular infiltrates are subsequently formed within the white matter and evolve into lymphoid-myeloid aggregates over time.

3. In acute lesions, myeloid cells dominate the inflammatory infiltrate (Bauer, J., et al. 1995. *Glia* 15:437). T-cells become more numerous in chronic lesions and are sometimes found in association with dendritic-like (dendriform) cells. B cells and plasma cells are also frequently present, and tend to localize in regions distinct from those containing T-cells (Raine, C. S., et al. 1984. *Laboratory Investigation* 51:534-546, Paterson, P. Y., and Swanborg, R. H. 1988. In: *Immunological Diseases* (ed. Samter, M.), Traugott, U., et al. 1983. *Journal of Neuroimmunology* 4:201-221). Even lymphatic capillaries have been demonstrated in the CNS tissues of patients with long standing MS (Prineas, J. W., and Wright, R. G. 1978. *Laboratory Investigation* 38:409-421). The structured appearance and cellular composition of these chronic CNS lesions are reminiscent of secondary lymphoid tissues. Similarly, in EAE white matter infiltrates exhibit features normally associated with lymph nodes and spleen including perivascular T-cell cuffs (approximating periarterial sheaths in the spleen), lymphoid-myeloid aggregates, and blood vessels with characteristics of high endothelial venules (HEV).

4. Several features of chronic inflammatory infiltrates in autoimmune lesions parallel the architectural characteristics of secondary lymphoid tissues. For example, T and B cells tend to segregate into distinct areas of chronic MS plaques, similar to the T-cell-and B cell-rich areas of lymph node and spleen (Raine, C. S., et al. 1984. *Laboratory Investigation* 51:534-546, Paterson, P. Y., and Swanborg, R. H. 1988. In: *Immunological Diseases* (ed. Samter, M.)-3). Lymphatic-like capillaries have been identified in long-standing MS lesions (Prineas, J. W., and Wright, R. G. 1978. *Laboratory Investigation* 38:409-421). Furthermore, myeloid dendritic cells, a critical class of antigen presenting cells (APC) that serve to activate T-cells in peripheral lymphoid organs, have recently been detected in MS and EAE lesions (Ulvestad, E., et al. 1994. *J Leukoc Biol.* 56:732-40, Fischer, H. G. and Reichmann, G. 2001. *J Immunol.* 166:2717, (Serafini, B., et al. 2000. *American Journal of Pathology* 157:1991-2002). Interestingly, microglia acquire dendritic-like cell characteristics following stimulation with GM-CSF in vitro, raising the possibility that dendritic cells differentiate from CNS glial cells in vivo (Fischer, H. G. and Reichmann, G. 2001. *J Immunol.* 166:2717, Santambrogio, L., et al. 2001. *PNAS* 98:6295, Aloisi, F., et al. 2000. *J. Immunol.* 164:1705). Although these studies suggest that autoimmune infiltrates evolve using similar pathways to those that guide the development and organization of secondary lymphoid tissues, needed in the art are specific agents that modulate relevant pathways involved in autoimmune disease.

5. CXCL13, also known as B-lymphocyte chemoattractant (BLC), B-cell-attracting chemokine 1 (BCA1), and Angie-2, is a protein of about 88 amino acids in the group of CXC-Chemokines. The receptor for CXCL13 is CXCR5 (also known as BLR-1 and MDR15), although CXCR3 has also been identified as a receptor.

SUMMARY OF THE INVENTION

6. In accordance with the purposes of this invention, as embodied and broadly described herein, this invention, in one aspect, relates to an methods of screening for agents that inhibit T-cell mediated inflammatory responses. Also provided herein are methods of treating an inflammatory condition comprising administering an agent identified by the disclosed screening methods.

7. Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

8. The accompanying drawings, which are incorporated in and constitute a part of this specification, illustrate several embodiments of the invention and together with the description, serve to explain the principles of the invention.

9. FIG. 1(*a*) shows the results of an experiment in which B10.PL mice (n=5) were immunized with $MBP_{Ac1-11}$ in CFA and sacrificed five weeks later during clinical EAE (one mouse remained asymptomatic). Spinal cords were harvested for RNA extraction and RT-PCR analysis. Cords from naïve mice (n=4) were used as negative controls. FIG. 1 (*b*) shows similar results using an adoptive transfer paradigm. In the experiment shown, draining LN cells from $PLP_{139-151}$/IFA-sensitized SJL mice were injected into naïve syngeneic recipients ($50 \times 10^6$ i.p.) following in vitro challenge with antigen in the presence (left panel) or absence (right panel) of recombinant murine IL-12. Mice were sacrificed between days 10 and 12 post-transfer for RT-PCR analysis of whole spinal cord specimens. FIG. 1(*c*) shows that CXCL13 and CCL19 proteins are expressed in spinal cord tissue from SJL mice with adoptively transferred EAE but not in spinal cords from their naïve counterparts (n=10/group). Spinal cord tissues pooled from each group were analyzed for CXCL13, CCL19 and CCL21 protein expression by Western blot. Spleen extracts and recombinant murine chemokines were used as positive controls. All experiments were repeated at least two times with similar results.

11. FIG. 3(*a*) shows FACS analysis of spinal cord lymphoid cells (gated based on forward and side scatter characteristics) isolated from $PLP_{139-151}$/CFA-sensitized SJL mice following the first episode of clinical EAE. FIG. 3(*b*) shows CNS-infiltrating CD4+ CXCR5+ and CXCR5− cells that were triple stained against a panel of activation markers to generate the histograms. Positive gates were determined based upon background staining with isotype matched control antibodies. These experiments were performed multiple times with similar results.

12. In FIG. 4(*b*), spinal cord MNCs from C57BL/6 mice with $MOG_{35-55}$-induced EAE or naïve controls were analyzed by FACS and RT-PCR as described above. In FIG. 4(*c*), spinal cord MNCs from C57BL/6 mice with EAE were separated based on expression of the dendritic cell marker, CD11c, using magnetic beads. Semiquantitative RT-PCR and southern blot hybridization were performed on unfractioned, CD11c-depleted and CD11c-enriched fractions as shown. Relative mRNA levels were determined by phosphorimaging and densitometry.

13. FIG. 5(C) shows the clinical courses of SJL mice that were injected i.p. with $PLP_{139-151}$-reactive LN cells on day 0 and either goat anti-mouse CXCL13 antibody (0.2 mg, R&D), control goat IgG (0.2 mg) or PBS on days 3, 6, and 10 (n=5/group). Statistical differences were observed between the anti-CXCL13 treated group and each of the control groups (P<0.05, Student-Newman-Keuls method) but not between the two control groups. FIG. 5D shows that EAE was induced in C57BL/6 WT and CXCL13−/− mice by adoptive transfer of purified CD4+ T-cells from primed WT donors. Clinical scores reflect viable animals only; mice that died of EAE (3/5 in the WT group; 2/7 in the CXCL13−/− group) were given a score of 5 on the day of death. The difference in clinical scores between groups is statistically significant (P<0.0001). The experiment was performed 3 times with similar results.

16. FIG. 8(A) shows a frozen section of a spinal cord from a representative SJL mouse with EAE (clinical score 3). The section was stained with FITC conjugated anti-CD4 and PE-conjugated anti-CD11c and analyzed on an MRC-600 confocal laser microscope system The lower panel is of the same section photographed using a filter that screens out the FITC-signal in order to highlight the staining for dendritic-like cells. FIG. 8(B) shows a perivascular infiltrate in the spinal cord of a C57BL/6 mouse with EAE (score 3) that was visualized by whole mount technique. In this image CD4+ cells were stained with an APC conjugated antibody, dendritic-like cells with PE-conjugated anti-CD11c and inflamed blood vessels with FITC-conjugated anti-P-selectin. Spinal cords from naïve mice failed to stain with any of the antibodies. Background from isotype control antibodies was negligible.

20. FIG. 12A shows C57BL/6 WT and CXCL13−/− mice that were immunized with $MOG_{35-55}$/CFA. Spleens were harvested to assess antigen-specific proliferation (day 19 post immunization) and cytokine production (data from individual mice; days 24-27). The ELISPOT data show antigen-specific responses (50 µg/ml of MOG). The results are representative of two or more experiments. (* $P<0.05$). FIG. 12 B shows splenocytes from MOG/CFA primed CXCL13−/− or WT mice were stimulated in vitro with MOG and IL-12, and injected into WT recipients. The difference in clinical scores between groups is statistically significant ($P<0.0001$). The experiment shown was performed three times with similar results.

21. FIG. 13A shows that the absolute number of infiltrating CD4+ T-cells/cord was calculated by multiplying their percentage within the inflammatory infiltrate (determined using FACS) by the total number of MNCs per cord. Results shown represent the mean of two representative experiments. FIG. 13B shows dot plots that were generated using the lymphoid scatter gate. All experiments were performed three or more times with similar results.

22. FIG. 14A shows dot plots that were generated using a wide scatter gate to include all viable cells. FIG. 14B shows the absolute numbers for $CD45^{hi}$ $CD11b^{hi}$ cells in the CNS infiltrate calculated as described in the legend to FIG. 13. The numbers are derived from the representative experiments shown in (A). These experiments were repeated three times with similar results.

DETAILED DESCRIPTION

Figure 1:
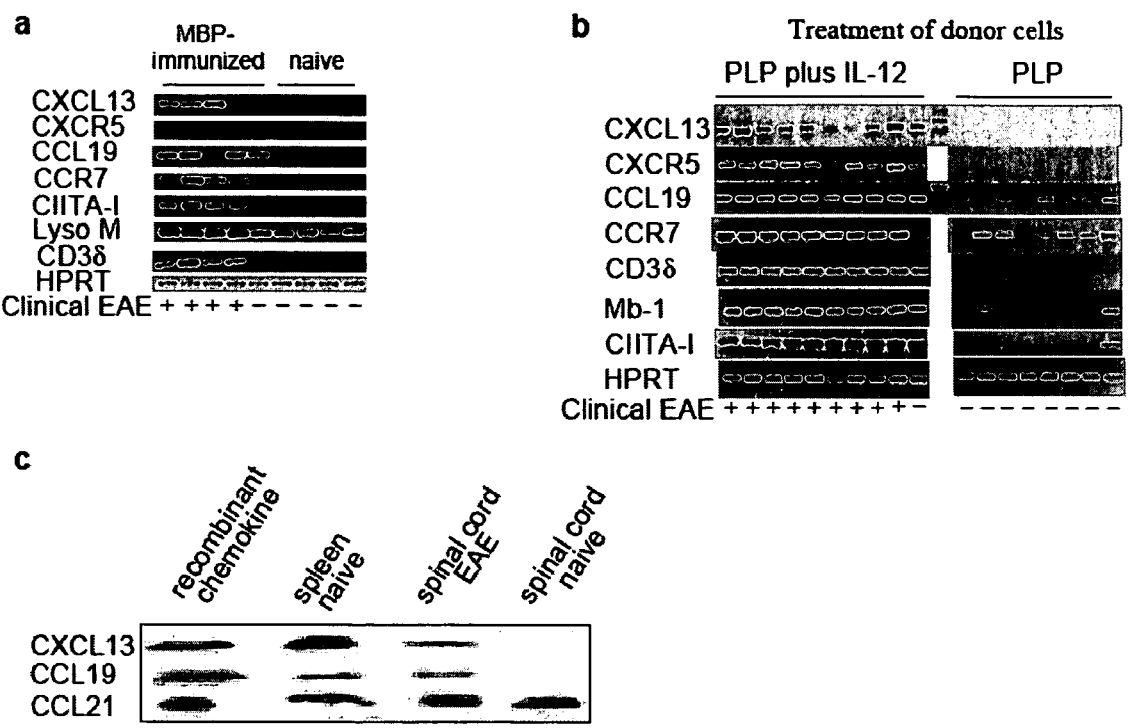
FIG. 1 shows that CXCL13 and CCL19 are expressed in the CNS of mice with EAE.

24. The present invention may be understood more readily by reference to the following detailed description of preferred embodiments of the invention and the Examples included therein and to the Figures and their previous and following description.

25. Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

26. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

27. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

28. In this specification and in the claims which follow, reference will be made to a number of terms which shall be defined to have the following meanings:

29. "Optional" or "optionally" means that the subsequently described event or circumstance may or may not occur, and that the description includes instances where said event or circumstance occurs and instances where it does not.

30. The term "subject" is used throughout this disclosure to refer to any organism, tissue, or cell being contacted with the agent or treated with the agent. Such subjects include but are not limited to tissue culture cells, mammals, mice, rats, guinea pigs, dogs, pigs, rabbits, sheep, monkeys, chimpanzees, and humans. It is understood and herein contemplated that the disclosed methods of screening include methods of screening, wherein the subject is a mammal. It is also understood that the disclosed methods of treatment include methods of treatment wherein the subject is a mammal. In one embodiment, the subject is a mammal, for whom diagnosis or therapy is desired. In a specific embodiment, the subject is a human for whom diagnosis or therapy is desired.

31. Herein "inhibition," "inhibits," or "inhibiting" refer to the modulation of a cell, interaction, or action in a reducing manner. It is understood that "inhibition" can refer to any decrease in an action or activity of a cell, or as cellular interaction, or molecular interaction interaction, or action including but not limited to the complete ablation and/or prevention of the action, interaction, or activity. For example, inhibition of T-cell mediated inflammatory responses includes decreasing the degree of the inflammatory response by 5%, 10%, 20%, 30%, 40%, 50%, 60%, 70%, 80%, 90%, or 100% or any point in between, compared to an untreated or control subject as determined by any suitable measurement technique or assay disclosed herein or known in the art. Furthermore, the untreated or control subject can be a separate subject measured at the same or a different time as the treated subject, or the treated subject measured prior to treatment, with the pre-treatment values compared to the post-treatment values to determine the level of reduction. Thus, for example an agent that inhibits a T-cell mediated inflammatory response refers to any agent that can decrease T-cell mediated inflammation by as little as 5% of the total inflammation as well as agents that completely ablate the inflammatory response. Any of these treatment types or types of patients may also be excluded.

32. "Agent" refers to any composition including but not limited to antibodies, siRNA, chemical compositions, cytokines, chemokines, or small molecules. The agents of the invention can be prepared as pharmaceutical compositions and combined with adjuvants to increase their effect. For example, the agent can comprise an antibody that blocks the action of CXCL13. Thus also disclosed are methods, wherein the agent to be screened is a neutralizing antibody to CXCL13. Similarly, the agents may also comprise antibodies to other chemokines or chemokine receptors. Therefore, one embodiment of the disclosed methods are methods, wherein the agent is an antibody to CXCR5 and wherein the antibody blocks CXCL13 binding without causing signaling through CXCR5. It is understood that the disclosed agents can comprise both membrane bound and soluble forms of chemokines, cytokines, ligands, and their receptors. Thus, for example, specifically contemplated are methods, wherein the agent is a soluble form of CXCR5 or a derivative or analog thereof. In another embodiment, the agent may be an analog or derivative of CXCL13 (e.g., a dominant negative form of CXCL13 or some other form of CXCL13 which is modified from the normal, native form CXCL13) which blocks binding of endogenous CXCL13 to its receptors (e.g., CXCR5 and/or CXCR3), or otherwise interferes with receptor functions which functions include, without limitation, the ability to bind ligand molecules, the ability to interact with other proteins, the ability to generate a "signal" affecting the properties or behaviors of the cell expressing the receptor, or the ability to interact with or affect other cells. Any of these agents may also be excluded. Thus, for example, in one embodiment, the agent of the present invention is not an siRNA, small organic molecule, or macromolecule.

33. The terms "treat," "treatment," or "treating" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. For example, treating an inflammatory condition means reducing the extent or severity of the inflammation. The reduction can mean but is not limited to the complete ablation of inflammation. For example, the reduction can comprise a 5%, 10%, 20%, 30%, 40%, 50%, 60%, 70%, 80%, 90%, or 100% reduction, or any point in between, compared to an untreated or control subject as determined by any suitable measurement technique or assay disclosed herein or known in the art. Furthermore, the untreated or control subject can be a separate subject measured at the same or a different time as the treated subject, or the treated subject measured prior to treatment, with the pre-treatment values compared to the post-treatment values to determine the level of reduction. Any of these treatment types or types of patients may also be excluded.

34. By "specifically binds," it is generally meant that an antibody binds to an epitope via its CDR, and that the binding entails some complementarity between the CDR and the epitope. According to this definition, an antibody is said to "specifically bind" to an epitope when it binds to that epitope, via its CDR more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

Methods of Screening

35. Experimental autoimmune encephalomyelitis (EAE) is an inflammatory demyelinating disease of CNS white matter that frequently follows a relapsing or progressive clinical course. It is widely used as an animal model of multiple sclerosis (MS). Adoptive transfer studies have demonstrated that myelin-reactive CD4+ Th1 cells trigger the disease process in EAE (Ando, D. G., et al. 1989. *Cell Immunol* 124: 132-143). However, non-specific lymphocytes and myeloid cells constitute the majority of cells in established CNS infiltrates and are largely responsible for the end organ damage (demyelination and axonal injury) that results in neurological deficits (Bauer, J., et al. 1996. *Histochemical Journal* 28:83-97, Cross, A. H., et al. 1990. *Lab Invest* 63:162-170, (Raine, C. S., et al. 1990. *Lab Invest* 63:476-489, (Skundric, D. S., et al. 1993. *Journal of Neuroimmunology* 46:113-121). These inflammatory cells are not randomly distributed in the CNS but form discrete perivascular infiltrates in subpial and parenchymal white matter tracts. Throughout the course of disease, myelin-reactive T-cells remain adjacent to blood vessels and are surrounded by macrophages and activated microglia that extend into the parenchyma (Raine, C. S., et al. 1990. *Lab Invest* 63:476-489, (Raine, C. S., et al. 1990. *Clinical Immunology & Immunopathology* 57:173-187). Many laboratories have investigated the role of "pro-inflammatory" chemokines, such as CCL2, CCL3, CCL5 and CXCL10, in attracting circulating leukocytes to acute demyelinating lesions (Fife, B. T., et al. 2001. *J Neurosci Res* 66:705-714, Karpus, W. J., and Ransohoff, R. M. 1998. *Journal of Immunology* 161: 2667-2671).

36. Certain histological features of established MS and EAE lesions are reminiscent of secondary lymphoid tissues. Such features include perivascular T-cell cuffing, clustering of T-cells and dendritic-like cells into lymphoid-myeloid aggregates, and the segregation of B and T-cells into distinct areas within chronic plaques (Cross, A. H., et al. 1990. *Lab Invest* 63:162-170, Traugott, U., et al. 1981. *Science* 214: 1251-1253, Traugott, U., et al. 1983. *Journal of Neuroimmunology* 4:201-221, Raine, C. S., et al. 1980. *Laboratory Investigation* 43:150-157, Raine, C. S., et al. 1984. *Laboratory Investigation* 51:534-546, Prineas, J. W., and Wright, R. G. 1978. *Laboratory Investigation* 38:409-421, Prineas, J. W. 1979. *Science* 203:1123-1125, Pashenkov, M., et al. 2003. *Brain Pathology* 13:23-33, Serafini, B., et al. 2000. *American Journal of Pathology* 157:1991-2002). In a neuropathological survey of demyelinating lesions in SJL mice with relapsing EAE, Raine and colleagues observed "nests of small lymphocytes, large mononuclear cells and plasma cells separated by septa from reticular-like cells giving the tissue a sinusoidal arrangement" (Raine, C. S., et al. 1984. *Laboratory Investigation* 51:534-546). Similarly, Prineas described "clusters of plasma cells together with . . . reticular cells surrounding collagen-free channels containing lymphocyes and macrophages" in plaques in brain specimens from patients with MS (Prineas, J. W. 1979. *Science* 203:1123-1125). Lymphatic-like capillaries were also identified in long standing MS lesions. In both of the cited references parallels were drawn between the organization of the CNS infiltrates and the medullary regions of a lymph node. Analogies have also been made between the vascular elements in inflammatory demyelinating lesions and lymphoid tissues. For example, endothelial cells in inflamed blood vessels of chronic EAE plaques were noted to be enlarged, cuboidal and to bulge into the vessel lumen, evocative of high endothelial venules (HEVs) in LNs (Raine, C. S., et al. 1990. Lab Invest 63:476-489). MAdCAM-1 and MECA-325, adhesion molecules normally restricted to HEV, were detected on CNS blood vessels in mice afflicted with EAE (Raine, C. S., et al. 1990. Clinical Immunology & Immunopathology 57:173-187, Vissers, J. L. M., et al. 2001. Eur. J. Immunol. 31:1544, Luther, S. A., et al. 2000. Immunity 12:471-481). Thus, "lymphoid neogenesis," or the formation of new lymphoid tissues, occurs within the brain and spinal cord during the evolution of EAE and MS.

37. Chemokines play a pivotal role in leukocyte migration. During acute EAE, "inflammatory" chemokines such as RANTES, MIP1α, MIP1β and MCP-1 are expressed in the spinal cord and presumably contribute to the accumulation and activation of mononuclear cells bearing CCR5 and CCR2 receptors (Karpus, W. J. and Ransohoff, R. M. 1998. J. Immunol. 161: 2667). Similarly, RANTES and MIP1α have been detected in active white matter lesions in autopsy specimens from patients with MS (Boven, L. A., et al. 2000. Clin Exp Immunol. 122:257, (Simpson, J. E., et al. 1998. J Neuroimmunol. 84:238).

38. Lymphoid chemokines, including CXCL13 (BLC), CCL19 (ELC), and CCL21 (SLC), are critical for the formation of peripheral lymphoid organs. They guide the migration of leukocyte subsets to B cell and T-cell rich areas (Cyster, J. G. 1999. Science 286:2098-2102, Moser, B., and Loetscher, P. 2001. Nature Immunol. 2:123). CXCL13 is produced by stromal cells in lymphoid follicles and interacts with the CXCR5 receptor, which is expressed on B cells and a subpopulation of T-cells (Gunn, M. D., et al. 1998. Nature. 391: 799, Legler, D. F., et al. 1998. J. Exp. Med. 187:665, Kim, C. H., et al. 2001. J Exp Med. 193:1373-1381). CXCR3 has also been identified as a receptor for CXCL13 (Jenh, C. H. et al., Cytokine 15:113-121 (2001). CCL19 and CCL21 are produced by high endothelial venules and stromal cells in T-cell rich areas. They attract T-cells and mature dendritic cells bearing the receptor CCR7 (Campbell, J. J., et al. 1998. J. Cell. Biolo. 141:1053, Luther, S. A., et al. 2002. J Immunol 169:424-433). The expression of each of the lymphoid chemokines is dependent, in large part, on Lymphotoxin (LT)-α/β and TNFα (Hjelmstrom, P., et al. 2000. Am J Path 156:1133-1138, Ngo, V. N., et al. 1999. J. Exp. Med. 189: 403). Of note, (LT)-α/β and TNFα have been implicated in the pathogeneisis of organ specific autoimmune diseases, including EAE and MS (Selmaj K, et al. 1995. Neuroimmunol. 56(2):135, Suen, W. E., et al. 1997. J. Exp. Med. 186: 1233, Eugster, H-P, et al. 1998. Eur. J. Immunol. 29:626).

39. CXCL13 and CCL19 can also be produced by subpopulations of myeloid dendritic cells (Vissers, J. L. M., et al. 2001. Eur. J. Immunol. 31:1544, Forster, R., et al. 1996. Cell 87:1037-1047). This is particularly relevant since myeloid cells expressing a dendritic cell-like (dendriform) morphology and cell surface phenotype have been detected in inflamed CNS white matter, including specimens harvested from mice with EAE (FIG. 9) (Fischer, H. G. and Reichmann, G. 2001. J Immunol. 166:2717, (Serafini, B., et al. 2000. American Journal of Pathology 157:1991-2002). There is growing evidence that such dendriform cells differentiate from microglial precursors. For example, microglia differentiate into dendriform cells in vitro following stimulation with GM-CSF (Fischer, H. G. and Reichmann, G. 2001. J Immunol. 166:2717, Santambrogio, L., et al. 2001. PNAS 98:6295, Aloisi, F., et al. 2000. J. Immunol. 164:1705). GM-CSF is produced in spinal cords during EAE, most likely by infiltrating effector T-cells (Wong, R. L., et al. 1989. Cell. Immunol. 123:445).

40. Transgenic expression of CXCL13 or CCL21 in pancreatic islets trigger the local formation of organized lymphoid structures (Luther, S. A., et al. 2000. Immunity 12:471-481, Fan, L., et al. 2000. J. Immunol. 164:3955, Luther, S. A., et al. 2002. J Immunol 169:424-433). Furthermore, endogenous lymphoid chemokines have been detected in the target organs of patients with autoimmune diseases as well as at sites of chronic infection. For example, CXCL13 was found in the salivary glands of patients with Sjogren's syndrome, the synovial tissue of patients with rheumatoid arthritis, and in gastric mucosal tissue in the setting of refractory H. pylori infection (Salomonsson, S., et al. 2002. Scan J Immunol 55:336-342, Shi, K., et al. 2001. J Immunol 166:650-655, Mazzucchelli, L., et al. 1999. J. Clin. Inv. 104:R49-54, Takemura, S., et al. 2001. J. Immunol. 167:1072). In addition, CXCL13 is expressed in the thymus and kidneys of mice developing lupus nephritis (Ishikawa, S., et al. 2001. J Exp Med 193:1393-1402), while CCL21 is expressed in the pancreas of NOD mice developing diabetes (Hjelmstrom, P., et al. 2000. Am J Path 156:1133-1138).

Figure 11:
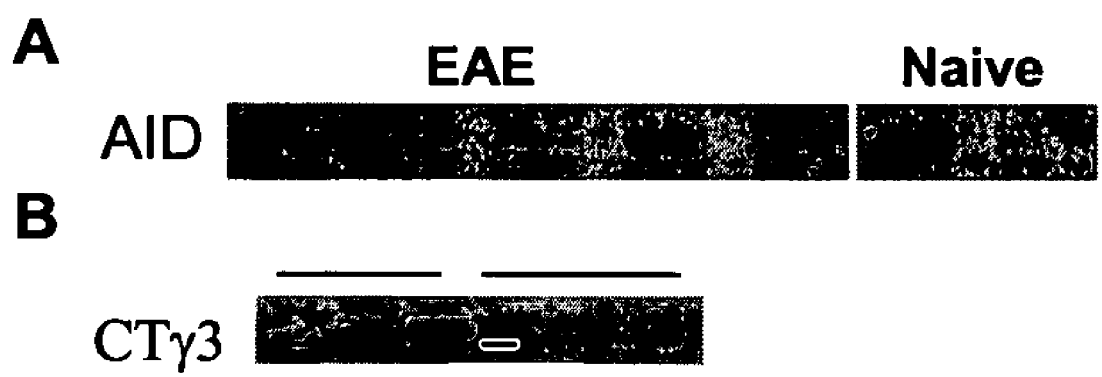
FIG. 11 shows the circle transcripts and AID mRNA are present in spinal cords of mice with EAE. Spinal cords were removed from PBS-perfused mice with EAE or naïve controls. RNA was extracted and RT-PCR performed with primers for AID (A) or CTγ3 (B), followed by Southern Blot Hybridization with internal oligonucleotide probes (for AID or CTγ3, respectively).

41. CXCR5 is most commonly expressed on B lymphocytes and CXCL13/CXCR5 interactions are critical for stimulating germinal center reactions. Therefore it is not surprising that previous studies have concentrated on the role of CXCL13 in autoimmune diseases that are viewed as primarily autoantibody driven, such as Sjogren's syndrome. By contrast, EAE is induced by autoreactive $CD4^+$ T-cells. The inflammatory process in MS is also believed to be driven, to a great extent, by myelin-reactive T-cells. Nonetheless, B cells and autoantibodies can participate in autoimmune demyelination, indicating that CXCL13 can be important in such disorders. First, B cells accumulate in chronic MS and EAE plaques over time. Furthermore, ninety percent of patients with MS develop oligoclonal bands in their cerebrospinal fluid, indicative of local antibody production in the CNS. Analysis of the immunoglobulin repertoire in spinal fluid and CNS biopsy specimens from MS patients suggest that antigen-driven B cell clonal expansion and somatic hypermutation occur within the target organ itself. Such phenomena are reminiscent of CXCL13-dependent germinal center reactions. Although the requirement for B cells in EAE varies based on the murine strain and autoantigen used for disease induction, autoantibodies against myelin antigens have been shown to facilitate demyelination in a wide variety of rodent as well as non-human primate models. Circle transcripts and AID mRNA are present in spinal cords of mice with EAE indicated that B cell differentiation occurs within the inflamed CNS (FIG. 11). Collectively, these data indicate that CXCL13 driven collaborations between T and B cells can play an important role in diseases such as EAE and MS.

Figure 9:
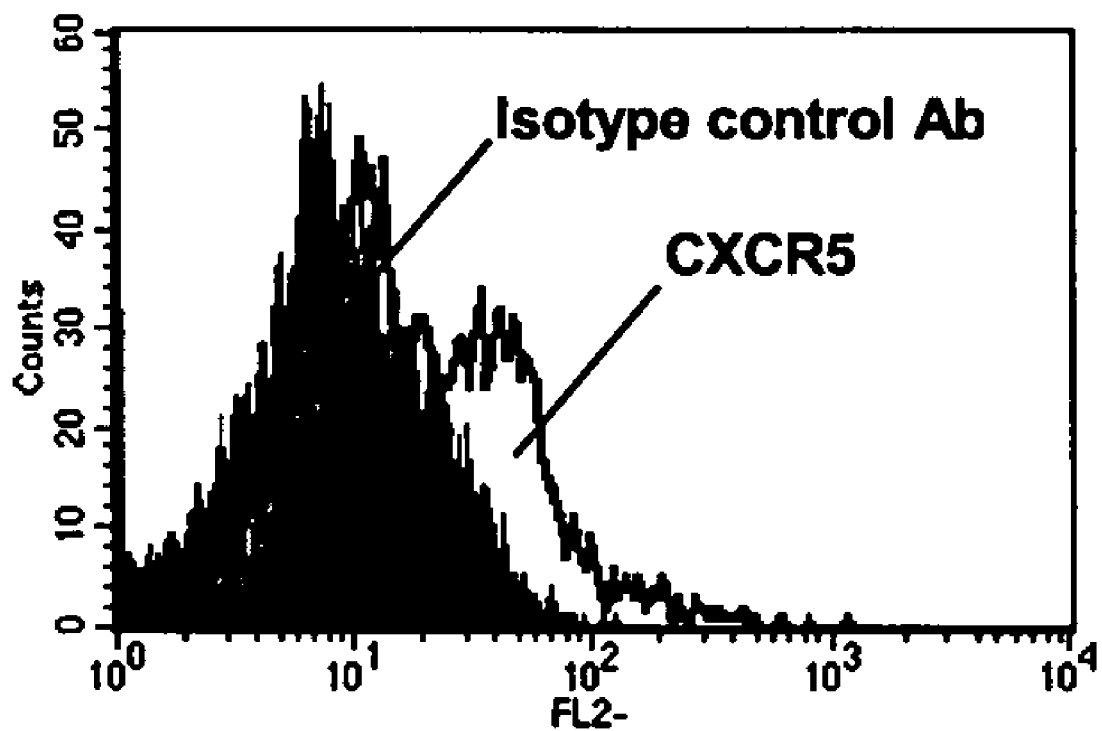
FIG. 9 shows that Encephalitogenic PLP-primed LN cells contain a subpopulation of $CXCR5^+$ $CD3^+$ T-cells. Draining LN cells from 10 PLP/CFA immunized SJL mice were resected on day 10, pooled and cultured with antigen. The cells were harvested at 96 h, washed, permeabilized, and stained with labeled anti-CXCR5 monoclonal antibodies or with isotype matched control antibodies, as indicated. Naïve LN cells do not contain detectable $CD3^+$ $CXCR5^+$ cells.

42. In addition to its effects on B cells, CXCL13 can play a role in EAE by modulating, and/or positioning a subset of CXCR5 expressing T-cells in the CNS. The majority of naïve, OVA-specific $CD4^+$ T-cells transiently upregulate CXCR5 following immunization with antigen in CFA. CXCR5 is detected on a significant percentage of $CD4^+$ T-cells from myelin protein immunized donors immediately ex vivo (FIG. 9). CXCR5 is also expressed by a subset of $iCOS^+$, $IL-7R^+$ effector memory cells ($T_{em}$). Hence, a primary role of CNS-produced CXCL13 in EAE can be the recruitment, positioning, and/or modulation of recently activated effector T-cells and/or autoaggressive $T_{em}$ in demyelinating plaques.

43. Herein it is disclosed that: (i) CXCL13, CCL19 and CCL21 are secreted by CD11c+ myeloid cells in EAE lesions; (ii) CXCL13, CCL19 and CCL21 recruit, position, and/or modulate CXCR5+ and CCR7+ leukocytes, respectively, in EAE plaques and help shape the cellular composition of white matter infiltrates; (iii) downstream effects of CNS lymphoid chemokines include the initiation of lymphoid neogenesis within plaques; (iv) CXCL13 also promotes B cell differentiation within the CNS, (v) CXCL13, CCL19 and CCL21 ultimately act to exacerbate the intensity and chronicity of clinical EAE, and; (vi) CXCL13 promotes relapses of EAE. The overarching principal is that ectopic production of lymphoid chemokines (such as CXCL13, CCL19 and CCL21) in the CNS drives the formation of organized inflammatory infiltrates characteristic of chronic EAE and MS lesions and thereby promotes clinical relapses and disease progression.

44. Lymphoid chemokines, including CCL19 (ELC), CCL21 (SLC) and CXCL13 (BLC), are constitutively expressed in secondary lymphoid tissues and are responsible for the distinctive architecture of those organs (Ansel, K. M., et al. 2000. *Nature* 406:309-314, Luther, S. A., et al. 2003. *J Exp Med.* 197:1191-1198). They direct leukocyte trafficking through the specialized compartments of LNs and spleen (Moser, B., and Loetscher, P. 2001. *Nature Immunology* 2:123-128, Cyster, J. G. 1999. *Science* 286:2098-2102). CCL19 and CCL21 attract CCR7+ naïve and central memory T-cells as well as activated dendritic cells to T-cell zones, whereas CXCL13 attracts CXCR5+ B cells and a subset of T helper cells (termed follicular T helper cells) to B cell rich areas (Gunn, M. D., et al. 1999. *J. Exp. Med.* 189:451-460, Kim, C. H., et al. 2001. *J Exp Med.* 193:1373-1381, Forster, R., et al. 1996. *Cell* 87:1037-1047, Ansel, K. M., et al. 1999. *J Exp Med.* 190:1123-1134). Lymphoid chemokines are ectopically expressed in nonlymphoid tissues during chronic inflammation. For example, CXCL13 was detected in gastric mucosal tissue and gastric lymphomas in the setting of refractory *Helicobacter pylori* infection (Mazzucchelli, L., et al. 1999. *J. Clin. Inv.* 104:R49-54). CCL21 also plays a role in the development of lymphoid-like structures within the liver in response to *Propionibacterium acnes* infection that were critical for elimination of the bacteria (Yoneyama, H., et al. 2001. *J Exp Med* 193:35-49). Furthermore, transgenic expression of lymphoid chemokines in the skin or pancreas drives the development of lymph node-like structures in those tissues (Luther, S. A., et al. 2000. *Immunity* 12:471-481)

45. While lymphoid chemokines might be expressed in non-lymphoid organs as part of an adaptive response against infection, these factors also have the potential to support chronic autoimmune inflammation. In fact, CCL19 and CCL21 are upregulated in the pancreas of NOD mice with diabetes as well as in cerebrovasculature of mice with EAE (Hjelmstrom, P., et al. 2000. *Am J Path* 156:1133-1138, Alt, C., et al. 2002. *Euro J Immunol* 32:2133-2144, Columba-Cabezas, S., et al. 2003. *Brain Pathology* 13:38-51). On the other hand, CXCL13 is expressed in the thymus and kidneys of mice developing experimental lupus nephritis (Ishikawa, S., et al. 2001. *J Exp Med* 193:1393-1402). With regard to autoimmune diseases in humans, CXCL13 has been detected in salivary glands from patients with Sjogren's syndrome and synovial tissues from patients with rheumatoid arthritis (Shi, K., et al. 2001. *J Immunol* 166:650-655, Salomonsson, S., et al. 2002. *Scan J Immunol* 55:336-342). CCL19 and CCL21 levels are elevated in cerebrospinal fluid from patients with MS, but not from patients with non-inflammatory neurological conditions (Pashenkov, M., et al. 2003. *J Neuroimmunol* 135:154-160). Nevertheless, prior to the present invention, the physiological role of endogenous lymphoid chemokines in the pathogenesis of these or other autoimmune diseases was not demonstrated.

46. Since CXCL13 is primarily known as an attractant for B cells and follicular T helper cells, investigations on its role in autoimmunity have largely been restricted to those diseases that are strongly associated with autoantibodies, such as Sjogren's syndrome and systemic lupus erythematosis (Ishikawa, S., et al. 2001. *J Exp Med* 193:1393-1402, 35). EAE, on the other hand, is mediated by myelin-specific CD4+ Th1 cells (Ando, D. G., et al. 1989. *Cell Immunol* 124:132-143). Th1 cells are also believed to drive the disease process in MS (Voskuhl, R. R., et al. 1993. *Autoimmunity* 15:137-143, Bielekova, B., et al. 2000. *Nat Med* 6:1167-1175). Nonetheless, several features of these autoimmune demyelinating syndromes suggest that CXCL13 could contribute to their pathogenesis. First, as mentioned above, infiltrates in demyelinating plaques have been found to display features of secondary lymphoid tissues and CXCL13 is a key regulator of lymphoid neogenesis. Hence, transgenic expression of CXCL13 under the rat insulin promoter induces the formation of lymph node-like structures in the pancreas (Luther, S. A., et al. 2000. *Immunity* 12:471-481). Pancreatic infiltrates in the transgenic mice are distinguished by a reticular stromal network, MAdCAM-1+ blood vessels and local induction of CCL21; all of these characteristics have been observed in EAE and/or MS lesions (Cross, A. H., et al. 1990. *Lab Invest* 63:162-170, Raine, C. S., et al. 1980. *Laboratory Investigation* 43:150-157, Raine, C. S., et al. 1984. *Laboratory Investigation* 51:534-546, Prineas, J. W., and Wright, R. G. 1978. *Laboratory Investigation* 38:409-421, Prineas, J. W. 1979. *Science* 203:1123-1125, Kanwar, J. R., et al. 2000. *J Neuroimmunol* 103:146-152, Alt, C., et al. 2002. *Euro J Immunol* 32:2133-2144, Columba-Cabezas, S., et al. 2003. *Brain Pathology* 13:38-51). Second, interactions between T and B cells occur within the CNS during autoimmune demyelination and have been implicated in MS and EAE pathogenesis (Baranzini, S. E., et al. 1999. *J Immunol* 163:5133-5144, Correale, J., and de los Milagros Bassani Molinas, M. 2002. *J of Neurology* 249: 375-389, Colombo, M., et al. 2000. *J Immunol* 164:2782-2789, Cross, A. H., et al. 2001. *J Neuroimmunol* 112:1-14, Lyons, J. A., et al. 1999. *European J Immunol* 29:3432-3439, Gerritse, K., et al. 1994. *J Neuroimmunol* 49:153-159, Genain, C. P., et al. 1995. *Journal of Clinical Investigation* 96:2966-2974). Such interactions are likely to be facilitated by local CXCL13 production. Also, it is disclosed and herein contemplated that CXCL13 can draw CXCR5+ effector or naïve T-cells that enter the CNS towards myeloid dendritic cells that, in turn, can act as antigen presenting cells. This can result in efficient reactivation of autoreactive T-cells within the target organ and/or priming of naïve myelin-reactive T-cells and epitope spreading.

47. Thus, disclosed herein are methods of screening for an agent that inhibits a T-cell mediated inflammatory response in a subject with an inflammatory response comprising administering to the subject the agent and detecting the presence of CXCL13 in the subject, wherein a reduction in the level of CXCL13 as compared to a control level indicates an agent that inhibits the inflammatory response.

48. The disclosed methods comprise methods of screening for an agent that inhibits a T-cell mediated inflammatory response. It is understood and herein contemplated that "T-cell mediated inflammatory response" means a CD4 T-cell, NK T-cell, or CD8 T-cell response whose mode of action is the secretion of inflammatory cytokines. Such responses can occur as the result of any type of immunological or physiological insult including but not limited to inflammatory conditions, viral infections, bacterial infections, yeast infections, parasitic infections, and cancers. T-cell mediated responses can be detected by numerous parameters including but not limited ELISA, ELISpot, and Flow cytometry (including, for example, Intracellular staining or CFSE staining), cytotoxicity assays (such as chromium release or JAM assays), and standard lymphoproliferation assays (ie, involving incorporation of tritiated thymidine in vitro or BdRU in vivo).

49. For example the disclosed screening methods can comprise methods of screening for an agent that inhibits a T-cell mediated inflammatory response, wherein the inflammatory response comprises a response to an inflammatory condition. Inflammatory conditions are well known in the art and can include autoimmune diseases. Thus also disclosed are methods of screening for an agent that inhibits a T-cell mediated inflammatory response, wherein the inflammatory response comprises a response to an inflammatory condition, wherein the inflammatory condition is selected from the group consisting of asthma, alopecia greata, systemic lupus erythematosus (SLE), rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial infarction, Alzheimer's disease, transplant rejection (allogeneic and xenogeneic), thermal trauma, any immune complex-induced inflammation, glomerulonephritis, myasthenia gravis, cerebral lupus, Guillain-Barre syndrome, vasculitis, systemic sclerosis, anaphlaxis, catheter reactions, atheroma, infertility, thyroiditis, ARDS, post-bypass syndrome, hemodialysis, juvenile rheumatoid, Behcets syndrome, hemolytic anemia, pemphigus, bullous pemphigoid, stroke, atherosclerosis, scleroderma, psoriasis, sarcoidosis, transverse myelitis, acute disseminated encephalomyelitis, post-infectious encephalomyelitis, subacute sclerosing panencephalitis, and chronic inflammatory demyelinating polyradiculopathy. In one embodiment, the inflammatory condition is multiple sclerosis. Each and any of these inflammatory conditions may also be excluded. Thus, for example, in certain embodiments, the inflammatory condition is not asthma, not SLE, not rheumatoid arthritis, not myasthenia gravis, not diabetes (e.g., not insulin dependent diabetes mellitus), or not transplant rejection.

50. Also disclosed are methods of screening for an agent that inhibits a T-cell mediated inflammatory response, wherein the inflammatory response comprises a response to a viral antigen. Viral antigens are well known in the art. It is understood that some of the pathogenic effects of a viral infection are not actually caused by the infecting virus, but by the immune response to the virus. For example, Lymphocytic Choriomeningitis virus (LCMV) will only induce pathogenic effects in hosts with functions T-cell responses. A host depleted of T-cells will show no ill effects of an LCMV infection. However, an immunologically intact host will potentially suffer sever meningitis due to the cytolytic action and cytokine secretion of T-cells. Additionally, some viruses have been implicated in the pathogenesis of inflammatory conditions such as multiple sclerosis. For example, Human Herpes virus-6 (HHV-6), measles, and Epstein Barr virus (EBV) have been implicated in MS pathogenesis. Thus specifically disclosed are methods of screening for an agent that inhibits a T-cell mediated inflammatory response, wherein the inflammatory response comprises a response to HHV-6. Similarly, also disclosed are methods of screening for an agent that inhibits a T-cell mediated inflammatory response, wherein the inflammatory response comprises a response to EBV or measles. Other inflammatory conditions are also associated with viruses. For example HTLV-1 is associated with a myelopathy that presents similarly to MS.

51. Therefore also disclosed are methods of screening for an agent that inhibits a T-cell mediated inflammatory response, wherein the inflammatory response comprises a response to a viral antigen, and wherein the viral antigen is selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian immunodeficiency virus, Human Immunodeficiency virus type-1, and Human Immunodeficiency virus type-2. Each and any of these viral antigens may also be excluded.

52. Also disclosed are methods of screening for an agent that inhibits a T-cell mediated inflammatory response, wherein the inflammatory response comprises a response to a bacterial antigen. For example, the bacterium *Chlamydia pneumonia* has been implicated in the pathogenesis of multiple sclerosis. Thus specifically disclosed are methods of screening for an agent that inhibits a T-cell mediated inflammatory response, wherein the inflammatory response comprises a response to *Chlamydia pneumonia*. Additionally, Nueroborrelisis (Lyme's disease of the central nervous system) can resemble MS. Thus specifically disclosed are methods of screening for an agent that inhibits a T-cell mediated inflammatory response, wherein the inflammatory response comprises a response to *Borrelia burgdorferi* (the bacterium that causes Lyme's disease).

53. Therefore also disclosed are methods of screening for an agent that inhibits a T-cell mediated inflammatory response, wherein the inflammatory response comprises a response to a bacterial antigen, and wherein the bacterial antigen is selected from the group consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Borrelia burgdorferi, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Chlamydia pneumonia, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae*,

*Haemophilus ducreyi*, other *Hemophilus* species, *Clostridium tetani*, other *Clostridium* species, *Yersinia enterolitica*, and other *Yersinia* species. Each and any of these bacterial antigens may also be excluded.

54. Cancer, and in particular cancer antigens, are known to induce an inflammatory response in a subject. Thus also disclosed are methods of screening for an agent that inhibits a T-cell mediated inflammatory response, wherein the inflammatory response comprises a response to a cancer antigen. Cancer antigens are well known in the art and therefore, specifically disclosed are methods, wherein the antigen is related to a cancer selected from the group consisting of lymphomas (Hodgkins and non-Hodgkins), B cell lymphoma, T-cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumours, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colorectal cancers, prostatic cancer, or pancreatic cancer. Each and any of these cancer antigens may also be excluded. In addition, each and any inflammatory condition arising from cancer (i.e., malignancy) may be excluded.

55. It is understood that the disclosed screening methods can be used in experimental settings. Such settings can require the induction of the T-cell mediated inflammatory response in order for an agent to have inflammation available for inhibition. It is understood that the necessity of inducing the inflammatory response is known to those of skill in the art. That is, those of skill in the art will recognize if the inflammatory response being inhibited needs to be induced and how the induction can occur. Thus, specifically contemplated are methods of screening for an agent that inhibits a T-cell mediated inflammatory response in a subject, comprising the steps of a) administering the agent to the subject, b) inducing the inflammatory response in the subject, and c) detecting CXCL13 in the subject, wherein a reduction in the level of CXCL13 in the subject as compared to a control level indicates an agent that inhibits an inflammatory response. Optionally step (a) can precede, follow, or occur simultaneously with step (b).

56. Many different inducers are known in the art and one of skill in the art will understand the appropriate inducer to use for the inflammatory response being studied. It is understood that the inflammatory response can be induced by a peptide, polypeptide, or protein. For example, the inducer can be a myelin protein such as myelin basic protein. In the EAE model of MS the inflammatory condition can be induced by proteolipid protein (PLP), myelin oligodendrocyte protein (MOG), myelin basic protein (MBP) or an antigenic fragment thereof (e.g., $PLP_{135-155}$ and $PLP_{139-151}$ $MBP_{Ax1-11}$ or $MOG_{35-55}$).

57. The disclosed methods can also be performed using other molecules to assess inhibition. For example, CXCR5, the ligand for CXCL13 may be used to detect inhibition. Thus also disclosed are methods of screening for an agent that inhibits a T-cell mediated inflammatory response in a subject, comprising the steps of a) administering the agent to the subject, b) inducing the inflammatory response in the subject, and c) detecting CXCR5 in a sample from the subject, a reduction in the level of CXCR5 in the subject as compared to a control level indicating an agent that inhibits an inflammatory response.

58. The disclosed screening methods can use tissue samples from a subject to detect the presence of CXCL13 or CXCR5. Thus also contemplated are methods of screening for an agent that inhibits T-cell mediated inflammatory responses in a subject with an inflammatory response comprising administering to the subject the agent and detecting the presence of CXCL13 or CXCR5, wherein the CXCL13 or CXCR5 is detected in a tissue sample from the subject.

59. The tissue samples can be solid tissue or organs as well as fluid tissue. Thus disclosed are screening methods wherein the tissue sample comprises a blood, lymphoid tissue samples (e.g., lymph node, splenic tissue, bone marrow), cerebrospinal fluid, synovial fluid. Tissue samples may be taken from the site of inflammation or at other sites. It is understood that the tissue sample can comprise lymphoid tissue, but can also comprise non-lymphoid tissue.

60. The disclosed screening methods use CXCL13 or CXCR5 as markers to assess inhibition. The art is replete with examples of methods of detecting cellular markers. For example surface markers and their ligands can be detected using antibodies specific to the marker of interest. Therefore specifically disclosed methods of screening for an agent that inhibits a T-cell mediated inflammatory response in a subject with an inflammatory response comprising administering to the subject the agent, inducing the inflammatory response when necessary, and detecting the presence of CXCL13 or CXCR5 in the subject, wherein CXCL13 or CXCR5 is detected by staining the tissue sample with CXCL13 or CXCR5 antibodies respectively, wherein the antibodies are linked to a detectable moiety. Assays used to detect antibodies are well-known in the art and include but are not limited to flow cytometry, immunohistochemistry, ELISA, and ELISpot.

61. In some instances it can be necessary to determine the specificity and activation state of infiltrating T-cells that are detected due to the presence of CXCR5 on their surface. The advantage of knowing the T-cell specificity and activation state is the ability to determine if the CXCR5+ T-cells are specific to the inflammation being inhibited or directed to unrelated antigens. Thus, only the targeted T-cells are evaluated to assess inhibition. Therefore, specifically disclosed are screening methods further comprising determining the antigen specificity of CXCR5 positive T-cells in the sample. Also disclosed are screening methods further comprising determining the activation state of any CXCR5 positive T-cells in the sample. Many markers for assessing the activation state are known in the art. Such markers can include but are not limited to ICOS, CD11a, CD45RO, CD45RA, CD44, CD62L, CD27, and CD43).

Methods of Treatment

62. Agents, including but not limited to, those identified via the screening methods disclosed herein can be used for the treatment of T-cell mediated inflammation specifically providing a treatment for inflammatory conditions, including but not limited to inflammatory conditions such as multiple sclerosis (MS). Thus, one embodiment of the disclosed invention is a method of treating a subject with multiple sclerosis, comprising administering to the subject a therapeutic amount of an agent, e.g., an agent identified by the disclosed screening methods. For example, disclosed are methods of treating a subject with MS, comprising administering to the subject a therapeutic amount of the agent identified by the disclosed screening methods.

63. The disclosed compositions can be used to treat a subject marked by any disease with uncontrolled T-cell mediated inflammation. For example, specifically disclosed are methods of treating a subject with an inflammatory condition comprising administering to the subject an effective amount of an agent that inhibits the interaction of CXCL13 and a receptor that specifically binds CXCL13 (e.g., CXCR5), wherein the inhibition of interaction of CXCL13 with a receoptor (e.g., CXCR5) reduces the inflammatory condition.

64. Reduction in the inflammatory condition is determined by assessing a variety of clinical and laboratory parameters. Such parameters include the frequency and/or size of gadolinium-enhancing lesions detected by brain or spinal cord MRI scans, white matter lesion burden determined by MRI scanning, cerebrospinal fluid pleocytosis, cerebrospinal fluid IgG synthesis rate and/or IgG index, cerebrospinal fluid oligoclonal banding, serum anti-myelin antibody titers, serum autoreactive antibody titers, the frequency of autoreactive T-cells among peripheral mononuclear cells (including myelin-specific T-cells), C-reactive protein, erythrocyte sedimentation rate and serum biomarkers or surrogate markers that have yet to be defined.

65. The disclosed treatment methods employ agents to inhibit inflammation, prevent inflammation (i.e., prophylactically), or reduce ongoing inflammation. The agents can include, but are not limited to antibodies that bind CXCL13. These antibodies include neutralizing antibodies that can prevent CXCL13 from binding to its receptor(s), e.g., CXCR5 and/or CXCR3 (i.e., a blocking antibody), or otherwise interfere with its biological activity. It is understood that the antibody can be a polyclonal or monoclonal antibody or antigenic fragments thereof. The antibody can be a naturally-occurring antibody. The antibody can also be an engineered form of antibody, including but not limited to, a single chain antibody, a Fab fragment, a Fab' fragment, a F(ab')$_2$ fragment, a scFv fragment (i.e., single chain variable region), a minibody, a dimeric antibody (diabody), a trimeric antibody (triabody), or a tetrameric antibody (tetrabody). The antibody or antibody fragment can be used as a fusion protein. In one embodiment, the agent is a human monoclonal antibody or fragment thereof that specifically binds CXCL13 and has neutralizing activity as determined by any suitable assay disclosed herein or known in the art. The agent can also comprise a soluble form of CXCR5 to compete with the membrane bound ligand and limit the signaling ability of the chemokine CXCL13. Likewise, the agent can comprise a soluble form of any other receptor (e.g., CXCR3) to which CXCL13 binds and through which CXCL13 exerts biological activity as determined by an suitable assay disclosed herein or known in the art, wherein the soluble receptor form competes with membrane bound ligand and limits the signalling ability of CXCL13.

66. Thus, specifically disclosed are methods of reducing the exacerbation of an inflammatory condition in a subject comprising administering to the subject an effective amount of an agent that inhibits the interaction of CXCL13 and CXCR5, the inhibition of CXCL13 interaction with CXCR5 reducing the exacerbation. The interaction between CXCL13 and CXCR5 provides the signaling through which T-cells are drawn to an area of inflammation and stimulated to produce inflammatory cytokines. Thus any agent that blocks this interaction can be used in the present methods. For example, specifically disclosed and herein contemplate are methods of treating a subject with an inflammatory condition comprising administering to the subject an effective amount of an agent that inhibits the interaction of CXCL13 and CXCR5, wherein the agent is an antibody to CXCR5 and wherein the antibody blocks CXCL13 binding without causing signaling through CXCR5. The agent can also comprise a small organic molecule or a macromolecule that binds to either CXCL13 or CXCR5 so as to inhibit interactions therebetween. The agent can also comprise an antibody, small organic molecule, or macromolecule that interferes with the interaction of CXCL13 and any other receptor (e.g., CXCR3) or ligand to which CXCL13 binds, and which inhibits and inflammatory response.

67. Therefore an embodiment of the present invention is a method of inhibiting an inflammatory response in a subject comprising administering to the subject an effective amount of an agent that inhibits the interaction of CXCL13 and CXCR5, the inhibition of CXCL13 interaction with CXCR5 inhibiting the inflammatory response.

68. Also disclosed are methods of reducing a T-cell-mediated inflammatory response or condition e.g., an autoimmune condition, in a subject, comprising administering to the subject in need thereof an effective amount of an agent that inhibits CXCL13 activity, the inhibition of CXCL13 reducing the inflammatory response or condition.

69. The disclosed treatment methods can be used to treat inflammatory conditions. Inflammatory conditions can include but are not limited to autoimmune conditions and generalized conditions marked by systemic or localized inflammation. Thus it is understood that disclosed are methods of treating an inflammatory response or condition, wherein the inflammatory response or condition is selected from the group consisting of asthma, alopecia greata, systemic lupus erythematosus, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial infarction, Alzheimer's disease, transplant rejection (allogeneic and xenogeneic), thermal trauma, any immune complex-induced inflammation, glomerulonephritis, myasthenia gravis, cerebral lupus, Guillain-Barre syndrome, vasculitis, systemic sclerosis, anaphlaxis, catheter reactions, atheroma, infertility, thyroiditis, ARDS, post-bypass syndrome, hemodialysis, juvenile rheumatoid, Behcets syndrome, hemolytic anemia, pemphigus, bullous pemphigoid, stroke, atherosclerosis, scleroderma, psoriasis, sarcoidosis, transverse myelitis, acute disseminated encephalomyelitis, post-infectious encephalomyelitis, subacute sclerosing panencephalitis, polymyositis, dermatomyositis, incusion body myopathy, and chronic inflammatory demyelinating polyradiculopathy. Each and any of these inflammatory responses or conditions may also be excluded. Thus, for example, in certain embodiments, the inflammatory condition is not asthma, not SLE, not rheumatoid arthritis, not myasthenia gravis, not diabetes (e.g., not insulin dependent diabetes mellitus), or not transplant rejection. Each and any inflammatory condition associated with cancer (i.e., malignancy) may be excluded, as well.

70. It is understood that inflammatory conditions can also include neuroinflammatory responses or conditions including but not limited to chronic neuroinflammatory conditions, relapsing and remitting conditions, and chronic demyelinating conditions. For example, the disclosed methods of treatment can be used to treat a neuroinflammatory condition, wherein the neuroinflammatory condition is selected from the group consisting of multiple sclerosis (MS), experimental allergic encephalomyelitis (EAE), Guillain-Barre syndrome, Alzheimer's disease, transverse myelitis, acute disseminated encephalomyelitis, post-infectious encephalomyelitis, subacute sclerosing panencephalitis, and chronic inflammatory demyelinating polyradiculopathy. Thus, for example, disclosed herein are methods of treating a neuroinflammatory condition wherein the neuroinflammatory condition is multiple sclerosis. Each and any of these neuroinflammatory conditions may also be excluded.

71. The inflammatory conditions of the invention involve the inflammatory response of leukocytes. It is understood that CXCR5+ B cells, T-cells, and NK T-cells can be involved in generating the inflammatory response and are recruited to the site of inflammation. Thus it is understood and disclosed herein that the recruited leukocytes can be B cells (including but not limited to memory B cells), T-cells (e.g., CD4 and CD8 T-cells) and NK T-cells. Lymphoid inducer cells, a unique subpopulation of hematopoetic cells, also express CXCR5 and can be involved in the initiation or perpetuation of an inflammatory condition. The inflammatory conditions treated by the disclosed methods can be T-cell mediated. In particular, the T-cell mediated condition or response can be mediated by antigen-specific pathogenic CD4+ T-cells. More specifically, the disclosed T-cells can be myelin reactive T-cells.

72. As used herein, the inflammatory response or condition can be induced by autoantibodies. Autoimmune diseases, for example, are characterized by such autoantibodies.

73. The CXCL13 affected by the methods of the invention are produced by CD11c+ myeloid dendritic cells, e.g., in lesions of the central nervous system of the subject.

74. The agent optionally inhibits the action of CXCL13 in recruiting, positioning, and/or modulating CXCR5-expressing peripheral leukocytes or lymphoid tissue inducer cells in lesions. Furthermore, the agent optionally inhibits the action of CXCL13 in recruiting, positioning, and/or modulating CXCR3-expressing B and/or T-cells in lesions. Thus the agent plays a significant role in interrupting the pathways involved in the underlying inflammatory condition.

75. The leukocytes recruited, spatially positioned (with respect to other cell types), and/or modulated by the CXCL13 are effector/memory T ($T_{em}$) lymphocytes. The lymphocytes optionally have been activated by antigen and express iCOS, IL-7 receptor (IL-7R) and CD40 ligand (CD40L). Optionally, the recruited leukocytes are non polarized memory T-cells, myeloid cells, or CD4+ CD3-lymphoid tissue inducer cells.

76. The agent can inhibit the action of CXCL13 in facilitating interactions between CXCR5+ leukocytes within tissue infiltrates or can inhibit the action of CXCL13 in triggering lymphoid neogenesis. As used herein, "lymphoid neogenesis" refers to development of organized lymphoid structures within a target organ.

77. The agent can be an antisense oligonucleotide or an siRNA molecule that inhibits expression of CXCL13. Such an antisense oligonucleotide or siRNA should be sufficiently complementary to the sequence of DNA or mRNA encoding CXCL13 so as to have the proper antisenseor interfering property. The term "siRNA" as used herein refers to any nucleic acid molecule capable of mediating RNA interference ("RNAi") or gene silencing; see for example, Kreutzer et al., International PCT Publication No. WO 00/44895; Zemicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. For example, the siRNA can be a double-stranded polynucleotide molecule comprising self-complementary sense and antisense regions, wherein the antisense region comprises complementarity to a target nucleic acid molecule. The siRNA can be a single-stranded hairpin polynucleotide having self-complementary sense and antisense regions, wherein the antisense region comprises complementarity to a target nucleic acid molecule. The siRNA can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active siRNA capable of mediating RNAi. As used herein, siRNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not contain any ribonucleotides (e.g., nucleotides having a 2'-OH group). The modified short interfering nucleic acid molecules of the invention can also be referred to as short interfering modified oligonucleotides "siMON." As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA, short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing.

78. In one embodiment of the present invention, each sequence of an siRNA molecule of the invention is independently 18 to 24 nucleotides in length, in specific embodiments about 18, 19, 20, 21, 22, 23, or 24 nucleotides in length. In another embodiment, the siNA duplexes of the invention independently comprise between about 17 and about 23 base pairs. In yet another embodiment, siRNA molecules of the invention comprising hairpin or circular structures are about 35 to about 55 nucleotides in length, or about 38 to about 44 nucleotides in length and comprising 16-22 base pairs.

79. This invention provides a method of inhibiting extra-lymphatic lymphoid neogenesis in a subject comprising administering to the subject an effective amount of an agent that inhibits CXCL13, the inhibition of CXCL13 inhibiting lymphoid neogenesis.

80. Further provided are methods of inhibiting accumulation and/or stimulation of $T_{em}$ cells or activated B cells in a CNS inflammatory site in a subject, comprising administering to the subject an effective amount of an agent that inhibits CXCL13, CXCL13 inhibition thereby inhibits accumulation and/or stimulation through the CXCR5 receptor. Also disclosed are methods of inhibiting B cell activation or differentiation in a CNS inflammatory site in a subject, comprising administering to the subject an agent that inhibits CXCL13, inhibition of CXCL13 inhibiting B cell activation or differentiation. Also disclosed are methods of inhibiting the migration of CD4+CXCR5+ $T_{em}$ cells or CXCR5+ B cells from the periphery into the CNS in a subject, comprising administering to the subject an effective amount an agent that inhibits the action of CXCL13 on said T or B cells, inhibition of CXCL13 inhibiting said migration.

81. Inflammation can occur anywhere in a subject. Therefore it is necessary for the agents to be administered systemically in the event of systemic inflammatory conditions or administered locally or regionally, in the event of local or regional inflammatory conditions. It is understood that one of skill in the art will be able to determine if the inflammation is systemic or local and can administer the agent accordingly.

82. It is well known in the art that some inflammatory conditions are chronic in nature. Moreover, it is understood that some chronic inflammatory conditions can appear to be under control, but re-emerge or relapse. Thus specifically contemplated are methods of treating a T-cell mediated inflammatory response or condition in a subject, comprising administering to the subject in need thereof an effective amount of an agent that inhibits CXCL13, wherein the agent is administered after the inflammatory response or condition has been initially induced but before a first relapse. Also disclosed are methods of treatment of a T-cell mediated inflammatory response or condition, wherein the agent is administered at the time of a first relapse. Also disclosed are methods of treatment of a T-cell mediated inflammatory response or condition, wherein the agent is administered at the time of, or following, the initial clinical exacerbation (ie, the presenting episode) but prior to a first clinical relapse. Also disclosed are methods of treatment of a T-cell mediated inflammatory response or condition, wherein the agent is administered when subclinical inflammatory activity has been detected (ex. by MRI scans or blood tests) that is likely to evolve into a clinical syndrome in the future. Also disclosed are methods of treatment of a T-cell mediated inflammatory response or condition, wherein the agent is administered after a first relapse. For example, specifically contemplated are methods of treatment of the invention, wherein said administration is performed at the time of relapse of a chronic neuroinflammatory condition. Also disclosed are method of inhibiting the binding or other interactions between CXCL13 and a CXCR5-expressing cell (or a cell expressing any other receptor that interacts with CXCL13, e.g., CXCR3) that can participate in the induction, progression or expression of a T-cell-mediated neuroinflammatory response, comprising providing to said cell an amount of an agent effective in inhibiting CXCL13 binding to said cell. In one embodiment, the neuroinflammatory response is multiple sclerosis.

83. It is disclosed and herein contemplated that administration of an agent to treat an inflammatory condition may not be curative, but may reduce the inflammation. Such an agent would then be needed for the life of the subject or until the inflammatory condition is eliminated. Thus also disclosed are methods of the invention, wherein the agent is administered chronically. Also disclosed are methods of the invention, where the administration of said agent aborts the relapse, or results in more complete and or more rapid recovery from a first or subsequent relapse. It is also understood and herein contemplated that administration of the disclosed agents can halt the progression of a chronic inflammatory condition. It is also understood that such treatment can prevent further episodes of an inflammatory condition. Thus also disclosed are method of the invention, wherein the administration of said agent stabilizes the clinical status of a patient with a chronic inflammatory condition. (prevents or reduces future accumulation of deficits). Such long term administrations are well-known in the art and can involve daily, weekly, or monthly adminstrations of the agent or alternatively the agent can be administered in a controlled-release or depot formulation.

84. It is understood that inflammatory conditions can have multiple effects on a subject which result in undersireable symptoms. It is also understood that there are circumstances in which multiple agents will be preferred to single agent administration for the control of inflammatory conditions. Thus specifically disclosed are methods of treating an inflammatory condition wherein the agents of the treatment methods disclosed herein may be administered in combination with one or more additional drugs that are useful for (a) inhibiting the inflammatory response or condition, and/or (b) treating any other undesired associated symptom. It is recognized that one of skill in the art will be able to determine if combination therapy is preferred over single agent use.

Antibodies

Antibodies Generally

85. The terms "antibody," "antibodies," "immunoglobulins," or "immunoglobulins" refer to antibodies comprised of two immunoglobulin heavy chains and two immunoglobulin light chains as well as a variety of forms besides antibodies; including, for example, Fv, Fab, and F(ab')2 as well as bifunctional hybrid antibodies (e.g., Lanzavecchia et al., *Eur. J. Immunol.* 17, 105 (1987)) and single chains (e.g., Huston et al., *Proc. Natl. Acad. Sci. U.S.A.*, 85, 5879-5883 (1988) and Bird et al., *Science* 242, 423-426 (1988), which are incorporated herein by reference). (See, generally, Hood et al., *Immunology*, Benjamin, N.Y., 2ND ed. (1984), Harlow and Lane, ANTIBODIES. A LABORATORY MANUAL, Cold Spring Harbor Laboratory (1988) and Hunkapiller and Hood, *Nature*, 323, 15-16 (1986), which are entirely incorporated herein by reference).

86. The antibodies for use in the present invention include, but are not limited to, polyclonal, monoclonal, multispecific, human, humanized or chimeric antibodies, single chain antibodies, scFv fragments, Fab fragments, F(ab')2 fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

87. The antibodies for use in the present invention also include, but are not limited to, engineered forms of antibodies and antibody fragments such as diabodies, triabodies, tetrabodies, and higher multimers of scFvs, as well as minibodies, such as two scFv fragments joined by two constant (C) domains. See, e.g., Hudson, P. J. and Couriau, C., *Nature Med.* 9: 129-134 (2003); U.S. Publication No. 20030148409; U.S. Pat. No. 5,837,242 (all of which are entirely incorporated by reference herein).

88. The antibodies for use in the present invention may be from any animal origin including birds and mammals. Preferably, the antibodies are human, murine (e.g., mouse and/or rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described, for example in, U.S. Pat. No. 5,939,598 by Kucherlapati et al. The antibodies are tested for their desired activity using the in vitro assays described herein, or by analogous methods, after which their in vivo therapeutic and/or prophylactic activities are tested according to known clinical testing methods.

89. The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855, 1984, all of which are herein incorporated by reference in their entireties).

90. Monoclonal antibodies can be prepared using a wide variety of techniques known in the art including the use of hybridoma, recombinant, and phage display technologies, or a combination thereof. For example, monoclonal antibodies of the invention can be prepared using hybridoma methods, including those known in the art such as those described by Kohler and Milstein, *Nature,* 256:495, 1975; Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563-681 (Elsevier, N.Y., 1981) (said references incorporated by reference in their entireties). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

91. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. For example, the monoclonal antibodies may also be made by recombinant DNA methods, such as those described in U.S. Pat. No. 4,816,567 (Cabilly et al.) (herein incorporated by reference in its entirety). DNA encoding the monoclonal antibodies of the invention can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al. (herein incorporated by reference in their entireties).

92. In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566 (herein incorporated by reference in their entireties). Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

93. The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr Opin Biotechnol* 3:348-354, 1992). Examples of techniques which can be used to produce single-chain Fvs and antibodies, as well as diabodies, triabodies, and tetrabodies, include those described in U.S. Pat. Nos. 4,946,778 and 5,258,498; Huston et al., *Methods in Enzymology* 203:46-88 (1991); Shu et al., *PNAS* 90:7995-7999 (1993); Skerra et al., *Science* 240:1038-1040 (1988); U.S. Application Publication No. 20020018749 and U.S. Pat. No. 5,837,242 (herein incorporated by reference in their entireties).

94. Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437-444; (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

95. As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Human Antibodies

96. The human antibodies of the invention can be prepared using any technique. Examples of techniques for human monoclonal antibody production include those described by Cole et al. (*Monoclonal Antibodies and Cancer Therapy,* Alan R., Ed. Liss, p. 77, 1985) and by Boemer et al. (*J Immunol,* 147(1):86-95, 1991). Human antibodies of the invention (and fragments thereof) can also be produced using phage display libraries (Hoogenboom et al., *J Mol Biol,* 227: 381, 1991; Marks et al., *J Mol Biol,* 222:581, 1991).

97. For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library. Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

98. As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); Sawai et al., *AJRI* 34:26-34 (1995); and Better et al., *Science* 240:1041-1043 (1988) (all incorporated by reference in their entireties).

99. Fully human antibodies can be produced according to the method taught by US 2002 0123057A1, "In vitro methods of producing and identifying immunoglobulin molecules in eukaryotic cells," published 5 Sep. 2002, which is incorporated herein by reference in its entirety. Briefly, a mouse (or human) heavy chain V region (VH) linked to a human heavy chain constant region (CH) is employed to select fully human immunoglobulin light chains from a library of such light chains that when paired with the mouse (or human) VH confers specificity for the desired antigen (e.g., CXCL13). The selected fully human immunoglobulin light chains are then employed to select fully human immunoglobulin heavy chains from a library of such heavy chains that, when paired with the fully human light chain, confer specificity for the desired antigen (e.g., CXCL13). Similarly, the mouse (or human) light chain V region (VL) linked to a human light chain constant region (CL) may be employed to select fully human immunoglobulin heavy chains from a library of such heavy chains that when paired with the mouse (or human) VL confers specificity for the desired antigen (e.g., CXCL13). The selected fully human immunoglobulin heavy chains are then employed to select fully human immunoglobulin light chains from a library of such light chains that, when paired with the fully human heavy chain, confer specificity for the desired antigen (e.g., CXCL13). Frequently, the fully human antibody selected in this fashion has epitope specificity that is identical or closely related to that of the original mouse (or human) antibody.

100. The method of US Patent Application Publication No. 2002 0123057 µl may also be used with a library of heavy or light chains of which all members have one or more non-human (e.g., murine) CDRs. In one example, each member of the library comprises a CDR3 region derived from an isolated murine monoclonal antibody specific for the desired antigen (e.g., CXCL13).

101. The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255, 1993; Jakobovits et al., *Nature*, 362:255-258, 1993; Bruggermann et al., *Year in Immunol.* 7:33, 1993). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

102. Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Humanized Antibodies

103. Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fc, Fv, Fab, Fab', or other antigen-binding portion of an antibody) which contains a portion of an antigen binding site from a non-human (donor) antibody integrated into the framework of a human (recipient) antibody.

104. To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525, 1986, Reichmann et al., *Nature*, 332:323-327, 1988, and Presta, *Curr Opin Struct Biol*, 2:593-596, 1992).

105. Methods for humanizing non-human antibodies are well known in the art. For example, humanized antibodies can be generated according to the methods of Winter and co-workers (Jones et al., *Nature*, 321:522-525, 1986, Riechmann et al., *Nature*, 332:323-327, 1988, Verhoeyen et al., *Science*, 239:1534-1536, 1988), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of Antibodies

106. Antibodies of the invention are preferably administered to a subject in a pharmaceutically acceptable carrier. Suitable carriers and their formulations are described in *Remington: The Science and Practice of Pharmacy* (19th ed.) A. R. Gennaro, Ed., Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped particles, e.g., films, liposomes or microparticles. It will be apparent to those persons skilled in the art that certain carriers may be more preferable depending upon, for instance, the route of administration and concentration of antibody being administered.

107. The antibodies can be administered to the subject, organ, tissue, or cell by a variety of methods. For example, the antibody can be added to in vitro culture. Various other delivery systems are known and can be used to administer a compound of the invention, e.g., encapsulation in liposomes, microparticles, microcapsules, recombinant cells capable of expressing the compound, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. Local or intravenous injection is preferred.

108. In one embodiment, the entire antibody dose is provided in a single bolus. Alternatively, the dose can be provided by multiple administrations, such as an extended infusion method or by repeated injections administered over a span of hours or days.

109. In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

110. In another embodiment, the compound or composition can be delivered in a vesicle, in particular a liposome (see Langer, *Science* 249:1527-1533 (1990); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327; see generally ibid.).

111. In yet another embodiment, the compound or composition can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see MEDICAL APPLICATIONS OF CONTROLLED RELEASE, LANGER AND WISE (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, *J., Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in MEDICAL APPLICATIONS OF CONTROLLED RELEASE, supra, vol. 2, pp. 115-138 (1984)). Other controlled release systems are discussed in the review by Langer (*Science* 249:1527-1533 (1990)).

112. Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., 1985 ch. 22 and pp. 303-357; Smith et al., Antibodies in Human Diagnosis and Therapy, Haber et al., eds., Raven Press, New York, 1977 pp. 365-389. A typical daily dosage of the antibody used alone might range from about 1 µg/kg to up to 100 mg/kg of body weight or more per day, depending on the factors mentioned above.

Pharmaceutical Carriers/Delivery of Pharmaceutical Products

113. As described above, the compositions can also be administered in vivo in a pharmaceutically acceptable carrier. By "pharmaceutically acceptable" is meant a material that is not biologically or otherwise undesirable, i.e., the material may be administered to a subject, along with the cell, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

114. The compositions may be administered orally, parenterally (e.g., intravenously), by intramuscular injection, by intraperitoneal injection, transdermally, extracorporeally, intranasally, topically or the like. The exact amount of the compositions required will vary from subject to subject, depending on the species, age, weight and general condition of the subject, the severity of the disorder being treated, the particular cell used, its mode of administration and the like. Thus, it is not possible to specify an exact amount for every composition. However, an appropriate amount can be determined by one of ordinary skill in the art using only routine experimentation given the teachings herein.

115. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

116. The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem*, 2:447-451, 1991; Bagshawe, K. D., *Br J Cancer*, 60:275-281, 1989; Bagshawe, et al., *Br J Cancer*, 58:700-703, 1988) Senter, et al., *Bioconjugate Chem*, 4:3-9, 1993; Battelli, et al., *Cancer Immunol Immunother*, 35:421-425, 1992; Pietersz and McKenzie, *Immunolog. Reviews*, 129:57-80, 1992; and Roffler, et al., *Biochem Pharmacol*, 42:2062-2065, 1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Res.*, 49:6214-6220, 1989; and Litzinger and Huang, *Biochimica et Biophysica Acta*, 1104:179-187, 1992). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA Cell Biol* 10:6, 399-409, 1991).

Pharmaceutically Acceptable Carriers

117. The compositions, including antibodies, can be used therapeutically in combination with a pharmaceutically acceptable carrier.

118. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

119. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

120. The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies or agents can be administered intravenously, intraperitoneally, intramuscularly, subcutaneously, intracavity, or transdermally.

121. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

122. Formulations for topical administration may include ointments, lotions, creams, gels, drops, suppositories, sprays, liquids, and powders. Conventional pharmaceutical carriers, aqueous, powder or oily bases, thickeners, and the like may be necessary or desirable.

123. Compositions for oral administration include powders or granules, suspensions or solutions in water or non-aqueous media, capsules, sachets, or tablets. Thickeners, flavorings, diluents, emulsifiers, dispersing aids or binders may be desirable.

124. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, tri-alkyl and aryl amines and substituted ethanolamines.

Therapeutic Uses

125. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days. For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

126. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

127. The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Methods

Mice.

128. Female SJL, B10.PL and C57BL/6 mice were obtained from Jackson Laboratories (Fredrick, Md.). CXCL13 deficient mice on the C57BL/6 background were also obtained (Ansel, K. M., et al. 2000. *Nature* 406:309-314, Ansel, K. M., et al. 2002. *Immunity* 16:67-76). All animals were housed under specific-pathogenfree, barrier facility conditions.

Peptides.

129. Myelin peptides were synthesized by Macromolecular Resources (Fort Collins, Colo.) and purified by HPLC. The sequences were as follows: Proteolipid protein $(PLP)_{139-151}$: HSLGKWLGHPDKF (SEQ ID NO: 1); Myelin basic protein $(MBP)_{Ac1-11}$: Ac-ASQKRPSQRHG (SEQ ID NO: 2) and myelin oligodendrocyte glycoprotein $(MOG)_{35-55}$: MEVGWYRSPFSRVVHLYRNGK (SEQ ID NO: 3).

Induction of EAE by Active Immunization.

130. Mice were immunized with 100 µg of the relevant myelin peptide emulsified in CFA (with 4 mg/ml heat-killed *Mycobacteria tuberculosis* H37Ra; vol:vol) by subcutaneous (s.c.) injection at four sites over the flanks. *Bordetella pertussis* toxin (List Laboratories) was injected intraperitoneally (i.p., 200 ng/mouse) on days 0 and 2 post-challenge. Animals were examined daily for signs of EAE and rated for severity of neurological impairment on a 5 point scale as previously described (Segal, B. M., and Shevach, E. M. 1996. *J Exp Med* 184:771-775).

Induction of EAE by Adoptive Transfer.

131. SJL mice were immunized with 100 µg of $PLP_{139-151}$ (SEQ ID NO: 1) emulsified in IFA (1:1) and C57BL/6 mice were immunized with $MOG_{35-55}$ in CFA (1:1) by the s.c. route as described above, but without injection of pertussis toxin. Twelve to fourteen days later draining LNs (inguinal and axillary) were removed and processed as previously described (Segal, B. M., et al. 2000. *J Immunol* 164:5683-5688). Cells were cultured in standard media with myelin peptide (50 µg/ml PLP or 25 µg/ml MOG) with or without murine rIL-12 (5 ng/ml; R&D Systems). At 96 h cells were harvested, washed and adoptively transferred into naïve syngeneic recipients (40-50×10⁶ cells i.p.). Recipient mice were examined daily and rated by observers blinded to treatment group or phenotype.

RNA Analysis.

132. Total RNA was extracted from whole spinal cords or isolated mononuclear cells using Trizol reagent (GIBCO BRL). Multiprobe RNase protection assays (RPA) were performed with the mCK-5b template sets, Riboquant In Vitro Transcription and RPA Kits (PharMingen). Riboprobe templates for CCL19, CCL21, and CXCL13 were obtained from Torrey Pines Biolabs, Inc. (Houston, Tex.); the template for Cyclophilin was from Ambion. RPA products were resolved on a denaturing polyacrylamide gel and quantified by Phosphorimaging. For RT-PCR, 2.5 µg of total RNA was reverse transcribed using random hexamer primers and M-MLV reverse transcriptase (GIBCO-BRL). cDNA was amplified using the following primer pairs (forward, reverse, and product size): CXCL13, TGAGGCTCAGCACAGCAACG (SEQ ID NO: 4) and CTTGAGCATTCCCTCTCAGCT (SEQ ID NO: 5)(537 bp); CCL19, CTGCCTCAGATTATCTGCCAT (SEQ ID NO: 6) and GCCAGAGTGATTCACATCTCT (SEQ ID NO: 7) (371 bp); CXCR5, ATGAACTACCCAC-TAACCCTG (SEQ ID NO: 8) and AGGTGAACCAG-GCTCTAGTTT (SEQ ID NO: 9) (658 bp); CCR7, GTGCTGGTGGTGGCTCTCCTTGTC (SEQ ID NO: 10) and CGTGTCCTCGCCGCTGTTCTTC (SEQ ID NO: 11) (594 bp); Class II transactivator form 1 (CIITA-I), GTGAT-GCCCTGGCCCGGAAGATTT (SEQ ID NO: 12) and TCGGGGAGACTGGGGATACTGAGG (SEQ ID NO: 13) (766 bp); CD3δ, GGGAGCCCCTTCAAGATACAAGT-GACC (SEQ ID NO: 14) and CGGGGCCAGTTCCCTC-CAAGAC (SEQ ID NO: 15) (452 bp); mb-1, GCCAGGGGGTCTAGAAGC (SEQ ID NO: 16) and TCACTTGGCACCCAGTACAA (SEQ ID NO: 17) (308 bp); Lysozyme M, CAGGCCAAGGTCTATGAACG (SEQ ID NO: 18) and ATTGTATGGCTGCAGTGATGTC (SEQ ID NO: 19) (289 bp); HPRT, GTTGGATACAGGCCA-GACTTTGTTG (SEQ ID NO: 20) and GAGGGTAGGCTG-GCCTATAGGCT (SEQ ID NO: 21) (353 bp).

Western Blot Analysis.

133. The assay was performed following published protocols (Luther, S. A., et al. 2002. *J Immunol* 169:424-433). Briefly, spinal cord tissue was pooled from 10 mice and homogenized in ice-cold lysis buffer (0.1M Tris-HCl (pH 8.0), 0.5 M EDTA, 60 mM CHAPS, Protease inhibitor cocktail (Sigma), at 1:50). Debris was removed by centrifugation (100,000 g for 1 hour), and supernatant was immunoprecipitated using heparin-Sepharose. Detection was with goat anti-mouse CCL19, CCL21, CXCL13 antibodies (R&D Systems), followed by antigoat HRP (Jackson ImmunoResearch Laboratories). The bands were visualized using chemiluminescence (PIERCE Super Signal West Femto substrate). Positive controls included protein extract from spleen, and recombinant chemokine proteins (R&D Systems).

Isolation of Spinal Mononuclear Cells.

134. Mice were anesthesized with Avertin and perfused with PBS by the intracardiac route using a peristaltic pump. Intact vertebral columns were removed by gross dissection and cords were ejected under the pressure of an HBSS-filled syringe. Spinal cord tissue was then minced into small fragments and digested with collagenase (2 mg/ml; CLS-4, Worthington Biochemical Corporation) and DNAse (1 mg/ml; DN25, Sigma). Mononuclear cells (MNCs) were isolated over a 30%/70% Percoll gradient (Pharmacia Biotech AP, Uppsala, Sweden) using standard protocols.

Enrichment of CD11c+ Cells.

135. CD11c+ cells were enriched from spinal cord MNCs using αFITC-coated magnetic beads following staining with FITC-conjugated anti-CD11c monoclonal antibody (Miltenyi).

Flow Cytometric Analysis.

136. Spinal cord MNCs were incubated with "FcBlock" and stained with various combinations of fluorochrome-labeled antibodies to mouse CD4, CXCR5, CD11c, CD11b, IgM, iCOS, CD44, and CD62L or with isotype-matched controls (Pharmingen). Cells were washed twice and fixed with 1% paraformaldehyde in PBS prior to analysis on a Becton-Dickinson FACS Calibur instrument with CellQuest software.

Histopathological Studies.

137. Spinal cords were dissected from mice following intracardiac perfusion with 4% paraformaldehyde. They were then decalcified in Immunocal and fixed in 10% buffered formalin. Paraffin-embedded sections of the cervical, thoracic and lumbar regions were stained with H&E, Trichrome or Luxol fast blue-periodic acid Schiff (LFB-PAS) for light microscopy. To identify T-cells, selected sections were stained with mouse anti-human CD3; detection was with the EnVision+ System (all reagents from DAKO Cytomation). Astrocytes were labeled with rabbit anticow GFAP (DAKO) followed by biotinylated goat anti-rabbit IgG (Vector), Streptavidin-HRP and AEC (Jackson). Macrophages and activated microglia were identified by biotinylated *Ricinus Communis* agglutinin (RCA) I (Vector).

Lymphoproliferation and Cytokine Secretion Assays.

138. LN cells ($4\times10^5$ in 0.2 ml) or splenocytes ($2\times10^5$ in 0.2 ml) were cultured with or without myelin peptide in quadruplicate for 4 days in 96 well flat-bottom plates (Costar, Cambridge, Mass.). Wells were pulsed for the final 16 hours of culture with 1 µCi [3H]TdR (NEN), and incorporated radioactivity was measured with a Betaplate scintillation counter (Wallac, Gaithersburg). For cytokine measurements by ELISA, splenocytes were cultured in 24 well plates ($5\times10^6$ cells/2 ml/well) for 72 hours. Supernatants were collected and analyzed using the OptEIA Mouse IFNγ set (Pharmingen). ELISPOT assays were performed as previously described (Kawakami, N., et al. 2004. *J Exp Med* 199:185-197).

Results

CXCL13 is Expressed in the CNS During Acute EAE.

139. CXCL13 mRNA was detected in the target organs of autoantibody associated autoimmune diseases such as Sjogren's syndrome and experimental systemic lupus erythematosis (Ishikawa, S., et al. 2001. *J Exp Med* 193:1393-1402, (Salomonsson, S., et al. 2002. *Scan J Immunol* 55:336-342). It was questioned whether the chemokine is also upregulated in the CNS of animals with EAE, a prototypical Th1-mediated autoimmune disease. Spinal cords were removed from B10.PL mice five weeks following immunization with MBP peptide in CFA. RNA was extracted from individual cords for RT-PCR analysis. CXCL13 mRNA was detected in every cord from animals with clinical EAE, but not in cords from naïve controls or from one MBP-primed mouse that remained asymptomatic at the time of sacrifice (FIG. 1a). CXCR5 mRNA was present in the CNS of some symptomatic mice. By comparison, mRNA encoding the lymphoid chemokine CCL19 and its receptor CCR7 was expressed at low levels in cords of naïve mice and at higher levels following disease onset. In synchrony with CXCL13, markers indicative of T-cell (CD3δ, dendritic cell (CIITA form I) and myeloid cell (lysozyme M) accumulation were detected.

Myelin-reactive Lymph Node Cells Induce CXCL13 Expression in the CNS in the Absence of Adjuvants.

140. Microbial products, such as heat killed *M. tuberculosis* in CFA, can modulate the expression of cytokines in the CNS even when administered systemically. Although CXCL13 was not detected in the spinal cords of control mice immunized with PBS in CFA, whether myelin-specific T-cells alone are sufficient to upregulate CXCL13 expression in the CNS was determined.

141. It was previously shown that LN cells from SJL mice immunized with an emulsion of $PLP_{139-151}$ peptide in IFA (without *Mycobacteria*) transfer EAE following in vitro stimulation with a combination of antigen and recombinant IL-112. The same LN cells are not encephalitogenic if IL-12 is omitted from the culture. Using this experimental system it was found that spinal cords from mice that had been injected with PLP/IFA primed, PLP/IL-12 reactivated cells 10-12 days earlier universally expressed CXCL13 and CXCR5 transcripts (FIG. 1B). By contrast, spinal cords harvested on the same day from healthy control mice, injected with cells that had been reactivated with PLP only, failed to express CXCL13 and CXCR5. The appearance of CXCL13 in the CNS was associated with upregulation of the T-cell, B cell, and dendritic cell markers (CD3δ, mb-1, and CIITA form I, respectively).

CXCL13 is Expressed on the Protein, as Well as the mRNA, Level in Inflamed Spinal Cords.

142. In order to determine whether CXCL13 mRNA correlates with protein expression Western blot analyses was performed on pooled spinal cord tissues from adoptive transfer recipients with EAE. CXCL13 protein was readily detectable in inflamed spinal cords but not in spinal cords from naïve controls (FIG. 1C). Similar results were obtained with regard to CCL19. On the other hand, CCL21 protein was constitutively expressed in the CNS in the absence of inflammation, possibly reflecting a role of that chemokine in homeostatic lymphocyte trafficking through the CNS.

CNS CXCL13 Levels Rise Progressively During the Course of Relapsing EAE.

143. Having demonstrated that CXCL13 is expressed in the CNS during acute EAE, CXCL13 expression was measured during the course of relapsing-remitting disease using RPA. SJL mice were actively immunized with PLP/CFA and representative animals were sacrificed during the presenting episode, remission and relapse for spinal cord harvest and RNA extraction. As shown in FIG. 2a, CXCL13 levels rose steadily over the course of the disease. CXCL13 mRNA was not detectable in cords from naïve mice, as confirmed by RT-PCR and southern blot hybridization. CCL19 and CCL21 followed similar kinetics to CXCL13. By contrast, CNS expression of the "inflammatory" chemokines MIP-1α, MIP-2 and RANTES were highest during the initial exacerbation, fell during remission and increased modestly during relapse (FIG. 2b). These results indicate that inflammatory chemokines are dominant during the first presentation of EAE, while CXCL13 is involved in the progression of chronic/relapsing disease.

CXCR5+ Cells Accumulate in EAE Infiltrates.

144. CXCL13 is the ligand for CXCR5, a receptor expressed by B cells, recently activated T-cells and follicular helper CD4+ T-cells (Kim, C. H., et al. 2001. *J Exp Med.* 193:1373-1381, Forster, R., et al. 1996. *Cell* 87:1037-1047, Ansel, K. M., et al. 1999. *J Exp Med.* 190:1123-1134). The RT-PCR data shown in FIG. 1a, b indicated that CXCR5+ cells infiltrate the CNS in association with the induction of CXCL13. This was corroborated by flow cytometric analyses of spinal cord MNCs. CXCR5+ cells were readily detected in the inflamed CNS of afflicted mice irrespective of the method of EAE induction or the stage of disease at sacrifice. The vast majority of CXCR5+ cells were CD4+CD3+ T-cells expressing an effector memory phenotype (CD62Llo, CD44hi, iCOShi). The relative percentage of CXCR5+ cells within the CD4+ T-cell compartment tended to increase during successive stages of relapsing disease in SJL mice. Although IgM+ B cells, which universally express CXCR5, could be found among the CNS infiltrating cells, they were present in sparse numbers.

145. Interestingly, a small population of CD4+CD3− cells in spinal cord mononuclear fractions (FIG. 3a, right panel) was also consistently detected. The majority of these cells expressed IL-7Rα, and a percentage expressed CXCR5. The cell surface phenotype CXCR5+IL-7Rα+CD4+ CD3− is suggestive of lymphoid tissue inducer cells, a unique subset of hematopoetic cells implicated in the development of lymph nodes, Peyer's patches and nasal-associated lymphoid tissue during embryogenesis (Luther, S. A., et al. 2003. *J Exp Med.* 197:1191-1198, Finke, D., et al. 2002. *Immunity* 17:363-373).

CXCL13 mRNA is Detected in CD11c+ Spinal Cord Mononuclear Cells.

146. CXCL13 is produced by stromal cells in spleen and lymph nodes. In addition, CXCL13 is secreted by some hematopoetic cells. Thus, murine peritoneal macrophages constitutively express CXCL13 (Ansel, K. M., et al. 2002. *Immunity* 16:67-76). Furthermore, myeloid dendritic cells isolated from the thymus and kidneys of mice with experimental lupus were found to express CXCL13 (Ishikawa, S., et al. 2001. *J Exp Med* 193:1393-1402).

147. In order to investigate whether hematopoetic cells are also the source of CXCL13 in the CNS, spinal cord MNCs were isolated from mice with EAE for RT-PCR analysis. During acute EAE CNS-infiltrating cells are comprised primarily of myeloid cells, including a significant subset expressing the dendritic cell marker, CD11c (FIG. 4a). Lymphoid cells, most of which are CD4+ T-cells, are also present (FIG. 3a). mRNA encoding CXCL13 was repeatedly detected, as well as CCL19 and CCL21, in this mixed leukocyte population isolated from SJL mice during either the first or second episode of EAE (FIG. 4a). Similar results were obtained from MOG-sensitized C57BL/6 mice during their initial clinical presentation (FIG. 4b). By contrast, CXCL13 was not detectable in MNCs isolated from the spinal cords of naïve mice, which are dominated by CD11blo cells (resident microglia) and lack a CD11c+ cell population. CXCL13 transcripts were enriched in MACS-isolated CD 11c+ cells (FIG. 4c), indicating that dendritic cells might be a major source of the chemokine in the inflamed CNS.

Actively Immunized CXCL13 Deficient Mice Experience a Relatively Mild Course of EAE and Do Not Experience Relapses.

148. In order to assess the physiological significance of CXCL13 in EAE C57BL/6 CXCL13−/− and wildtype mice were immunized with MOG peptide in CFA and monitored their clinical courses. CXCL13 deficient mice exhibited a significant decrease in disease severity during the presenting episode, recovered more fully and were free of relapses by comparison to their wildtype counterparts (FIG. 5a, Table 1).

TABLE I

Course of EAE induced by active immunization in CXCL13$^{-/-}$ and WT mice

|  | CXCL13$^{-/-}$ | WT | P$^a$ |
|---|---|---|---|
| Incidence | 43/55 | 52/67 | P = 1.0 |
| Disease course: |  |  | P < 0.0001 |
| monophasic | 36 | 13 |  |
| relapsing or chronic | 7 | 39 |  |

Summary of 4 experiments.
$^a$Fisher's exact test two-sided P value.

Figure 6:
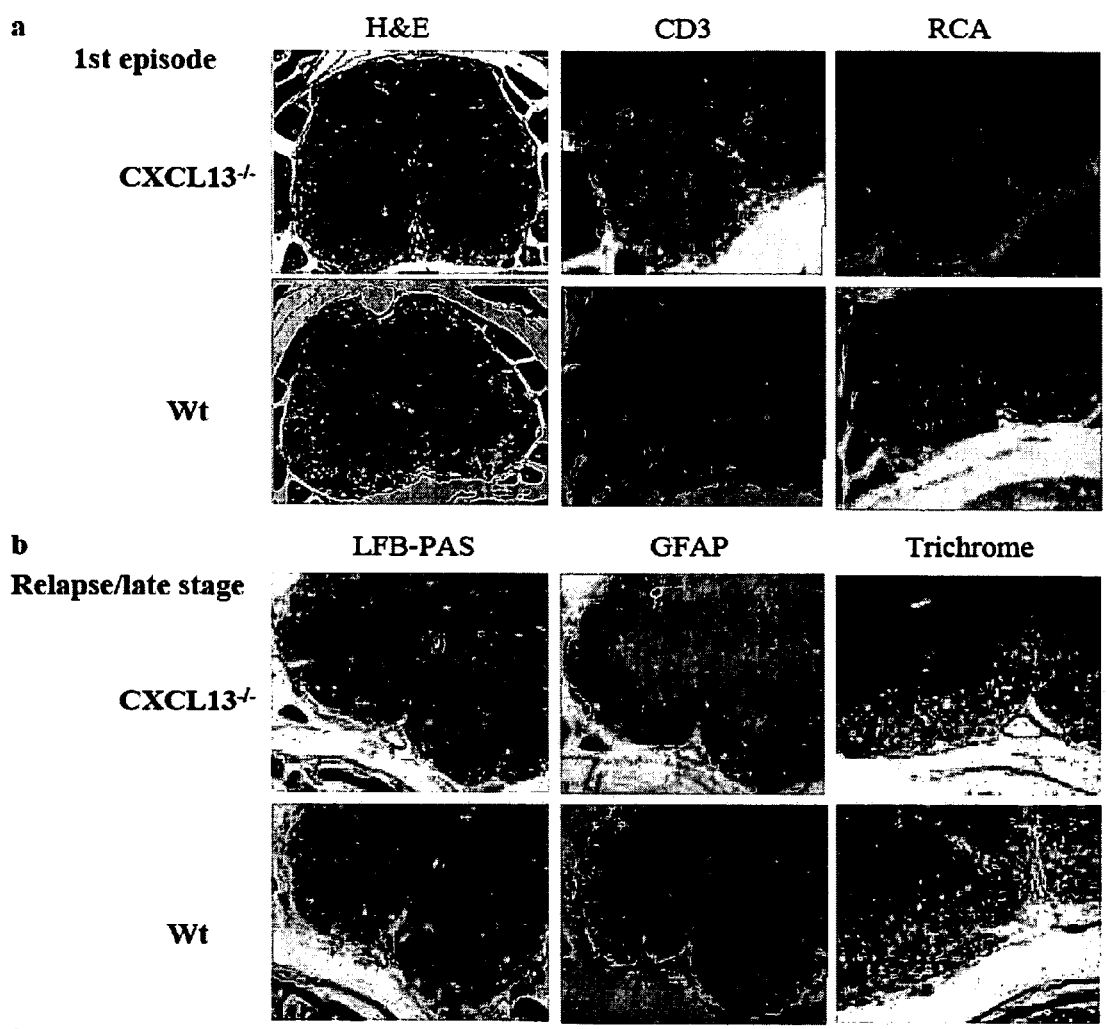
FIG. 6 shows that CXCL13−/− mice with EAE exhibit relatively mild histopathological changes in the CNS. Spinal cord sections from C57BL/6 CXCL13−/− and wildtype mice sacrificed during the first exacerbation (a) or later stages (b) of EAE were fixed in paraformaldehyde, embedded in paraffin and stained with the indicated reagents. Representative sections are shown. Original magnification: ×4 for H&E; ×10 for all other stains.

149. During the first exacerbation, the degree of inflammation and demyelination in individual mice correlated closely with the clinical score. In CXCL13−/− mice inflammatory infiltration and demyelination were restricted, in large part, to the subpial regions (FIG. 6a, H&E). By contrast, wildtype mice exhibited more extensive involvement of all white matter tracts. Macrophages and activated microglia, identified by the lectin RCA, were less numerous in white matter lesions of CXCL13−/− mice. On the other hand, there was no apparent difference in the degree of CD3+ T-cell infiltration between the two groups (FIG. 6a).

150. The difference in demyelination (loss of blue staining) and inflammatory cell infiltration between the groups was even more pronounced during later stages (day 32 after immunization), when wildtype mice were in relapse, while CXCL13−/− mice remained in remission (FIG. 6b, LFB-PAS). Furthermore, lesions in wildtype mice were characterized by a prominent degree of gliosis (indicated by GFAP staining) and intrameningeal and subpial fibrosis (Trichrome), whereas CXCL13−/− mice showed only mild changes.

Figure 7:
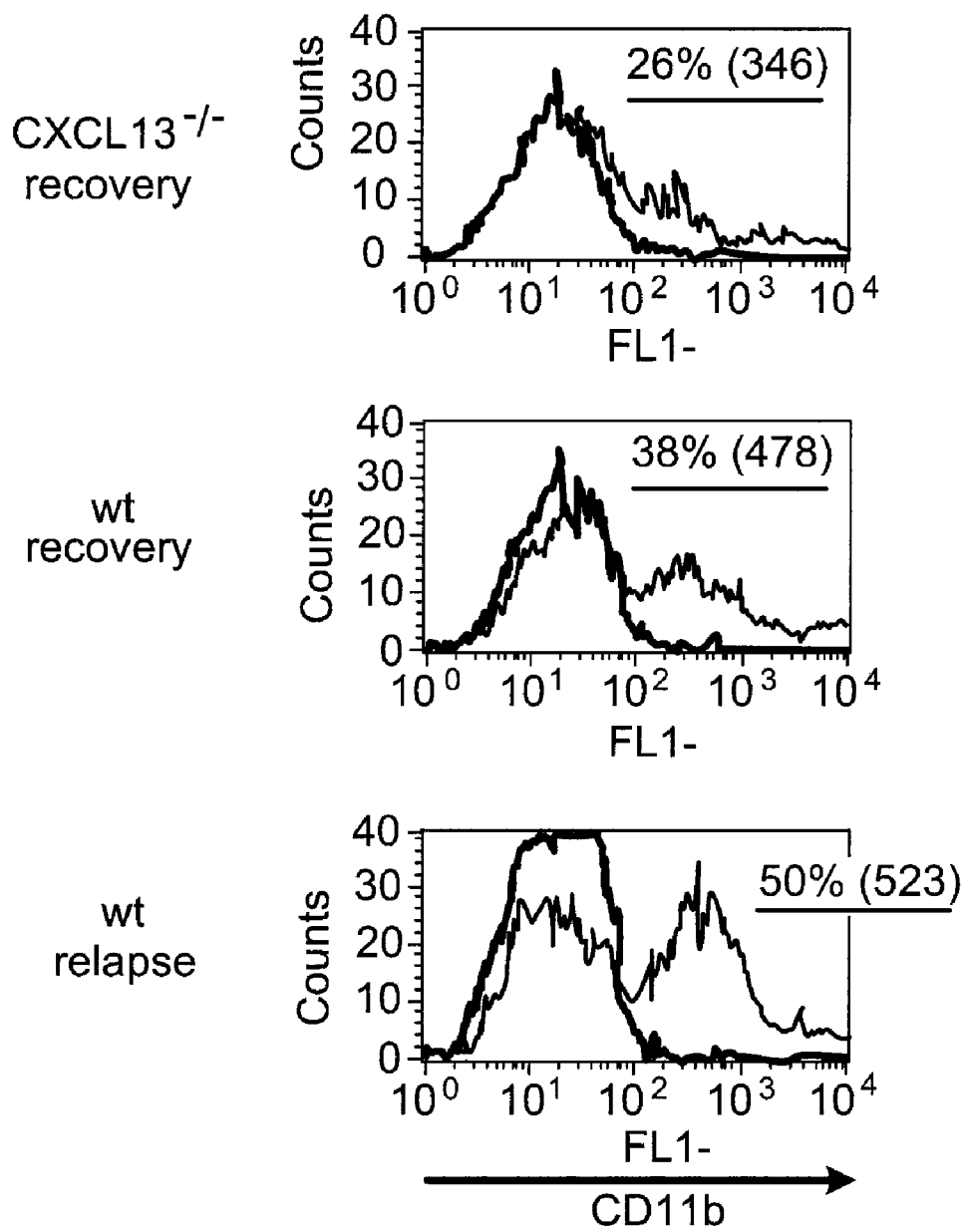
FIG. 7 shows that CD11b+myeloid cells are disproportionately depleted in CNS infiltrates of CXCL13−/− mice. C57BL/6 wildtype and CXCL13−/− mice were immunized with $MOG_{35-55}$. Spinal cord MNCs were isolated during EAE relapse or remission for FACS analysis. Cells were stained with αCD11b (filled histogram) or isotype control (solid line) antibodies. The percentage of CD11b+ cells and median flouresence intensity (MFI) are shown.

151. Flow cytometric analysis of spinal cord MNCs from symptomatic CXCL13−/− mice demonstrated a reduced percentage of CD11b+myeloid cells by comparison to wildtype mice. This was most notable during the recovery phase following acute EAE (FIG. 7). A relative paucity of CNS-infiltrating macrophages in CXCL13−/− mice might partially account for the milder white matter damage that these animals experience. A lower number of MNCs per spinal cord was consistently isolated from CXCL13−/− than from wildtype mice, at all stages of disease (between 20-60% lower, depending on stage). However, there was no major difference in the composition of the lymphoid cell population, and a lower percentage of CXCR5+cells in spinal cord MNCs from CXCL13−/− versus wildtype mice was not documented. Therefore, while the absolute number of CNS-infiltrating T-cells/cord was generally lower in CXCL13−/− mice, T-cells were not preferentially depleted.

Peripheral Myelin-specific T-cell Responses are Comparable in CXCL13 Deficient and Wildtype Mice.

152. CXCL13 deficient mice exhibit impaired lymphoid organogenesis, with a paucity of Peyer's patches and most lymph nodes and disorganized splenic architecture (Ansel, K. M., et al. 2000. *Nature* 406:309-314, Luther, S. A., et al. 2003. *J Exp Med*. 197:1191-1198, Moser, B., and Loetscher, P. 2001. *Nature Immunology* 2:123-128, Cyster, J. G. 1999. *Science* 286:2098-2102). Although CXCL13−/− mice are not grossly immunodeficient, their relative resistance to induction of EAE could potentially be related to the failure of autoreactive T-cells to undergo priming in the periphery. To investigate that, myelin-specific proliferative and cytokine responses by splenocytes harvested from CXCL13 deficient and wildtype mice were measured following active immunization with MOG peptide. Comparable frequencies of MOG-specific IL-2 producing cells were found in CXCL13−/− and wildtype mice. CXCL13−/− mice also mounted significant lymphoproliferative and IFNγ responses upon challenge with antigen in vitro (Table 2). Collectively this data indicates that MOG-specific CD4+ T-cells undergo priming, clonal expansion and differentiation in the absence of CXCL13.

TABLE 2

Splenic T-cell responses of sensitized CXCL13 knockout and wild type mice*

|  |  | CXCL13$^{-/-}$ | wt |  |
|---|---|---|---|---|
| Proliferation (cpm) | No stimulus | 3598 ± 348 | 3722 ± 1220 |  |
|  | MOG | 40856 ± 5123 | 8792 ± 3417 | p = 0.02 |
| IFNγ production (ng/ml) | No stimulus | 0.36 ± 0.09 | 0.57 ± 0.13 |  |
|  | MOG | 16.21 ± 0.82 | 20.30 ± 3.44 | p = 0.06 |
|  | Con A | 23.49 ± 3.35 | 36.68 ± 1.32 | p = 0.02 |

TABLE 2-continued

Splenic T-cell responses of sensitized CXCL13 knockout and wild type mice*

|  |  | CXCL13$^{-/-}$ | wt |  |
|---|---|---|---|---|
| Frequency of IL-2 producers (per 5 × 105 cells) | No stimulus | 9 | 10 |  |
|  | MOG | 94 ± 2 | 112 ± 9 | p = 0.12 |

*MOG-specific CD4+ T-cell responses were measured by tritiated thymidine incorporation (proliferation), ELISA (IFNγ) and elispot (IL-2). The results shown represent an average of 3 mice/group +/− standard deviation. Groups were compared using the Student's T-test.

CXCL13 Deficiency or Blockade Attenuates Adoptively Transferred EAE.

153. Based on the above results it was speculated that CXCL13 plays a non-redundant role during the effector stage of EAE, at a point beyond peripheral T-cell priming. Next, the clinical EAE was compared in chemokine deficient and sufficient mice following the adoptive transfer of MOG/IL-12 stimulated LN cells from MOG/CFA primed, chemokine sufficient donors. CXCL13 recipients underwent a milder course of EAE, with delayed onset and accelerated and more complete recovery (FIG. 5b).

154. Immunological studies in knock-out mice are potentially subject to artifacts consequent to compensatory pathways that develop in response to the life-long deficiency of a particular cytokine or chemokine. Therefore, the effects of CXCL13 neutralization on adoptively transferred EAE in immunocompetent SJL recipients were also tested. SJL mice were treated with a neutralizing goat anti-mouse CXCL13 antibody, isotype matched control antibodies or PBS on days 3, 6 and 10 post cell transfer. As shown in FIG. 5c, the animals treated with anti-CXCL13 were protected from EAE.

CXCL13 Deficient Mice can Generate Myelin-reactive Encephalitogenic T-cells that Initiate CNS Inflammation 155. CXCL13 deficient mice exhibit impaired lymphoid organogenesis, with a paucity of Peyer's patches, lymph nodes and disorganized splenic architecture. Although these mice are not grossly immunodeficient, it was important to determine whether they could mount a myelin-specific T-cell response sufficient to initiate CNS inflammation.

Figure 12:
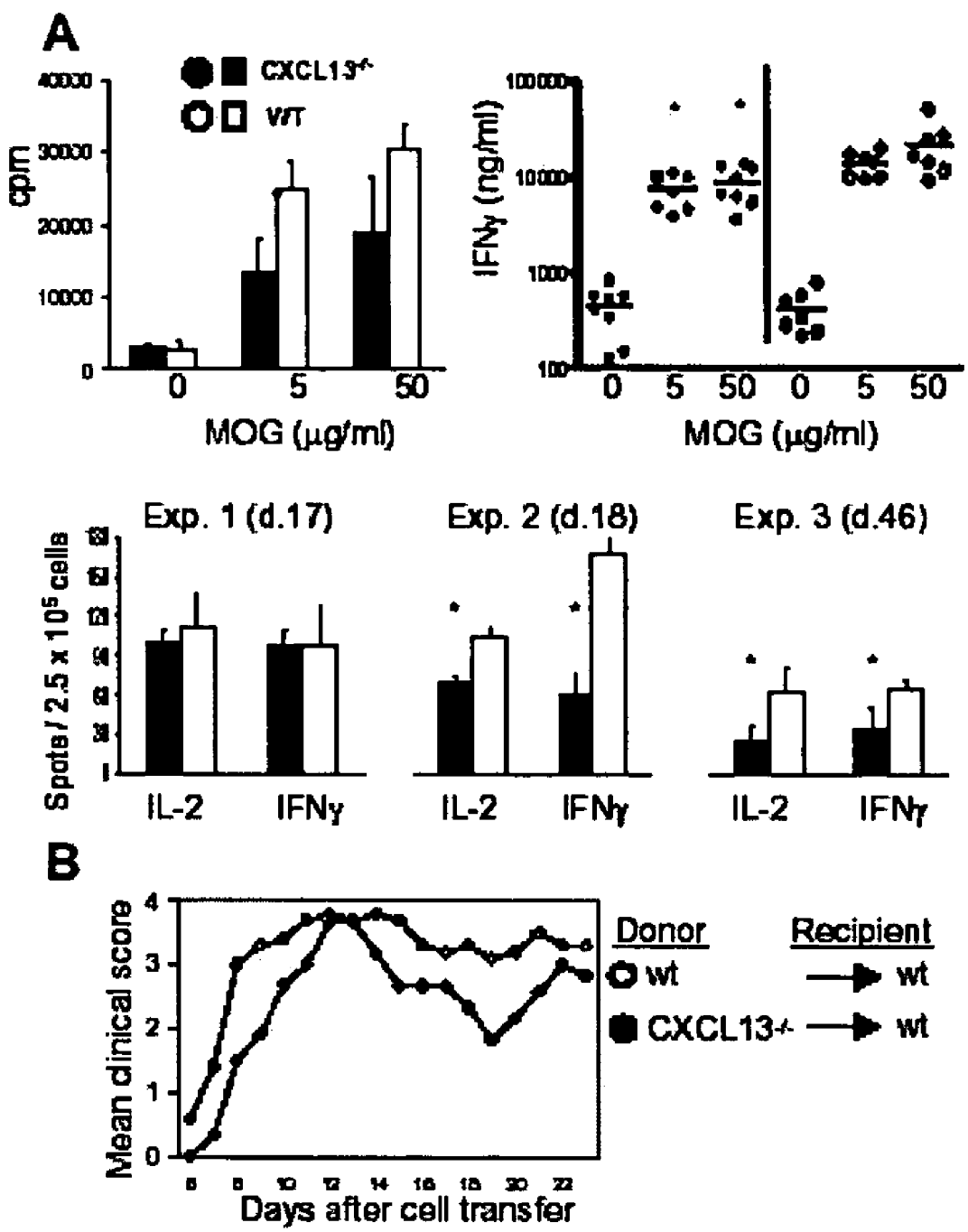
FIG. 12 shows that CXCL13−/− mice generate myelin reactive encephalitogenic T-cells that initiate CNS inflammation.

156. Splenocytes harvested from CXCL13−/− mice immunized with MOG$_{35-55}$ in CFA mounted significant proliferative, IL-2 and IFN-g responses upon challenge with peptide in vitro (FIG. 12A). LN cells, though scarce in CXCL13−/− mice, also proliferated vigorously and secreted IFN-g in an antigen-specific manner. Spleens from immunized CXCL13−/− mice generally contained a lower frequency of IL-2 and IFN-g producing cells (on average 2 to 3-fold) than WT spleens (FIG. 12A, lower panel, Exp. 2). Nevertheless, individual responses varied, with some CXCL13−/− mice showing comparable cytokine production to WT mice (Exp. 1). MOG-specific memory T-cells persisted in spleens of CXCL13−/− mice as evidenced by IFN-g and IL-2 recall responses measured as late as day 46 after immunization (Exp. 3).

157. Next the ability of CXCL13−/− mice to generate encephalitogenic T-cells was assessed in adoptive transfer experiments. Splenocytes from MOG/CFA primed CXCL13−/− or WT mice were stimulated in vitro with MOG and IL-12 for 4 days, and then equal numbers of cells were injected into naïve WT recipients. Donor cells from both groups induced a severe and persistent form of EAE (FIG. 12B). However, recipients of CXCL13−/− effector cells underwent a slightly less aggressive course that was, nonetheless, statistically different from recipients of WT effector cells.

Adoptively Transferred EAE is Attenuated in CXCL13−/− Mice

158. Based on the observations that CXCL13 is upregulated in the CNS during EAE, it was speculated that it might play a distinct role during the effector stage of pathogenesis. Consequently, clinical EAE in CXCL13 deficient and sufficient mice was compared following the adoptive transfer of MOG specific CD4+ T-cells from WT donors (FIG. 5D). WT recipients injected with $5 \times 10^6$ CD4+ T-cells quickly progressed to severe EAE: 60% of mice died, and the surviving mice suffered conspicuous chronic deficits. By contrast, CXCL13−/− recipients underwent a significantly milder course of EAE with delayed onset, reduced mortality (28%) and accelerated recovery. The majority of mice enjoyed complete or near complete recovery. Similar results were obtained in two additional experiments using LN cells from primed WT donors.

Figure 13:
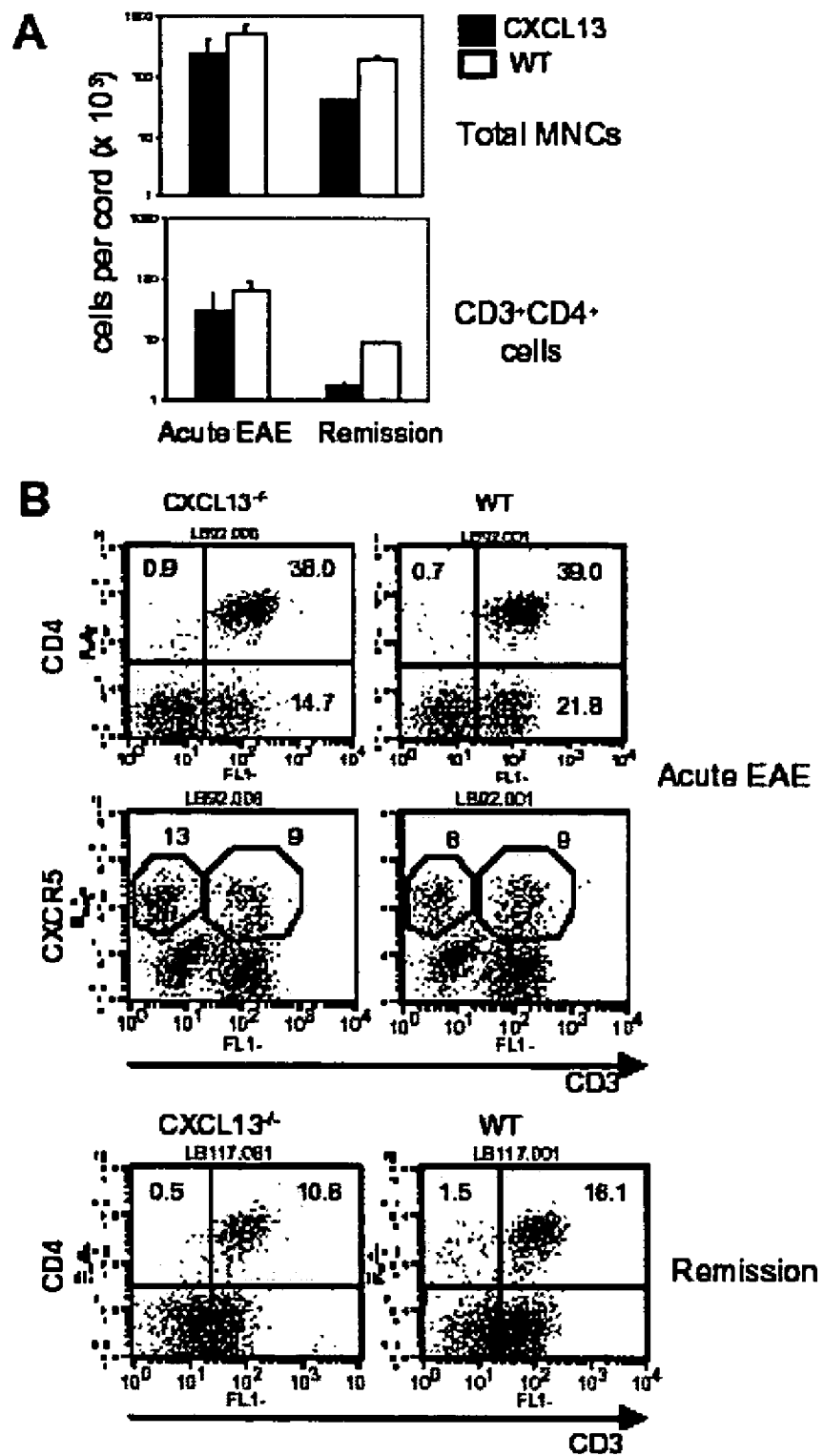
FIG. 13 shows that CNS-infiltrating T-cells are diminished in CXCL13-deficient mice during late stages of EAE. C57BL/6 CXCL13−/− and WT mice were immunized with $MOG_{35-55}$/CFA. FACS analysis of pooled CNS MNCs was performed during the 1st episode of EAE (days 15-21), or during remission (day 42).

Inflammatory CNS Infiltrates are Diminished in CXCL13−/− Mice, Particularly During Chronic Stages of EAE 159. In order to investigate whether CXCL13 deficiency had influenced the recruitment and retention of leukocyte subsets in the CNS, MNCs from WT and CXCL13−/− spinal cords were isolated during early and late stages of EAE and were analyzed by flow cytometry. CXCL13−/− mice consistently yielded fewer mononuclear cells per spinal cord than WT mice (FIG. 13A). During the first exacerbation the cell yield from pooled CXCL13−/− cords was 30% to 50% lower that from WT cords. The number of CNS MNCs fell dramatically between the presenting episode of EAE and the subsequent remission in both groups. However, the decline was more pronounced in CXCL13−/− mice, which yielded 4 to 5 fold fewer spinal cord MNCs than their WT counterparts during remissions.

160. During acute EAE, there was no major difference in the subset composition of infiltrating cells. In particular, the percentages of CD4+ T-cells were comparable in CXCL13−/− and WT infiltrates (FIG. 13B), and these cells uniformly expressed CD44 and ICOS, indicative of an activated state. Percentages of myeloid cells (including $CD45^{hi}CD11b^{hi}$ monocytes/macrophages and CD11c+DCs) and CD4-CD3+ cells (primarily CD8+ T-cells) were moderately reduced in CXCL13−/− CNS infiltrates (FIGS. 13B and 14A).

Figure 14:
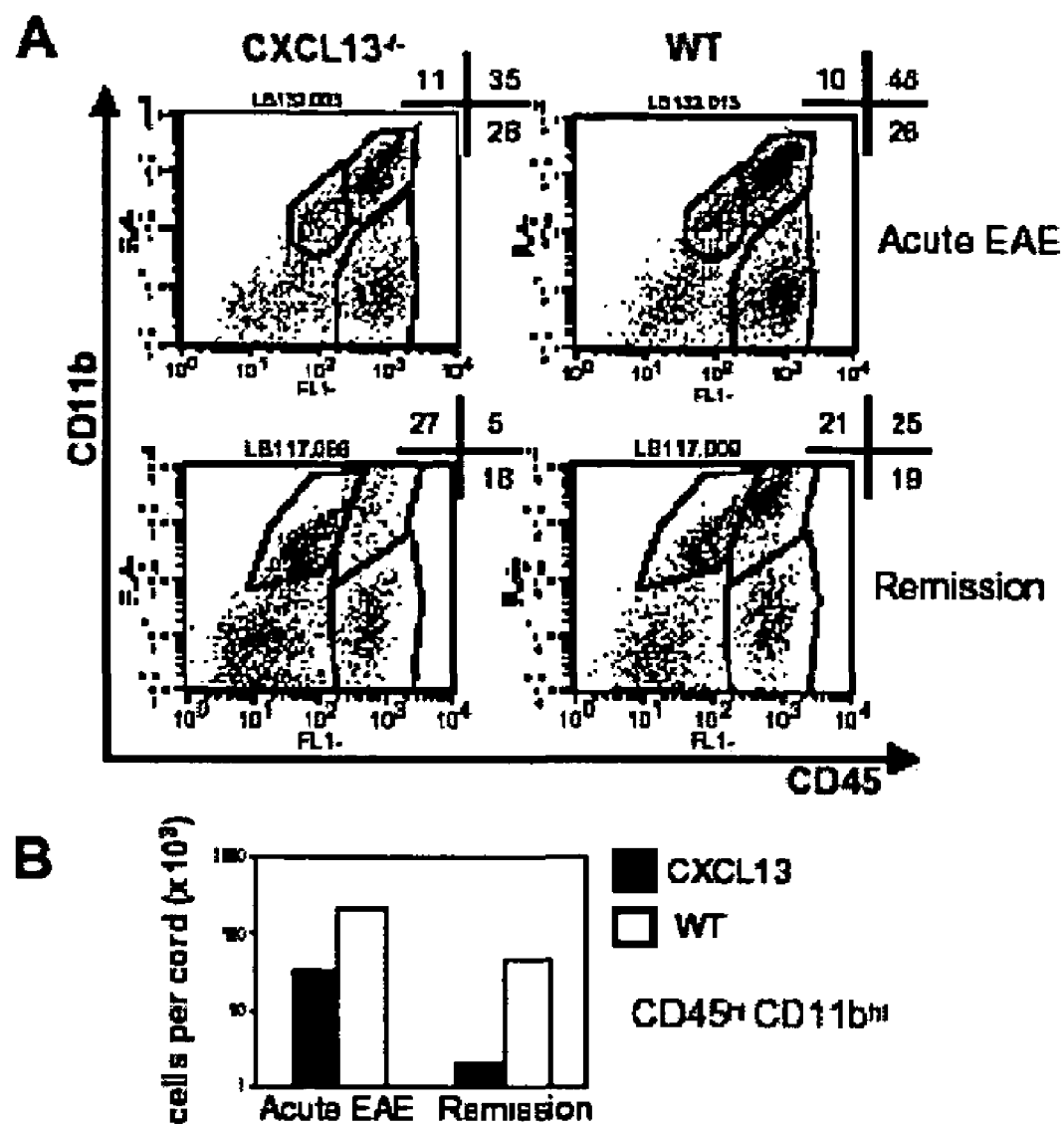
FIG. 14 shows that myeloid cells are disproportionately depleted in CNS infiltrates of CXCL13−/− mice during late stages of EAE. C57BL/6 WT and CXCL13−/− mice were immunized with $MOG_{35-55}$/CFA. Spinal cord MNCs were isolated during the 1st episode or remission of EAE for FACS analysis.

161. The percentage of CD4+ T-cells among infiltrating leukocytes remained comparable between the groups at remission. Hence, the absolute number of infiltrating CD4+ T-cells was 4 to 5 fold lower in CXCL13−/− cords, in direct proportion to the relative reduction in total MNCs (FIG. 13A). On the other hand, monocytes/macrophages were disproportionately depleted in spinal cords of CXCL13−/− mice during late stages of disease, such that the absolute number of $CD45^{hi}CD11b^{hi}$ cells was, on average, 18 fold lower in CXCL13−/− than in WT cords (FIG. 14). A similar trend was observed with respect to CD11c+ cells.

162. Interestingly, CXCR5 was expressed on similar percentages of CNS-infiltrating cells in CXCL13−/− and WT mice. At peak disease, 10-20% of both CD4+ and CD4− T-cells were CXCR5+ irrespective of host genotype. Furthermore, the cellular composition of CXCR5+ cells did not differ. In both groups, approximately 50% of CXCR5+ cells were CD3+ T-cells, and the other 50% included B cells, NK cells, and a subset of myeloid cells.

Discussion

Figure 2:
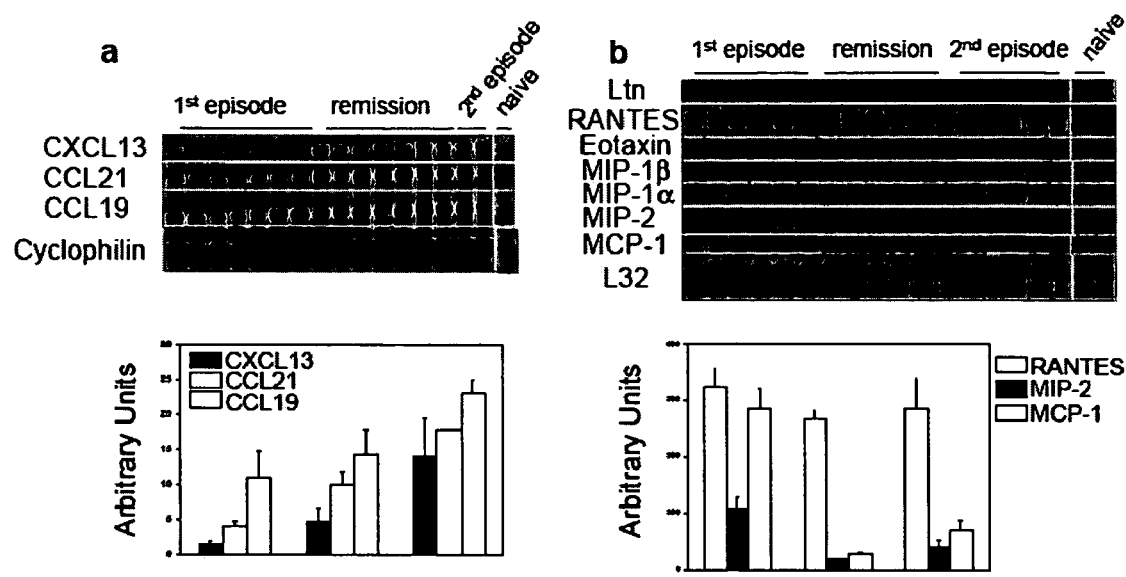
FIG. 2 shows that lymphoid chemokine expression rises steadily in the CNS during the course of relapsing-remitting EAE. By contrast, inflammatory chemokine levels fluctuate in concert with clinical score. SJL mice were immunized with $PLP_{139-151}$/CFA. Representative animals were sacrificed during successive stages of relapsing EAE for analysis of lymphoid (a) and inflammatory (b) chemokines by RPA. Chemokine levels were quantified by phosphorimaging (lower panels). The results shown are representative of 2 independent experiments.

163. Herein it was demonstrated for the first time that the lymphoid chemokine CXCL13 plays a pathogenic role in EAE, a Th1-mediated, organ specific autoimmune disease. CXCL13 first appears in spinal cords of affected mice during the presenting episode and its levels rise steadily as the disease progresses (FIGS. 1, 2). The experiments with CXCL13 deficient mice, as well as with wildtype mice treated with anti-CXCL13 neutralizing antibodies, demonstrate that the chemokine contributes to disease severity within days of symptom onset. However, it also exerts significant effects during later stages, as reflected by the decreased rate of relapsing and chronic EAE in CXCL13−/− animals (FIG. 5a, Table 1). In corroboration with these clinical results, spinal cords from CXCL13−/− mice have relatively mild inflammatory infiltrates and contain a decreased percentage of myeloid cells by comparison to their wildtype counterparts. Furthermore, pathological changes in CXCL13 deficient mice are confined, in large part, to the subpial white matter, whereas multiple deep white matter tracts are affected in wildtype mice.

164. The finding that the lymphoid chemokines, CXCL13, CCL21 and CCL19 are upregulated in the inflamed CNS of mice with EAE is supported by several recent publications from other laboratories. Magliozzi et al. reported that CXCL13 transcripts are elevated in the CNS of $PLP_{135-151}$-immunized SJL mice during exacerbations, although not during remissions (Magliozzi, R., et al. 2004. *J Neuroimmunol* 148:11-23). By contrast, it was found that CXCL13, CCL21 and CCL19 levels rise steadily during disease progression, including the remission phase between the first and second exacerbations, as measured by quantitative RPA. Similar results were obtained in independent experiments using semi-quantitative RT-PCR. The discrepancy between the findings herein and those of Magliozzi and colleagues might be the result of methodological or sampling differences. Nonetheless, in all studies published thus far, CNS lymphoid chemokine levels were found to reach their height during relapsing or progressive stages of EAE, suggesting an association between disease chronicity and chemokine expression within the target organ (Alt, C., et al. 2002. *Euro J Immunol* 32:2133-2144, Columba-Cabezas, S., et al. 2003. *Brain Pathology* 13:38-51, (Magliozzi, R., et al. 2004. *J Neuroimmunol* 148: 11-23).

165. CXCL13 is produced by mesenchymal stromal cells in secondary lymphoid tissues (Cyster, J. G. 1999. *Science* 286:2098-2102). However, lymphoid chemokines can also be secreted by myeloid cells (Ishikawa, S., et al. 2001. *J Exp Med* 193:1393-1402, Ansel, K. M., et al. 2002. *Immunity* 16:67-76). The data pinpoint CD11b+CD11c+ myeloid cells as the cellular source of CXCL13, as well as CCL19 and CCL21, in the inflamed CNS. Consistent with these results, Columba-Cabezas and colleagues detected CCL19 in infiltrating leukocytes, which they suspected were macrophages and dendritic cells, in EAE lesions (Columba-Cabezas, S., et al. 2003. *Brain Pathology* 13:38-51). The findings do not exclude the possibility that non-hematopoetic cells also contribute to lymphoid chemokine production in the CNS during the course EAE. Based on the RT-PCR study shown in FIG. 4a it appears that CCL19 and CCL21 mRNA expression declines in spinal cord mononuclear cells between the first and second episode of relapsing disease, whereas levels of both chemokines rise in whole spinal cord tissues harvested at the same time points.

166. CXCL13 has a significant impact on the severity of inflammatory CNS demyelination and its clinical manifestations. Although lymphoid organogenesis is impaired in CXCL13−/− mice, their resistance to EAE cannot be attributed to a failure to activate autoreactive T-cells in the periphery. In fact, splenocytes from MOG-immunized CXCL13−/− mice mount significant antigen-specific IL-2 and IFNγ responses upon ex vivo challenge, indicating that autoreactive T-cell priming, clonal expansion and differentiation does occur in the absence of CXCL13. Furthermore, CXCL13 deficient mice develop less severe EAE than wildtype counterparts following the transfer of myelin-reactive T-cells that had been primed in chemokine-sufficient donors (FIG. 5b). In parallel experiments it was shown that αCXCL13 neutralizing antibodies suppress adoptively transferred EAE in highly susceptible SJL mice (FIG. 5c). Collectively, the data indicate that CXCL13 plays a unique role during the effector phase of the disease, by altering the biological activities of CNS infiltrating CXCR5+ cells.

167. The vast majority of CXCR5+cells in spinal cord infiltrates of mice with acute EAE are CD4+CD3+ T-cells. CXCR5+ B cells are present as well, but in sparse numbers. Although CXCL13 plays an indispensable role in the formation of organized B cell follicles in lymph nodes and spleen, the chemokine is not necessary for B or T-cell accumulation in these organs per se (Forster, R., et al. 1996. *Cell* 87:1037-1047, Ansel, K. M., et al. 1999. *J Exp Med.* 190:1123-1134). It was shown that CXCL13 alters the course of EAE by modulating the biological activities of CXCR5+ cells once they have infiltrated the CNS, rather than by attracting them across the blood-brain-barrier initially. Similar conclusions were reached regarding the effects of CXCL13 on CD4+CD3− lymphoid inducer cells during lymphoid organogenesis. While CD4+CD3− cells fail to induce Peyer's patches in CXCR5 deficient mice, they accumulate in large numbers in the mesenteric lymph nodes and spleen. However, in the absence of CXCL13 simulation the inducer cells fail to express an activated form of α4β1 integrin, which is necessary for interactions with stromal cells that lead to the induction of intestinal lymphoid tissues (Finke, D., et al. 2002. *Immunity* 17:363-373).

Figure 4:
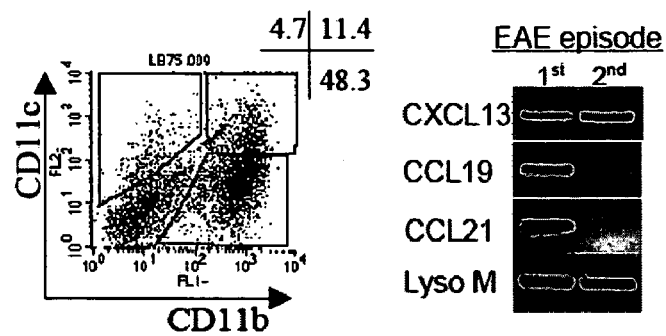
FIG. 4 shows that lymphoid chemokine transcripts are expressed in spinal cord mononuclear cells (MNCs) from mice with acute and relapsing EAE but not from naïve controls. Furthermore, CXCL13 mRNA is enriched in the CD11c+ subpopulation. In the experiment shown in FIG. 4(*a*) SJL mice were immunized with PLP/CFA. Spinal cords were harvested during the 1st and 2nd episodes of EAE, respectively, to isolate infiltrating MNC by Percoll gradient centrifugation. MNCs were used for flow cytometric analysis to characterize myeloid subsets and for extraction of RNA to measure expression of CXCL13, CCL19, CCL21 and lysozyme M (a myeloid cell marker) by RT-PCR.
Figure 4:
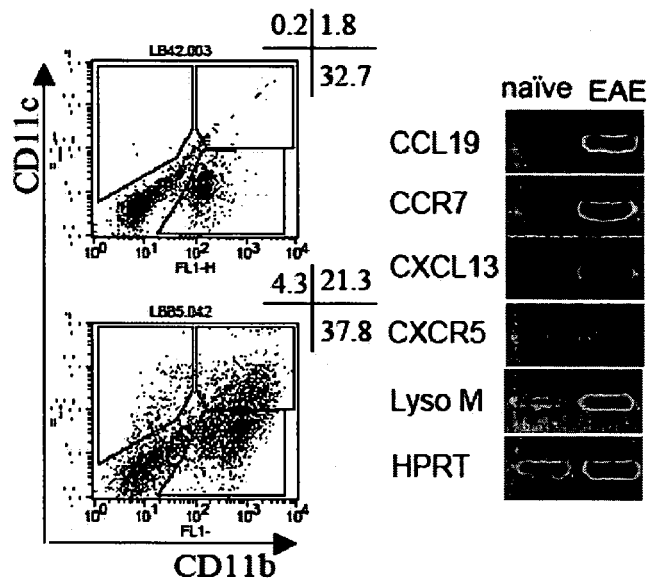
Figure 4:
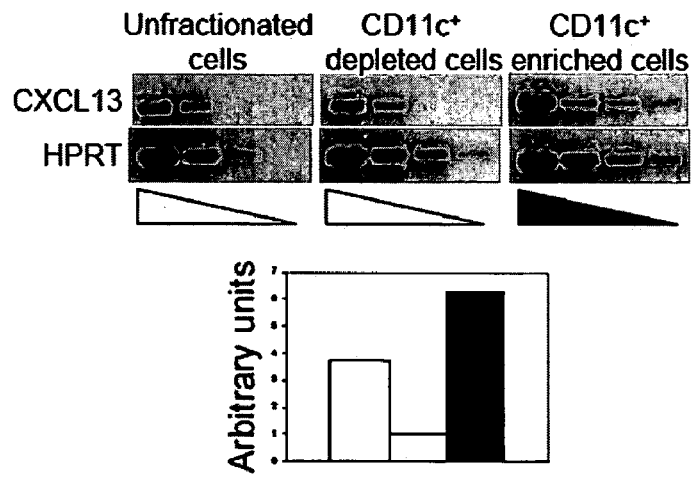

168. By analogy to its role in the organization of B cell follicles, it is shown herein that CXCL13 coordinates the positioning of myelin-specific T-cells in relationship to other leukocyte subsets within perivascular infiltrates in a manner that facilitates cognate cell-to-cell interactions. The data indicates that CXCL13 is produced by CD11b+ CD11c+ myeloid cells within the inflamed spinal cord (FIG. 4). Such cells could serve as APCs for reactivation of myelin-reactive T-cells following their passage across the blood-brain barrier. If so, a CXCL13 gradient could draw newly arrived CXCR5+ T-cells directly to APCs bearing myelin peptide/MHC Class II complexes, thereby facilitating T-cell reactivation in the target organ. A recent study underscored the importance of T-cell reactivation within the CNS for the production of monocyte chemoattractants, recruitment of macrophages and, ultimately, the clinical manifestation of EAE (Aloisi, F., et al. 2000. *J. Immunol.* 164:1705). Interestingly, the histopathological and FACS studies demonstrate impaired accumulation of macrophages in EAE lesions in CXCL13−/− mice, possibly reflecting insufficient reactivation of myelin-reactive T-cells.

169. CXCL13 might also facilitate collaborations between T and B lymphocytes within the CNS. Cognate T-B cell interactions are known to occur in the CNS of patients with MS, leading to antigen-driven B cell clonal expansion and antibody production in situ (Baranzini, S. E., et al. 1999. *J Immunol* 163:5133-5144, Correale, J., and de los Milagros Bassani Molinas, M. 2002. *J of Neurology* 249:375-389, Colombo, M., et al. 2000. *J Immunol* 164:2782-2789, Gerritse, K., et al. 1994. *J Neuroimmunol* 49:153-159). Magliozzi and colleagues identified lymphoid-follicle like structures containing B cells within the meninges of mice undergoing progressive and chronic-relapsing EAE (Magliozzi, R., et al. 2004. *J Neuroimmunol* 148:11-23). As has been proposed in other autoimmune models, CXCL13 might bring autoreactive T helper and B cells into close proximity to one another. Ultimately, this could result in the local production of pathogenic antibodies, which could facilitate demyelination (Cross, A. H., et al. 2001. *J Neuroimmunol* 112:1-14, Lyons, J. A., et al. 1999. *European J Immunol* 29:3432-3439, Genain, C. P., et al. 1995. *Journal of Clinical Investigation* 96:2966-2974).

170. In later phases of EAE, the pathogenic effects of CXCL13 might be realized through alternative routes. Previous publications have emphasized the potential role of CXCL13 in lymphoid neogenesis in animal models. Transgenic expression of CXCL13 under the rat insulin promoter results in the formation of lymph node-like structures in the pancreas characterized by lymphoid-myeloid aggregates, MAdCAM-1+ blood vessels and local induction of CCL21 (Luther, S. A., et al. 2000. *Immunity* 12:471-481). These same features have been observed in EAE and/or MS lesions and most likely participate in the perpetuation of chronic or relapsing CNS inflammation (Cross, A. H., et al. 1990. *Lab Invest* 63:162-170, Raine, C. S., et al. 1980. *Laboratory Investigation* 43:150-157, Raine, C. S., et al. 1984. *Laboratory Investigation* 51:534-546, Prineas, J. W., and Wright, R. G. 1978. *Laboratory Investigation* 38:409-421, Prineas, J. W. 1979. *Science* 203:1123-1125, Kanwar, J. R., et al. 2000. *J Neuroimmunol* 103:146-152, Alt, C., et al. 2002. *Euro J Immunol* 32:2133-2144, Columba-Cabezas, S., et al. 2003. *Brain Pathology* 13:38-51). Furthermore, CXCL13 is present in the synovial tissues of patients with rheumatoid arthritis and salivary glands of patients with Sjogren's syndrome in association with organized B-T-cell aggregates that resemble lymphoid follicles (Shi, K., et al. 2001. *J Immunol* 166:650-655, Salomonsson, S., et al. 2002. *Scan J Immunol* 55:336-342). With the current study, it was demonstrated that CXCL13 was induced in CNS tissues following infiltration by myelin-reactive T-cells.

171. During the formation of secondary lymphoid organs, CXCL13 stimulates CD4+CD3− lymphoid tissue inducer cells to express an activated form of α4β1 and membrane lymphotoxin-α1β2 (Finke, D., et al. 2002. *Immunity* 17:363-373) both of which are necessary for critical interactions with stromal cells. CXCR5+ IL-7Rα+CD4+CD3− cells were detected, indicative of lymphoid inducer cells, in EAE infiltrates.

172. The current study is the first to directly demonstrate a non-redundant role of CXCL13 in an organ-specific autoimmune disease. Furthermore, it introduces the concept that CXCL13 can participate in the pathogenesis of autoimmune conditions that are traditionally considered to be CD4+ Th1 cell driven, as well as in those primarily mediated by autoantibodies. The data indicate that agents that neutralize CXCL13 or block its receptor can be useful in the treatment of human autoimmune conditions, such as multiple sclerosis.

Example 2

Expression of Lymphoid Chemokine/Chemokine Receptor mRNA in Spinal Cords of Mice with EAE 173. To determine whether the lymphoid chemokines, CXCL13, CCL19, and CCL21 are expressed in the CNS during EAE, RT-PCR was performed on RNA extracted from spinal cords from symptomatic mice and naïve controls. B10.PL mice (n=5) were actively immunized with an immunodominant peptide of myelin basic protein ($MBP_{Ac1-11}$) in Complete Freund's Adjuvant (CFA). At the time of sacrifice, three mice were in relapse (lanes 1, 3, 4), one mouse was experiencing the first clinical episode of disease (lane 2), and one mouse remained asymptomatic (lane 5). CXCL13 mRNA was expressed in spinal cords from the four mice with EAE, but not in asymptomatic or naïve animals (FIG. 1A). CXCR5 mRNA (the receptor for CXCL13) was detectable in two of the diseased cords. CCL19 mRNA was also present in the diseased spinal cords and, at lower levels, in spinal cords from naïve animals. The expression of CCR7 (the receptor for CCL19 and CCL21) roughly followed the same pattern. mRNA for CXCL13, CCL19, CCL21, CXCR5 and CCR7 was detected in spinal cords from SJL mice and C57BL/6 mice with EAE induced using peptides of proteolipid protein (PLP) and myelin oligodenrocyte glycoprotein (MOG), respectively. Hence, CNS upregulation of lymphoid chemokines appears to be a general phenomenon in EAE, irrespective of strain or target autoantigen. CXCL13, CCL19 and CCL21 are not upregulated in spinal cords of mice injected with CFA alone.

174. Next levels of CXCL13, CCL21 and CCL19 mRNA in the CNS of mice during the course of relapsing-remitting disease were measured using an RNase Protection Assay (RPA). SJL mice were actively immunized against an immunodominant PLP epitope ($PLP_{139-151}$) in CFA and assessed daily for neurological deficits. Representative mice were sacrificed during the first episode, remission, and relapse of EAE, respectively, for mRNA quantification. It was found that expression of all three lymphoid chemokines rose progressively during the disease course (FIG. 2A).

175. FIGS. 1A and 2A demonstrate that lymphoid chemokine and chemokine receptor mRNA are upregulated in the cords of mice with EAE induced by active immunization with myelin peptides in combination with adjuvants (CFA and *Bordetella pertussis* toxin). In previous studies it was found that draining lymph node (LN) cells from SJL mice immunized with PLP peptide in IFA (without heat killed *Mycobacteria*) only induce EAE in naïve recipients following antigenic challenge in the presence of recombinant IL-12 (Segal, B. M., et al. 2000. *J Immunol* 164:5683-5688, Bagaeva, L. V., et al. 2003. *J Neuroimmunol* 137:109-116). FIG. 1B demonstrates that spinal cords harvested from mice with passively transferred EAE (12 days following injection of PLP/IFA primed, IL-12 stimulated T-cells), but not healthy controls, express CXCL13 and CXCR5. Furthermore CCL19 and CCR7 mRNA are also upregulated in the CNS of symptomatic recipients of encephalitogenic T-cells by comparison to control mice.

176. FIGS. 1 and 2 demonstrate that lymphoid chemokines are present in spinal cords of mice with EAE on the mRNA level. In order to test whether this mRNA is translated into protein, Western blot analyses was performed on pooled spinal cords from 10 mice with adoptively transferred EAE (mean clinical score 2.5) and 10 healthy controls. Spinal cord lysates from each group were immunoprecipitated using heparin Sepharose, as previously described (Luther, S. A., et al. 2000. *PNAS* 97:12694, Ansel, K. M., et al. 2000. *Nature* 406:309-314, Luther, S. A., et al. 2002. *J Immunol* 169:424-433). The chemokine proteins were detected with goat anti-mouse CCL19, CCL21 or CXCL13 (R&D Systems, Minneapolis, Minn.) followed by anti-goat horseradish peroxidase (Pierce Endogen); development was with Supersignal West Femto Maximum Sensitivity Substrate (Pierce). Recombinant chemokines and spleen lysates were used for positive controls. CXCL13, CCL21 and CCL19 proteins were readily detected in cords from the mice with EAE, but not healthy controls (FIG. 1C). Lysates from symptomatic and healthy mice yielded similar amounts of β-actin, a housekeeping protein. Similar results were obtained with cords from MOG-sensitized C57BL/6 mice.

177. In several EAE models intrathecal CXCL13 and CCL19 were found to be associated with MHC class II transactivator (CIITA) form I, a dendritic cell-specific molecular marker (FIG. 2A, Suter, T., et al. 2000. *Eur. J. Immunol.* 30:794). This indicates that dendritic cells are present in relapsing EAE lesions. Dendritic cells could be attracted to inflammatory foci by lymphoid chemokines (Cyster, J. G. 1999. *Science* 286:2098-2102, Moser, B., and Loetscher, P. 2001. *Nature Immunology* 2:123-128, Campbell, J. J., et al. 1998. *J. Cell. Biolo.* 141:1053). On the other hand, myeloid dendritic cells have been shown to produce CCL19 as well as CXCL13 under some circumstances (Vissers, J. L. M., et al. 2001. *Eur. J. Immunol.* 31:1544, 26). GM-CSF drives the differentiation of CNS microglia into myeloid DC in vitro (Fischer, H. G. and Reichmann, G. 2001. *J Immunol.* 166: 2717, Santambrogio, L., et al. 2001. *PNAS* 98:6295, Aloisi, F., et al. 2000. *J. Immunol.* 164:1705). Interestingly, GM-CSF is commonly produced by activated T-cells including myelin-reactive CD4+ T-cell lines (Wong, R. L., et al. 1989. *Cell. Immunol.* 123:445). Furthermore, it is expressed in the inflamed cords of mice with EAE in association with CD3 (FIG. 1A). Hence, GM-CSF, secreted by myelin-reactive T-cells in EAE lesions, can stimulate microglia to differentiate into myeloid dendritic cells and produce lymphoid chemokines locally.

Figure 8:
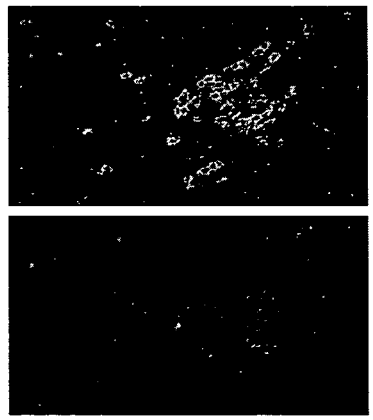
FIG. 8 shows that $CD11c^+$ cells are present in EAE infiltrates and form clusters with infiltrating T-cells.
Figure 8:
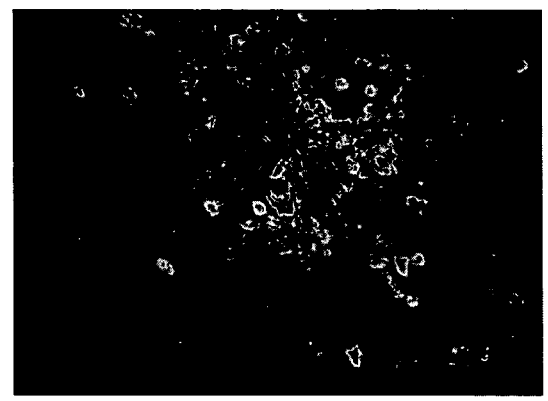

178. In order to assess whether dendritic-like cells accumulate in EAE lesions in association with infiltrating T-cells, frozen or whole mount sections of spinal cords from symptomatic mice were stained with a monoclonal antibody against CD11c, a myeloid dendritic cell marker. CD11c+ cells were readily detected within perivascular infiltrates. Furthermore, these dendritic-like cells formed clusters with CD4+ T-cells (FIG. 8).

179. In an initial attempt to identify the cellular source of lymphoid chemokines in the CNS during EAE, mononuclear cells from spinal cords of symptomatic mice were isolated over a 30%/70% Percoll gradient. Flow cytometric analysis revealed that these cells were bone marrow derived (95% of the total cell population was CD45+) and consisted primarily of myeloid cells, many of which express the dendritic cell marker CD11c (FIG. 4A). Lymphoid cells were almost exclusively CD4+ T-cells, and comprised 26% of the total population. RT-PCR studies revealed that CD11c+CD11b+ spinal cord inflammatory cells, purified from mice at peak disease, express CXCL13, CCL21 and CCL19 mRNA (FIG. 4B). Interestingly, while CXCL13 mRNA levels appear to rise in the CD11c+ cells between the first and second EAE episode, CCL19 and CCL21 mRNA levels wane.

180. The results shown in FIGS. 1A, and 2A indicate that CXCL13 is produced in the CNS during clinical EAE and that its receptor, CXCR5, is expressed on the mRNA level concurrently. CXCR5 is expressed on a subset of CD4+ T-cells in germinal centers in peripheral lymphoid tissues (Kim, C. H., et al. 2001. *J Exp Med.* 193:1373-1381). Collectively, these observations led to the belief that myelin-reactive effector T-cells might express CXCR5, thereby facilitating their migration from peripheral sites to active demyelinating lesions, altering their localization within inflammatory foci in the central nervous system (possibly to faciliate interactions with B cells or myeloid cells), and/or facilitating their stimulation within the central nervous system. If so, PLP-primed LN cells used to induce EAE in adoptive transfer studies might include $CXCR5^+$ $CD3^+$ T-cells. To investigate that possibility, PLP-primed LN cells were harvested 4 days after antigenic stimulation in vitro and permeabilized them prior to staining with FITC-labeled anti-CXCR5 monoclonal antibodies and analysis by flow cytometry. A control sample was labeled with isotype matched, FITC-labeled, antibodies. As shown in FIG. 9, a subset of CD3+ T-cells among the PLP-primed LN cells was indeed positive for CXCR5. Similar results were obtained by staining for CXCR5 on the cell surface.

181. In order to measure $CXCR5^+$ T-cell accumulation in the CNS during EAE spinal cord mononuclear cells were isolated from mice during the first exacerbation and stained them with flourochrome-labeled monoclonal antibodies specific for CXCR5 and either CD4 or CD3. Subsequent flow cytometric analysis revealed that between 11-16% of CNS inflammatory cells were $CD4^+CXCR5^+$. A representative example is shown in FIG. 5C. Virtually all of these cells bore the memory cell marker CD44 and expressed iCOS. (This cell surface phenotype is typical of germinal center follicular helper $CD4^+$T-*cells that promote B cell differentiation. The percentage of* $CD4^+CXCR5^+$ T-cells within the CNS mononuclear cell compartment increases as the disease advances. By the second relapse they comprise 23-25% of spinal cord mononuclear cells. Although IgM+ CXCR5+ B cells only comprise a minor subset of CNS inflammatory cells during the first exacerbation, they accumulate in greater numbers in later stages.

Figure 5:
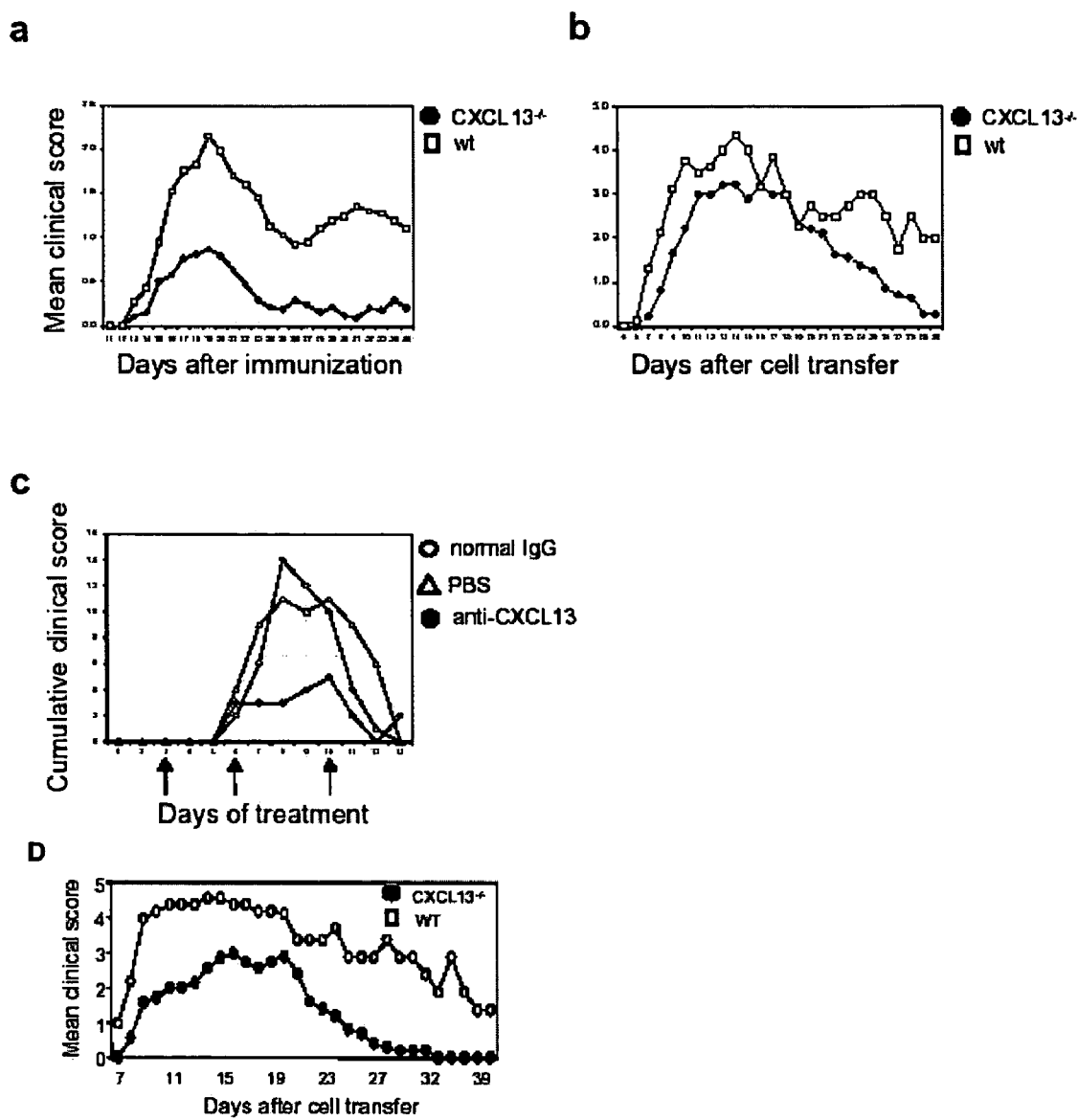
FIG. 5 shows CXCL13 deficiency or blockade supresses EAE during the effector stage. In the experiments shown in FIG. 5(A), EAE was induced in C57BL/6 wildtype (open circles; n=20) and CXCL13−/− (closed circles; n=19) mice by active immunization with $MOG_{35-55}$/CFA. The difference in clinical scores between groups is statistically significant (P<0.0001 by the Mann-Whitney Rank Sum Test). The results are representative of three experiments. In the experiments shown in FIG. 5(B), EAE was induced in C57BL/6 wildtype (open circles; n=8) and CXCL13−/− (closed circles; n=9) mice by adoptive transfer and rated as described above. The difference in clinical scores between groups is statistically significant (P<0.0001 by the Mann-Whitney Rank Sum Test). This experiment was performed twice with similar results.

182. The data shown in FIG. 3 demonstrates that $CXCR5^+$ $CD4^+$ T-cells infiltrate the CNS in correlation with local CXCL13 expression. The impact of CXCL13 neutralization on clinical EAE was assessed. SJL mice were treated with goat anti-mouse CXCL13, isotype matched control antibodies or PBS (n=5/group) on days 3, 6 and 10 post transfer. Animals were examined daily and rated for neurological impairment on a 5 point scale. As shown in FIG. 5, the animals treated with anti-CXCL13 were protected from EAE.

183. In a parallel approach to that illustrated in FIG. 5, C57BL/6 wildtype and CXCL13 deficient mice were immunized with $MOG_{35-55}$ in CFA and rated them daily for neurological deficits. Although CXCL13−/− mice succumbed to clinical EAE, the intensity of their symptoms was significantly reduced and they recovered at a faster rate and more completely than their wildtype counterparts.

184. CXCL13 deficient mice have disorganized splenic architecture as well as a paucity of certain lymph nodes. Therefore, resistance of these mice to EAE can results from defective priming of autoimmune effector cells in the periphery as opposed to defective recruitment and/or retention of $CXCR5^+$ T-cells in the CNS. To address that possibility MOG-specific responses of splenocytes from mice were measured by a number of T-cell assays. It was found that sensitized CXCL13 deficient animals mounted significant lymphoproliferative, IFNγ and IL-2 responses on ex vivo challenge that were comparable to those of their wildtype counterparts (Table 1). In fact, MOG-specific proliferation appeared to be enhanced in CXCL13−/− mice.

Example 3

$CXCR5^+$ and $CCR7^+$ Leukocytes Accumulate in EAE Lesions.

Figure 3:
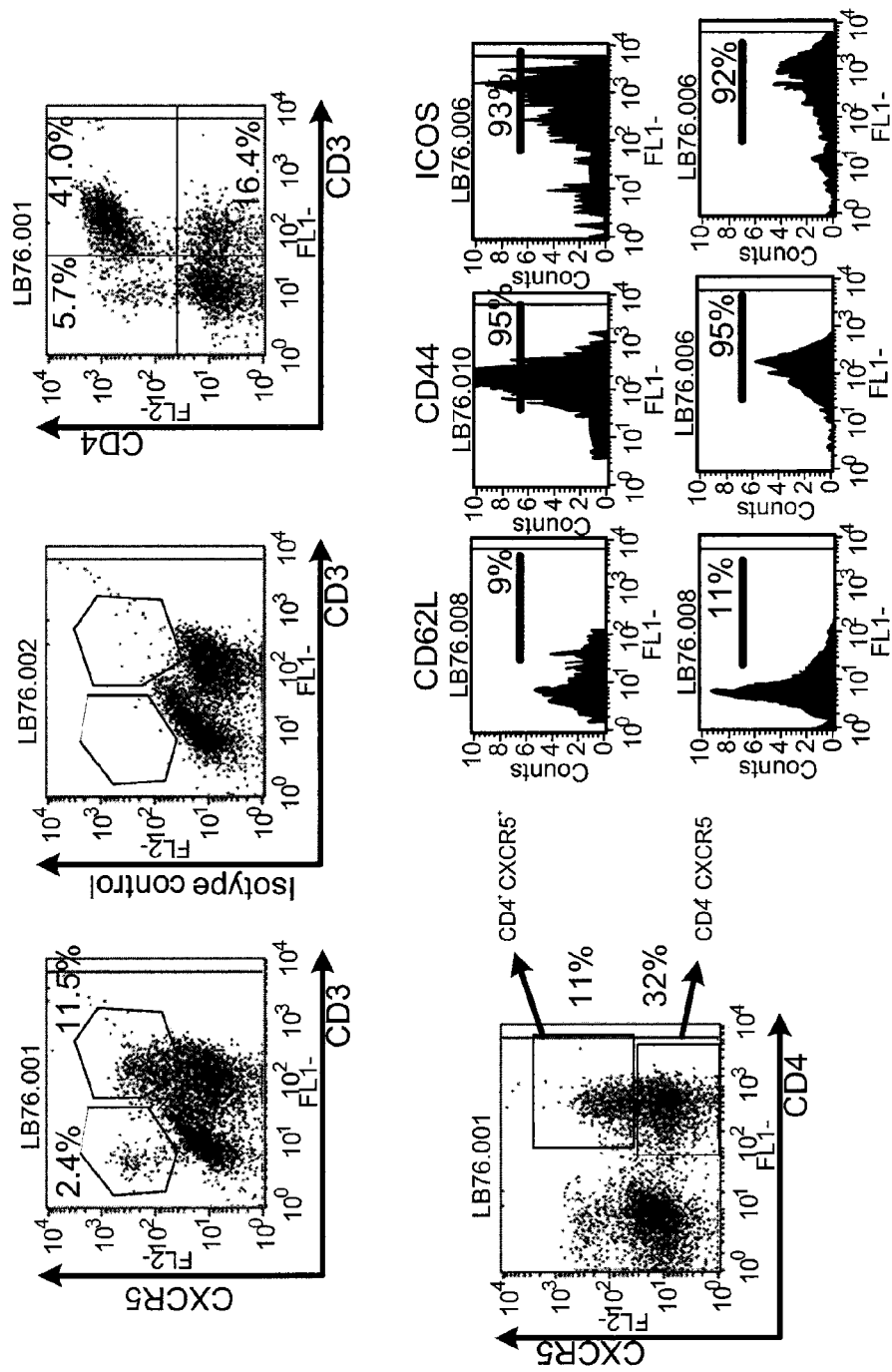
FIG. 3 shows that CXCR5+CD4+ T-cells with a memory effector phenotype, and a subset of CD4+CD3− cells, accumulate in the spinal cords of mice with EAE.

185. It has been shown that $CCR7^+$ and $CXCR5^+$ leukocytes accumulate in the CNS during the course of EAE. Alt and colleagues detected $CCR7^+$ cells in perivascular EAE infiltrates by in situ hybridization and immunoshitochemical analysis. Furthermore, it was found that $CCR7^+$ cells appear in spinal cords of sick mice by RT-PCR (FIG. 1A). In addition, $CXCR5^+$ $CD4^+$ T-cells accumulate in the CNS as early as the first episode of EAE (FIGS. 1A, 2A, and 3). The infiltrating T-cell population becomes increasingly enriched for $CXCR5^+$ and $CCR7^+$ cells during disease progression, in conjunction with rising levels of CXCL13 and CCL19 (FIG. 2A). $CXCR5^+$ $IgM^+$ B cells begin to appear in the CNS during the first relapse in SJL mice and during the chronic phase of EAE in C57BL/6 mice. A population of CD4, CD3, $CCR7^+$ cells that can represent mature $CD11c^+$ dendritic cells arise at an early time point in the clinical course.

186. The chemotaxis of spinal cord mononuclear cells harvested from mice with EAE across a transwell membrane in response to a CXCL13, CCL19 or CCL21 gradient (Legler, D. F., et al. 1998. *J. Exp. Med.* 187:665) can be measured. In addition, migrating cells can be rigorously characterized by flow cytometric analysis. It has been found that $CCR7^+$ and $CXCR5^+$ populations within CNS infiltrates evolve over the course of EAE. For example, $CXCR5^+$ cells are almost exclusively $CD4^+$ at the time of the first exacerbation in SJL mice, whereas $CXCR5^+$ B cells begin to accumulate by the subsequent relapse (FIG. 3). B cells also become more prominent in chronic EAE infiltrates of MOG-sensitized C57BL/6 mice as the disease advances.

187. The lower chamber of a transwell (Costar; 5.0 μm pore size filters/6.5 mm diameter) can be filled with tissue culture media with or without recombinant CXCL13, CCL19 or CCL21 (R&D Systems) over a range of concentrations (between 5 and 100 nM in a total volume of 0.6 ml). These concentrations were chosen based on previous reports of optimal conditions for stimulating chemotaxis (Legler, D. F., et al. 1998. *J. Exp. Med.* 187:665). CNS mononuclear cells (enriched over a Percoll gradient) can be added to the upper chamber ($1.5 \times 10^6$ cells in 0.25 ml). After a 3 hour incubation at 37° C., 5% $CO_2$, cells can be harvested from the lower chamber, concentrated by centrifugation, counted and stained with FITC- and/or PE-labeled antibodies specific for selected leukocyte markers (such as CD4, CD8, IgM, B220 and CD11c). In certain instances cells can be costained to measure memory markers (CD62L, CD44), costimulatory molecules (iCOS, CD40, CD40L), or cytokine receptors (IL-7R) The samples can then be subjected to flow cytometric analysis. Whole splenic cell suspensions or purified splenic subpopulations can serve as positive controls (B cells for CXCL13; T-cells for CCL19/CCL21). Each assay can be done in triplicate. In certain experiments neutralizing antibodies can be added along with recombinant chemokines to some wells to further demonstrate the specificity of chemotaxis.

188. Data can be presented as the number of migrated cells (either total or of a particular subset) into chemokine-containing wells minus the number of migrated cells into wells containing media only. Means and p values can be determined by ANOVA with parametric, 2-tailed post-hoc analysis. This approach can allow in detail characterization of the cell surface phenotype of CNS mononuclear cells that are responsive to individual lymphoid chemokines during different stages of EAE.

189. CXCL13 can stimulate CXCR5$^+$CD4$^+$ T-cells in inflammatory demyelinating lesions. Furthermore, these cells can co-express iCOS, IL-7 receptor and CD40L, a profile reminiscent of germinal center follicular helper T-cells. At later stages of disease, IgM$^+$ CXCR5$^+$ B cells can comprise a larger percentage of CXCL13-responsive cells within the CNS infltrates. On the other hand, CCL19 and CCL21 can stimulate CCR7$^+$CD4$^+$ T-cells with a resting or Tcm phenotype as well as CCR7$^+$ CD11c$^+$ myeloid cells.

190. During later stages of EAE in C57BL/6 mice a growing population of CXCR5$^+$CD3$^-$ cells has been detected, at least some of which appear to be B cells. This subpopulation can be characterized in detail by costaining for B220, immunoglobulin light chains, CD19, CD4 and CD40. The relative dependence of CXCR5$^+$ subsets on CXCL13 for CNS accumulation can be determined by performing flow cytometric analysis on spinal cord mononuclear cells from wildtype and CXCL13 deficient mice following the transfer of encephalitogenic T-cells.

191. Analogous experiments can be performed using plt/plt mice to assess the role of CCL21 and CCL19 on the recruitment of CCR7$^+$ leukocytes. Once again an adoptive transfer model can be used. For flow cytometric analysis, infiltrating CCR7$^+$ CD4$^+$ T-cells can be costained with antibodies against CD62 and CD44 in order to distinguish naïve and central memory lymphocytes. Mononuclear cells against CD11c and CD11b can be stained in an attempt to detect mature CCR7$^+$ dendritic cells that are responsive to CCL19/21.

192. These studies can indicate that CCL19/21 can be required for optimal accumulation of CD11c$^+$ myeloid cells and central memory and naïve T-cells in CNS infiltrates. On the other hand, CXCL13 promotes the recruitment of activated CD4$^+$ T-cells (with a cell surface phenotype characteristic of follicular helper cells) and B cells.

193. The data disclosed herein indicate that, although lymphoid chemokine production begins in the CNS during the first exacerbation, levels rise substantially at relapse (FIG. 2A). Therefore, CD4$^+$ T or B cells expressing a genetic marker can be transferred into actively immunized mice during their first remission of EAE. The homing patterns of the transferred cells can then be followed during the subsequent relapse in hosts injected with either neutralizing antibodies against lymphoid chemokines or control antibodies. It is understood that lymphoid chemokine neutralizing antibodies can block the homing of transferred cells to the CNS.

194. EAE infiltrates contain a substantial number of T-cells that express a naïve phenotype (Raine, C. S., et al. 1984. *Laboratory Investigation* 51:534-546). Many naïve T-cells express CCR7, the receptor for CCL19 and CCL21 (Cyster, J. G. 1999. *Science* 286:2098-2102, Luther, S. A., et al. 2002. *J Immunol* 169:424-433). Therefore, the effects of CCL19 and CCL21 blockade on the migration of resting T-cells to the CNS during EAE relapses in SJL mice can be assessed. For example, Thy1.2$^+$ SJL mice can be used as donors and congeneic SJL Thy1.1$^+$ mice as recipients. The latter mice are obtained from Jackson Laboratories. They have been tested extensively to show a lack of alloreactivity to the Thy-1 disparity. Following injection donor cells can be identified by staining with antibodies specific for the Thy 1.2 marker.

195. CD4$^+$ T-cells expressing a naïve phenotype (CD62$^{high}$, CD44$^{low}$) can be purified from pooled lymph nodes and spleens of unmanipulated Thy 1.2$^+$ donors by FACS sorting. These cells will then be injected into Thy1.1$^+$ mice during their first remission of EAE (defined as a clinical score of 1 or 2 points below peak severity maintained for 2 or more days). Hosts can be divided into two groups, one of which can be treated with a cocktail of neutralizing antibodies against CCL19 and CCL21 (R&D Systems) and the other with isotype matched control antibodies (250 µg of each mAb i.p./mouse every 72 hours from the time of cell transfer onwards). This dosing protocol has been previously used to neutralize CCL19 and CCL21 in vivo in other experimental systems with significant biological effects (Itakura, M., et al. 2001. *J Immunol.* 166:2071). Mice can then be sacrificed at the time of expected peak relapse. Mononuclear cells can be isolated from their spinal cords and stained against CD4 and Thy1.2 prior to flow cytometric analysis.

196. As mentioned above, a subset of activated CD4$^+$ T-cells and B cells home to the CNS during relapsing EAE in response to CXCL13. To test this, PLP-reactive CD4$^+$ T-cell lines derived from Thy1.2$^+$ SJL donors can be injected into Thy1.1$^+$ hosts during the first remission of actively induced EAE. In other experiments Thy1.2$^+$ IgM$^+$ CD19$^+$ B cells, isolated from naïve splenocytes using magnetic beads or FACs sorting, can be transferred. Subsequently, the hosts can be treated with either a neutralizing antibody against CXCL13 or isotype matched control antibodies (R&D Systems, 200 µg/mouse i.p. every 72 hours, FIG. 5; (Itakura, M., et al. 2001. *J Immunol.* 166:2071) until sacrifice at the time of expected relapse. CNS-infiltrating mononuclear cells can then be isolated and analyzed for the presence of Thy1.2$^+$ CD4$^+$ or Thy1.2$^+$ CD19$^+$ emigrants. It is understood from the experiments above that anti-CCL19/21 antibodies can block the migration of naïve cells (including those reactive to secondary myelin epitopes) and anti-CXCL13 antibodies can block the migration of primed myelin-reactive T-cells and B cells to the CNS during EAE relapses.

Example 4

Lymphoid Chemokines Play a Physiological Role in the Establishment of Progressive and Relapsing EAE 197. Chemokine deficient mice can be used to assess the contribution of CXCL13, CCL19 and CCL21 to disease severity and chronicity. CXCL13 deficient mice on a C57BL/6 background (Ansel, K. M., et al. 2000. *Nature* 406:309-314, Ansel, K. M., et al. 2002. *Immunity* 16:67-76) and plt mice (which are deficient in CCL19 and CCL21 in secondary lymphoid tissues), also on a C57BL/6 background, were obtained (Luther, S. A., et al. 2000. *PNAS* 97:12694, Mori, S., et al. 2001. *J. Exp. Med.* 193: 207, Gunn, M. D., et al. 1999. *J. Exp. Med.* 189:451-460, Nakano, H., and Gunn, M. D. 2001. *J Immunol.* 166:361).

198. In the experiments disclosed herein it was found that clinical EAE was suppressed in actively immunized CXCL13−/− mice. However, secondary lymphoid tissues were disorganized in these knock-outs as well as in plt mice. Plt mice demonstrate disrupted homing of naïve T-cells and activated dendritic cells to T-cell zones and an abnormal distribution of T-cells within secondary lymphoid tissues (Gunn, M. D., et al. 1999. *J. Exp. Med.* 189:451-460). CXCL13 deficient mice have absent or very sparse peripheral lymph node tissues, a reduced number of Peyer's patches and they lack follicular dendritic cells and organized follicles (Gunn, M. D., et al. 1998. *Nature.* 391:799, Ansel, K. M., et al. 2000. *Nature* 406:309-314). Such abnormalities of secondary lymphoid tissue might interfere with the priming and/or expansion of antigen-specific T-cells in vivo in response to vaccination. An adoptive transfer model in which wildtype myelin-reactive T-cells are injected into naïve, syngeneic chemokine-deficient or wildtype recipients allows for the avoidance of artifacts arising from insufficient effector cell activation, differentiation and/or expansion secondary to lymphoid chemokine deficiencies during T-cell priming.

199. C57BL/6 mice are relatively resistant to EAE induced by the adoptive transfer of myelin-primed T-cells according to standard protocols. However, it has been shown that myelin oligodendrocyte glycoprotein (MOG)-specific T-cells from primed C57BL/6 donors acquire encephalitogenic properties following antigenic challenge in the presence of recombinant IL-12 (Spahn, T. W., et al. *Eur. J. Immunol.* 29: 4060). Therefore, this approach can be used to compare the effector phase of EAE in chemokine-deficient and wildtype hosts. In each experiment donor cells can be cultured with an optimal concentration of MOG peptide (25 µg/ml) and murine IL-12 (5 ng/ml) in TCM. At 96 h, the cells can be harvested, washed, counted and injected into sex and age matched wildtype and chemokine deficient recipients ($50 \times 10^6$ cells/mouse i.p.). The disease incidence, chronicity, relapse rate, severity and histological features can be compared between the experimental groups. The significance of observed differences can be assessed using either Student's t test or the Wilcoxon signed rank test. It is understood that CXCL13−/− and plt mice can experience a relatively mild from of EAE with more complete recovery from exacerbations.

200. One of the ways in which CNS lymphoid chemokines can facilitate clinical EAE is by organizing white matter infiltrates through the process of lymphoid neogenesis. In fact, mice that express a CXCL13 or CCL21 transgene under control of the rat insulin promoter develop lymph-node like structures in the pancreas that contain T and B cell zones, high endothelial venules and stromal cells. Transgenic CXCL13 also induced CCL21 expression in inflamed blood vessels and stromal cells within these lymphoid structures.

Figure 10:
FIG. 10 shows that MAdCAM is upregulated on cerebrovasculature during EAE. Pictured is an EAE lesion in the spinal cord of a MOG-sensitized C57BL/6 mouse with EAE (clinical score 2). A whole mount section of the thoracolumbar cord was stained with anti-CD45-FITC and anti-MAdCAM-PE prior to visualization under a fluorescent microscope. Isotype controls showed negligible background staining. Anti-MADCAM does not stain vessels in spinal cords from naïve or mock-immunized mice.

201. A similar phenomenon can occur during the development of white matter infiltrates during EAE, driven by the production of endogenous lymphoid chemokines in the CNS. Indeed, it has been found that MAdCAM-1 is upregulated on cerebrovascular blood vessels in inflamed cords of wildtype mice with EAE (FIG. 10). Furthermore, a subpopulation of $CXCR5^+\alpha4\beta7^+$ $IL-7R^+CD4^+CD3^-$ cells were detected among spinal cord mononuclear cells that could represent lymphoid precursor cells (mesenchymal cells that fix sites of lymphoid organogenesis). Hence, spinal cords from wildtype and lymphoid chemokine deficient adoptive transfer recipients can be compared for features of lymphoid neogenesis and for accumulation of lymphoid precursor cells.

202. Spinal cords can be removed from wildtype, CXCL13 deficient, and plt/plt mice with adoptively transferred EAE across a range of clinical scores. An attempt can be made to match animals across groups based upon degree of paralysis. Representative cords can be snap frozen, sectioned and stained for BP3 and ER-TR7 (Accurate Chemicals), antigens common to stromal cells in B and T-cell areas of lymphoid organs. This approach was used to detect a network of stromal cells in the pancreatic infiltrates of RIP-CXCL13 transgenic mice. Contiguous sections can be stained with antibodies specific for HEV-like adhesion molecules including MAd-CAM-1 and the peripheral lymph node addressin, PNAd. Immunoreactive cells can be counted in spinal cord sections from 6-8 different areas by two blinded examiners at ×10 and ×63 magnification. Lastly, CCL21 expression in cords from CXCL13 deficient can be compared to wildtype mice by RPA and immunohistochemistry.

203. Accumulation/modulation of lymphoid organ precursor cells to the CNS: Lymphoid organ precursor cells (bearing the cell surface phenotype $CD4^+CD3^-IL-7R\alpha^+$) fix sites of future lymph node organogenesis during early development. These cells are $CXCR5^+CCR7^+$ and are drawn to peripheral lymphoid areas by CXCL13 and/or CCL19/CCL21. Although CXCL13 and CCL19/21 have overlapping functions in attracting the precursor cells they are not completely redundant. That lymphoid precursor cells are recruited into the CNS during EAE by lymphoid chemokines can be tested using the following strategies: (i) Flow cytometric studies: Spinal cord mononuclear cells from wildtype, CXCL13−/− and plt/plt adoptive transfer recipients can be pooled and costained with antibodies against CD4, CD3, IL-7 receptor, $\alpha4\beta7$ integrin and/or CXCR5 or CCR7 prior to analysis on the flow cytometer. Cells expressing a lymphoid precursor cell surface profile can be profiled in each group; (ii) RT-PCR for Id2 and RORγ transcription factors that are expressed by lymphoid precursor cells: Transcripts for Id2, a helix-loop-inhibitor, and RORγ a retinoic acid receptor-related orphan receptor, have been detected in $CD4^+CD3^-IL-7R\alpha^+$ lymphoid precursor cells. Furthermore, both of these transcription factors appear to be critical for the generation and/or survival of the precursor cells. ($CD4^+CD3^-IL-7R\alpha^+CD45^+$ cells are absent in embryonic intestines of mice that are genetically deficient in either Id2 or RORγ. Both knock-outs lack lymph nodes and Peyer's patches.) Consequently, Id2 or RORγ can be used as markers of lymphoid precursor accumulation in the CNS. Spinal cords can be harvested from wildtype and lymphoid chemokine deficient mice at serial time points following adoptive transfer of encephalitogenic T-cells. RNA can be extracted from individual cords and perform RT-PCR with primers specific for Id2, RORγ and β-actin. CXCL13 and CCL19/21 deficient mice may not support lymphoid neogenesis in the CNS during EAE and $CD4^+CD3^-IL-7R\alpha^+$ cells can fail to accumulate in white matter lesions.

204. There is an extensive literature suggesting that antibodies are produced within the CNS of patient with MS. Furthermore, analysis of VDJ transcripts from cerebrospinal fluid cells or brain autopsy specimens suggests that B cells undergo somatic hypermutation and terminal differentiation within the CNS. The data disclosed herein demonstrate that B cells also undergo isotype switching in the CNS during EAE. In particular, circle transcripts and mRNA encoding activation induced cytidine deaminase (AID) has been detected in spinal cords from sick mice but not naïve controls (FIG. 11). Circle transcripts (CTγ), from DNA loci excised during switch recombination, are a specific and immediate byproduct of isotype switching in B cells and are considered a hallmark of active B cell activation. AID is a B cell-specific enzyme that is essential for somatic hypermutation and isotype switching. It is expressed at high levels in germinal center B lymphocytes. Since CXCL13 attracts $CD40L^+CD4^+$ T-cells and B cells to follicles and facilitates germinal center reactions, the chemokine can promote T-B cell collaborations in white matter infiltrates during EAE.

205. CXCL13 deficient and syngenic wildtype mice can be sacrificed at serial time points following the transfer of encephalitogenic T-cells. Mice can undergo intracardiac perfusion with PBS prior to spinal cord harvest. mRNA can be extracted from individual spinal cords and perform RT-PCR with primers for AID, Ig heavy chain circle transcripts (particularly CTγ2a, a circle transcript specific for the Th1 dependent IgG2a isotype), Mb-1 (a B cell-specific marker), CD4 and β-actin. RT-PCR can be followed by Southern blot hybridization with internal oligonucleotide probes specific for the relevant molecules. Band intensities can be measured by phosphorimaging and normalize AID and CTγ2a levels to Mb-1 (a measure of B cell infiltration). It is understood that AID and CTγ (circle transcript) expression can be reduced or absent in spinal cords from CXCL13 deficient mice.

Example 5

Monoclonal Antibody Against CXCL13 Ameliorates Adoptively Transferred EAE

Figure 15:
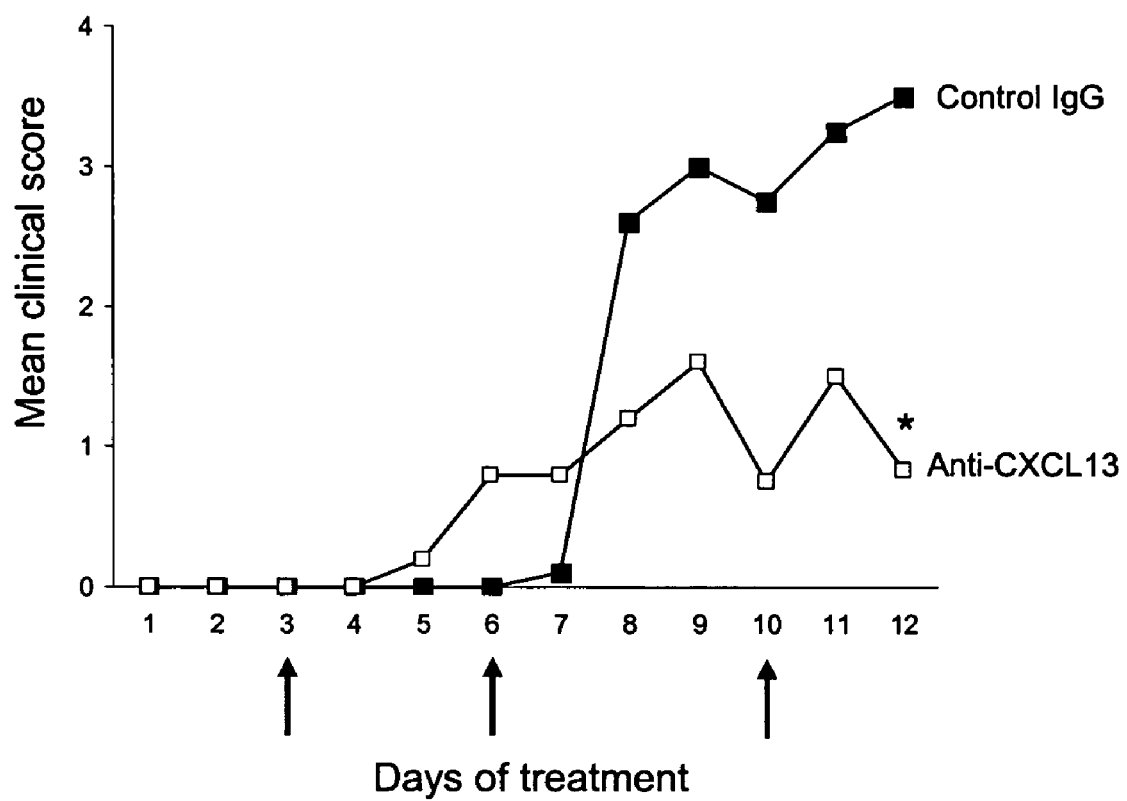
FIG. 15 shows that administration a monoclonal antibody against CXCL13 ameliorates adoptively transferred EAE. EAE was induced in naïve B10.PL female mice (n=5/group) by transfer of splenocytes from B10.PL donors that express a T-cell receptor transgene specific for myelin basic protein (MBP-TCR). MBP-TCR splenocytes were stimulated with antigen (MBP peptide Ac1-17; 50 µg/ml)) and recombinant murine IL-12 (2 ng/ml) for 96 hours prior to transfer ($35\times10^6$ cells/recipient). Recipients were injected with monoclonal antibodies (either anti-CXCL13 or control rat IgG2a, R&D; 300 µg i.p.) on days 3, 6 and 10 post cell transfer. Mice in both groups were rated for degree of paralysis on a 5 point scale by an examiner who was blinded to treatment group. * $p=0.03$ by Whitney-Mann test.

2. Experiments with CXCL13 deficient mice and immunocompetent mice treated with polyclonal antibodies against CXCL13 indicated that the chemokine is important for the clinical manifestation of experimental autoimmune encephalomyelitis (EAE) (FIG. 5 A-C). It was next questioned whether anti-CXCL13 monoclonal antibodies would suppress EAE when administered during the effector phase of disease. To address that question an adoptive transfer model was used in which naïve B10.PL mice were injected with activated, syngeneic T-cells that express a transgenic T-cell receptor specific for a peptide fragment of myelin basic protein (MBP-TCR). MBP-TCR cells were stimulated with MBP peptide Ac1-17 and recombinant murine IL-12 for 96 hours prior to transfer ($35 \times 10^6$ cells/recipient). The adoptive transfer recipients were then treated with either a neutralizing monoclonal antibody against CXCL13 or isotype matched control antibody on days 3, 6 and 10 post transfer (n=5/ group). As shown in FIG. 15, mice in the control group developed a severe form of EAE that peaked on day 11 with a mean clinical score of 3.5, consistent with significant hindlimb paresis. By contrast, mice treated with the anti-CXCL13 monoclonal antibody experienced a relatively mild course with a mean score of 0.83 on day 11, indicative of limp tail but no discernable limb weakness. These results indicate that anti-CXCL13 monoclonal antibodies are effective therapies for inflammatory conditions including but not limited to multiple sclerosis.

206. Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

207. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Aloisi, F., De Simone, R., Columba-Cabezas, S., Penna, G., and Adorini, L. 2000. Functional maturation of adult mouse resting microglia into an APC is promoted by Granulocyte-Macrophage Colony-Stimulating Factor and interaction with Th1 cells. *J. Immunol.* 164:1705.

Alt, C., Laschinger, M., and Engelhardt, B. 2002. Functional expression of the lymphoid chemokines CCL19 (ELC) and CCL 21 (SLC) at the blood-brain barrier suggests their involvement in G-protein-dependent lymphocyte recruitment into the central nervous system during experimental autoimmune encephalomyelitis. *European Journal of Immunology* 32:2133-2144.

Ando, D. G., Clayton, J., Kono, D., Urban, J. L., and Sercarz, E. E. 1989. Encephalitogenic T-cells in the B10.PL model of experimental allergic encephalomyelitis (EAE) are of the Th-1 lymphokine subtype. *Cell Immunol* 124:132-143.

Ansel, K. M., Harris, R. B., and Cyster, J. G. 2002. CXCL13 is required for B1 cell homing, natural antibody production, and body cavity immunity. *Immunity* 16:67-76.

Ansel, K. M., McHeyzer-Williams, L. J., Ngo, V. N., McHeyzer-Williams, M. G., and Cyster, J. G. 1999. In vivo-activated CD4 T-cells upregulate CXC chemokine receptor 5 and reprogram their response to lymphoid chemokines. *Journal of Experimental Medicine* 190:1123-1134.

Ansel, K. M., Ngo, V. N., Hyman, P. L., Luther, S. A., Forster, R., Sedgwick, J. D., Browning, J. L., Lipp, M., and Cyster, J. G. 2000. A chemokine-driven positive feedback loop organizes lymphoid follicles. *Nature* 406:309-314.

Bagaeva, L. V., Williams, L. P., and Segal, B. M. 2003. IL-12 dependent/IFN gamma independent expression of CCR5 by myelin-reactive T-cells correlates with encephalitogenicity. *Journal of Neuroimmunology* 137:109-116.

Baranzini, S. E., Jeong, M. C., Butunoi, C., Murray, R. S., Bernard, C. C., and Oksenberg, J. R. 1999. B cell repertoire diversity and clonal expansion in multiple sclerosis brain lesions. *Journal of Immunology* 163:5133-5144.

Baron, J. L., Madri, J. A., Ruddle, N. H., Hashim, G., and Janeway, C. A., Jr. 1993. Surface expression of alpha 4 integrin by CD4 T-cells is required for their entry into brain parenchyma. *J Exp Med* 177:57-68.

Bauer, J., I. Huitinga, W. Zhao, H. Lassmann, W. F. Hickey, C. D. Dijkstra. 1995. The role of macrophages, perivascular cells, and microglial cells in the pathogenesis of experimental allergic encephalomyelitis. *Glia* 15:437

Bauer, J., Ruuls, S. R., Huitinga, I., and Dijkstra, C. D. 1996. The role of macrophage subpopulations in autoimmune disease of the central nervous system. *Histochemical Journal* 28:83-97.

Becher, B., Durell, B. G. and Noelle, R. J. 2002. Experimental autoimmune encephalitis and inflammation in the absence of interleukin-12. *J Clin Invest* 110:493.

Biber, K., Sauter, A., Brouwer, N., Copray, S., and Boddeke, H. 2001. Ischemia-induced neuronal expression of the microglia attracting chemokine Secondary Lymphoid Tissue Chemokine (SLC). *Glia* 34:121.

Bielekova, B., Goodwin, B., Richert, N., Cortese, I., Kondo, T., Afshar, G., Gran, B., Eaton, J., Antel, J., Frank, J. A., et al. 2000. Encephalitogenic potential of the myelin basic protein peptide (amino acids 83-99) in multiple sclerosis: results of a phase II clinical trial with an altered peptide ligand. *Nat Med* 6:1167-1175.

Boven, L. A., Montagne, L., Nottet, H. S., and DeGroot, C. J. 2000. Macrophage inflammatory protein-1alpha (MIP-1alpha), MIP-1beta, and RANTES mRNA semiquantification and protein expression in active demyelinating multiple sclerosis (MS) lesions. *Clin Exp Immunol.* 122:257.

Campbell, J. J., Bowman, E. P., Murphy, K., Youngman, K. R., Siani, M. A., Thompson, D. A., Wu, L. J., Zlotnik, A., and Butcher, E. C. 1998. 6-C-kine (SLC), a lymphocyte adhesion-triggering chemokine expressed by high endothelium, is an agonist for the MIP-3 beta receptor CCR7. *J. Cell. Bio.* 141:1053.

Cannella, B., Cross, A. H., and Raine, C. S. 1990. Upregulation and coexpression of adhesion molecules correlate with relapsing autoimmune demyelination in the central nervous system. *Journal of Experimental Medicine* 172:1521-1524.

Cella, M., Scheidegger, K., Palmer-Lehmann, K., Lane, P., Lanzavechia, A., and Alber, G. 1996. Ligation of CD40 on dendritic cells triggers production of high levels of IL-12 and enhances T-cell stimulatory activity: T-T help via APC activation. *J. Exp. Med.* 184:747.

Chen, S. C., Leach, M. W., Chen, Y., Cai, X. Y., Sullivan, L., Wiekowski, M., Dovey-Hartman. B. J., Zlotnik, A., and Lira, S. A. 2002. Central nervous system inflammation and neurological disease in transgenic mice expressing the CC chemokine CCL21 in oligodendrocytes. *J Immunol.* 168 (3):1009.

Colombo, M., Dono, M., Gazzola, P., Roncella, S., Valetto, A., Chiorazzi, N., Mancardi, G. L., and Ferrarini, M. 2000. Accumulation of clonally related B lymphocytes in the cerebrospinal fluid of multiple sclerosis patients. *Journal of Immunology* 164:2782-2789.

Columba-Cabezas, S., Serafini, B., Ambrosini, E., and Aloisi, F. 2003. Lymphoid chemokines CCL19 and CCL21 are expressed in the central nervous system during experimental autoimmune encephalomyelitis: implications for the maintenance of chronic neuroinflammation. *Brain Pathology* 13:38-51.

Correale, J., and de los Milagros Bassani Molinas, M. 2002. Oligoclonal bands and antibody responses in multiple sclerosis. *Journal of Neurology* 249:375-389.

Cross, A. H., Cannella, B., Brosnan, C. F., and Raine, C. S. 1990. Homing to central nervous system vasculature by antigen-specific lymphocytes. I. Localization of 14C-labeled cells during acute, chronic, and relapsing experimental allergic encephalomyelitis. *Lab Invest* 63:162-170.

Cross, A. H., Trotter, J. L., and Lyons, J. 2001. B cells and antibodies in CNS demyelinating disease. *Journal of Neuroimmunology* 112:1-14.

Cyster, J. G. 1999. Chemokines and cell migration in secondary lymphoid organs. *Science* 286:2098-2102.

Eugster, H-P, Frei, K., Bachmann, R., Bluethmann, H., Lassman, H., and Fontana, A. 1998. Severity of symptoms and demyelination in MOG-induced EAE depends on TNFR1. *Eur. J. Immunol.* 29:626.

Fan, L., Reilly, C. R., Luo, Y., Dorf, M. E., and Lo, D. 2000. Ectopic expression of the chemokine TCA4/SLC is sufficient to trigger lymphoid neogenesis. *J. Immunol.* 164:3955.

Fife, B. T., Paniagua, M. C., Lukacs, N. W., Kunkel, S. L., and Karpus, W. J. 2001. Selective CC chemokine receptor expression by central nervous system-infiltrating encephalitogenic T-cells during experimental autoimmune encephalomyelitis. *J Neurosci Res* 66:705-714.

Finke, D., Acha-Orbea, H., Mattis, A., Lipp, M., and Kraehenbuhl, J. 2002. CD4+CD3− cells induce Peyer's patch development: role of alpha4beta1 integrin activation by CXCR5. *Immunity* 17:363-373.

Fischer, H. G. and Reichmann, G. 2001. Brain dendritic cells and macrophages/microglia in central nervous system inflammation. *J Immunol.* 166:2717.

Forster, R., Mattis, A. E., Kremmer, E., Wolf, E., Brem, G., and Lipp, M. 1996. A putative chemokine receptor, BLR1, directs B cell migration to defined lymphoid organs and specific anatomic compartments of the spleen. *Cell* 87:1037-1047.

Genain, C. P., Nguyen, M. H., Letvin, N. L., Pearl, R., Davis, R. L., Adelman, M., Lees, M. B., Linington, C., and Hauser, S. L. 1995. Antibody facilitation of multiple sclerosis-like lesions in a nonhuman primate. *Journal of Clinical Investigation* 96:2966-2974.

Gerritse, K., Deen, C., Fasbender, M., Ravid, R., Boersma, W., and Claassen, E. 1994. The involvement of specific anti myelin basic protein antibody-forming cells in multiple sclerosis immunopathology. *Journal of Neuroimmunology* 49:153-159.

Gommerman, J. L., Giza, K., Perper, S., Sizing, I., Ngam-Ek, A., Nickerson-Nutter, C., and Browning, J. L. 2003. A role for surface lymphotoxin in experimental autoimmune encephalomyelitis independent of LIGHT. *J Clin Invest* 112:755-767.

Gunn, M. D., Kyuwa, S., Tam, C., Kakiuchi, T., Matsuzawa, A., Williams, L. T., and Nakano, H. 1999. Mice lacking expression of secondary lymphoid organ chemokine have defects in lymphocyte homing and dendritic cell localization. [comment]. *Journal of Experimental Medicine* 189:451-460.

Gunn, M. D., Ngo, V. N., Ansel, E. H., Ekland, E. H., Cyster, J. G. and Williams, L. T. 1998. A B cell homing chemokine made in lymphoid follicles activates Burkitt's lymphoma receptor-1. *Nature.* 391:799.

Hikino, H., Miyagi, T., Hua, Y., Hirohisa, S., Gold, D. P., Li, X.-K., Fujino, M., Tetsuya, T., Amemiya, H., Suzuki, S., Robb, L., Miyata, M., and Kimura, H. 2000. GM-CSF-independent development of dendritic cells from bone marrow cells in the GM-CSF-receptor deficient mouse. *Transplantation Proceedings.* 42:2458.

Hjelmstrom, P., Fjell, J., Nakagawa, T., Sacca, R., Cuff, C. A., and Ruddle, N. H. 2000. Lymphoid tissue homing chemokines are expressed in chronic inflammation. *American Journal of Pathology* 156:1133-1138.

Iglesias, A., Bauer, J., Litzenburger, T., Schubart, A., and Linington, C. 2001. T- and B-cell responses to myelin oligodendrocyte glycoprotein in experimental autoimmune encephalomyelitis and multiple sclerosis. *Glia.* 36:220.

Ishikawa, S., Sato, T., Abe, M., Nagai, S., Onai, N., Yoneyama, H., Zhang, Y., Suzuki, T., Hashimoto, S., Shirai, T., et al. 2001. Aberrant high expression of B lymphocyte chemokine (BLC/CXCL13) by C11b+CD11c+ dendritic cells in murine lupus and preferential chemotaxis of B1 cells towards BLC. *J Exp Med* 193:1393-1402.

Itakura, M., Tokuda, A., Kimura, H., Nagai, S., Yoneyama, H., Onai, N., Ishikawa, S., Kuriyama, T., Matsushima K. 2001. Blockade of secondary lymphoid tissue chemokine exacerbates *Propionibacterium acnes*-induced acute lung inflammation. *J. Immunol.* 166:2071.

Kanwar, J. R., Harrison, J. E., Wang, D., Leung, E., Mueller, W., Wagner, N., and Krissansen, G. W. 2000. Beta7 integrins contribute to demyelinating disease of the central nervous system. *J Neuroimmunol* 103:146-152.

Karpus, W. J., and Ransohoff, R. M. 1998. Chemokine regulation of experimental autoimmune encephalomyelitis: temporal and spatial expression patterns govern disease pathogenesis. *Journal of Immunology* 161:2667-2671.

Kawakami, N., Lassmann, S., Li, Z., Odoardi, F., Ritter, T., Ziemssen, T., Klinkert, W. E., Ellwart, J. W., Bradl, M., Krivacic, K., et al. 2004. The Activation Status of Neuroantigen-specific T-cells in the Target Organ Determines the Clinical Outcome of Autoimmune Encephalomyelitis. *J Exp Med* 199:185-197.

Kim, C. H., Rott, L. S., Clark-Lewis, I., Campbell, D. J., Wu, L., and Butcher, E. C. 2001. Subspecialization of CXCR5+ T-cells: B helper activity is focused in a germinal center-localized subset of CXCR5+ T-cells. *Journal of Experimental Medicine* 193:1373-1381.

Korner, H., Riminton, D. S., Strickland, D. H., Lemckert, F. A., Pollard, J. D., and Sedgwick, J. D. 1997. Critical points of tumor necrosis factor action in central nervous system autoimmune inflammation defined by gene targeting. *J. Exp. Med.* 186:1585.

Legler, D. F., Loetscher, M., Roos, R. S., Clark-Lewis, I., Baggiolini, M., and Moser, B B. 1998. B cell attracting chemokine-1, a human CXC chemokine expressed in lymphoid tissues, selectively attracts B lymphocytes via BLR1/CXCR5. *J. Exp. Med.* 187:665.

Luther, S. A., Ansel, K. M., and Cyster, J. G. 2003. Overlapping roles of CXCL13, interleukin 7 receptor alpha, and CCR7 ligands in lymph node development. *Journal of Experimental Medicine* 197:1191-1198.

Luther, S. A., Bidgol, A., Hargreaves, D. C., Schmidt, A., Xu, Y., Paniyadi, J., Matloubian, M., and Cyster, J. G. 2002. Differing activities of homeostatic chemokines CCL19, CCL21, and CXCL12 in lymphocyte and dendritic cell recruitment and lymphoid neogenesis. *Journal of Immunology* 169:424-433.

Luther, S. A., Lopez, T., Bai, W., Hanahan, D., and Cyster, J. G. 2000. BLC expression in pancreatic islets causes B cell recruitment and lymphotoxin-dependent lymphoid neogenesis. *Immunity* 12:471-481.

Luther, S. A., Tang, H. L., Hyman, P. L., Farr, A. G. and Cyster, J. G. 2000. Coexpression of the chemokines ELC and SLC by T zone stromal cells and deletion of the ELC gene in the plt/plt mouse. *PNAS* 97:12694.

Lyons, J. A., Ramsbottom, M. J., and Cross, A. H. 2002. Critical role of antigen-specific antibody in experimental autoimmune encephalomyelitis induced by recombinant myelin oligodendrocyte glycoprotein. *Eur J Immunol.* 32:1905.

Lyons, J. A., San, M., Happ, M. P., and Cross, A. H. 1999. B cells are critical to induction of experimental allergic encephalomyelitis by protein but not by a short encephalitogenic peptide. *European Journal of Immunology* 29:3432-3439.

Magliozzi, R., Columba-Cabezas, S., Serafini, B., and Aloisi, F. 2004. Intracerebral expression of CXCL13 and BAFF is accompanied by formation of lymphoid follicle-like structures in the meninges of mice with relapsing experimental autoimmune encephalomyelitis. *J Neuroimmunol* 148:11-23.

Marusic, S., Miyashiro, J. S., Douhan, J., Konz, R. F., Dejun, X., Pelker, J. W., Ling, V., Leonard, J. P., and Jacobs, K. A. 2002. Local delivery of granulocyte macrophage colony-stimulating factor by retrovirally tansduced antigen-specific T-cells leads to a severe, chronic experimental autoimmune encephalomyelitis in mice. *Neuroscience Letters.* 332:185.

Mazzucchelli, L., Blaser, A., Kappeler, A., Scharli, P., Laissue, J. A., Baggiolini, M., and Uguccioni, M. 1999. BCA-1 is highly expressed in *Helicobacter pylori*-induced mucosa-associated lymphoid tissue and gastric lymphoma. [comment]. *Journal of Clinical Investigation* 104:R49-54.

McQualter, J. L., Rima, D., Ewing, C., Onuki, M., Kay, T. W., Hamilton, J. A., Reid, H. H., and Bernard, C. C. A. 2001. Granulocyte Macrophage Colony-Stimulating Factor: A New Putative Therapeutic Target in Multiple Sclerosis. *J. Exp. Med.* 7:873.

Mori, S., Nakano, H., Aritomi, K., Wand, C-R, Gunn, M. D., and Kakiuchi, T. 2001. Mice lacking expression of the chemokines CCL21-Ser and CCL19 (plt mice) demonstrate delayed but enhanced T-cell immune responses. *J. Exp. Med.* 193: 207.

Moser, B., and Loetscher, P. 2001. Lymphocyte traffic control by chemokines. *Nature Immunology* 2:123-128.

Nakano, H., and Gunn, M. D. 2001. Gene duplications at the chemokine locus on mouse chromosome 4: multiple strain-specific haplotypes and the deletion of secondary lymphoid-organ chemokine and EBI-1 ligand chemokine genes in the plt mutation. *J. Immunol.* 166:361.

Ngo, V. N., Komer, H., Gunn, M. D., Schmidt, K. N. Riminton, D. S., Cooper, M. D., Browning, J. L., Sedgwick, J. D., and Cyster, J. G. 1999. Lymphotoxin α/β and Tumor Necrosis Factor are required for stromal expression of homing chemokines in B and T-cell areas of the spleen. *J. Exp. Med.* 189:403.

Olschwoka, J. A., Bowers, W. J., Hurley, S. D., Mastrangelo, M. A., and Federoff, H. J. 2003. Helper-fress HSV amplicons elicit a markedly less robust innate immune response in the CNS. *Molecular Therapy.* 7: 1-10.

Oppmann, B., Lesley, R., Blom, B., Timans, J. C., Xu, Y., Hunte, B., Vega, F., Yu, N., Wang, J., Singh, K., Zonin, F., Vaisberg, E., Churakova, T., Liu, M., Gorman, D., Wagner, J., Zurawski, S., Liu, Y., Abrams, J. S., Moore, K. W., Rennick, D., de Waal-Malefyt, R., R. Hannum, R., Bazan, J. F. and Kastelein, R. A. 2000. Novel p19 protein engages IL-12p40 to form a cytokine, IL-23, with biological activities similar as well as distinct from IL-12. *Immunity* 13:715.

Pashenkov, M., Soderstrom, M., and Link, H. 2003. Secondary lymphoid organ chemokines are elevated in the cerebrospinal fluid during central nervous system inflammation. *Journal of Neuroimmunology* 135:154-160.

Pashenkov, M., Teleshova, N., and Link, H. 2003. Inflammation in the central nervous system: the role for dendritic cells. *Brain Pathology* 13:23-33.

Paterson, P. Y., and Swanborg, R. H. 1988. Demyelinating diseases of the central and peripheral nervous systems. In: *Immunological Diseases* (ed. Samter, M.) pp. 1877-1916 (Little, Brown and Company, Boston/Toronto).

Prineas, J. W. 1979. Multiple sclerosis: presence of lymphatic capillaries and lymphoid tissue in the brain and spinal cord. *Science* 203:1123-1125.

Prineas, J. W., and Wright, R. G. 1978. Macrophages, lymphocytes, and plasma cells in the perivascular compartment in chronic multiple sclerosis. *Laboratory Investigation* 38:409-421.

Raine, C. S., Barnett, L. B., Brown, A., Behar, T., and McFarlin, D. E. 1980. Neuropathology of experimental allergic encephalomyelitis in inbred strains of mice. *Laboratory Investigation* 43:150-157.

Raine, C. S., Cannella, B., Duijvestijn, A. M., and Cross, A. H. 1990. Homing to central nervous system vasculature by antigen-specific lymphocytes. II. Lymphocyte/endothelial cell adhesion during the initial stages of autoimmune demyelination. *Lab Invest* 63:476-489.

Raine, C. S., Lee, S. C., Scheinberg, L. C., Duijvestin, A. M., and Cross, A. H. 1990. Adhesion molecules on endothelial cells in the central nervous system: an emerging area in the neuroimmunology of multiple sclerosis. *Clinical Immunology & Immunopathology* 57:173-187.

Raine, C. S., Mokhtarian, F., and McFarlin, D. E. 1984. Adoptively transferred chronic relapsing experimental autoimmune encephalomyelitis in the mouse. Neuropathologic analysis. *Laboratory Investigation* 51:534-546.

Salomonsson, S., Larsson, P., Tengner, P., Mellquist, E., Hjelmstrom, P., and Wahren-Herlenius, M. 2002. Expression of the B cell-attracting chemokine CXCL13 in the target organ and autoantibody production in ectopic lymphoid tissue in the chronic inflammatory disease Sjogren's syndrome. *Scandinavian Journal of Immunology* 55:336-342.

Santambrogio, L., Belyanskaya, S. L., Fischer, F. R., Cipriani, B., Brosnan, C. F., Ricciardi-Castagnoli, P., Stem, L. J., Strominger, J. L., and Riese, R. 2001. Developmental plasticity of CNS microglia. *PNAS* 98:6295

Segal, B. M., and Shevach, E. M. 1996. IL-12 unmasks latent autoimmune disease in resistant mice. *J Exp Med* 184:771-775.

Segal, B. M., Chang, J. T., and Shevach, E. M. 2000. CpG oligonucleotides are potent adjuvants for the activation of autoreactive encephalitogenic T-cells in vivo. *J Immunol* 164:5683-5688.

Segal, B. M., Dwyer, B., and Shevach, E. M. 1998. An IL-12/IL-10 Immunoregulatory Circuit Controls Susceptibility to Autoimmune Disease. *J. Exp. Med.* 187: 537.

Sehnaj K, Papierz W, Glabinski A, and Kohno T. 1995. Prevention of chronic relapsing experimental autoimmune encephalomyelitis by soluble tumor necrosis factor receptor I. *Neuroimmunol.* 56(2):135.

Selmaj, K., Raine, C. S., Cannella, B., and Bronsan, C. F. 1991. Identification of lymphotoxin and tumor necrosis factor in multiple sclerosis lesions. *J Clin Invest.* 87:949.

Selmaj, K., Walczak, A., Mycko, M., Berkowicz, T., Kohno, T., and C. S. Raine. 1998. Suppression of experimental autoimmune encephalomyelitis with a TNF binding protein (TNFbp) correlates with downregulation of VCAM-1/VLA-4. *Eur. J. Immunol.* 28: 2035.

Serafini, B., Columba-Cabezas, S., Di Rosa, F., and Aloisi, F. 2000. Intracerebral recruitment and maturation of dendritic cells in the onset and progression of experimental autoimmune encephalomyelitis. *American Journal of Pathology* 157:1991-2002.

Shi, K., Hayashida, K., Kaneko, M., Hashimoto, J., Tomita, T., Lipsky, P. E., Yoshikawa, H., and Ochi, T. 2001. Lymphoid chemokine B cell-attracting chemokine-1 (CXCL13) is expressed in germinal center of ectopic lymphoid follicles within the synovium of chronic arthritis patients. *Journal of Immunology* 166:650-655.

Shu, U., Kiniwa, M., Wu, C. Y., Maliszewski, C., Vezzio, N., Hakimi, J., Gately, M., and Delespesse, G. 1995. Activated T-cells induce interleukin-12 production by monocytes via CD40-C40 ligand interaction. *Eur. J. Immunol.* 25: 1125.

Simpson, J. E., Newcombe, J., Cuzner, M. L., and Woodroofe, M. N. 1998. Expression of monocyte chemoattractant protein-1 and other beta-chemokines by resident glia and inflammatory cells in multiple sclerosis lesions. *J Neuroimmunol.* 84:238.

Skundric, D. S., K. Huston, M. Shaw, H. Y. Tse, and C. S. Raine. 1994. Experimental allergic encephalomyelitis. T-cell trafficking to the central nervous system in a resistant Thy-1 congenic mouse strain. *Lab. Invest.* 71:671.

Skundric, D. S., Kim, C., Tse, H. Y., and Raine, C. S. 1993. Homing of T-cells to the central nervous system throughout the course of relapsing experimental autoimmune encephalomyelitis in Thy-1 congenic mice. *Journal of Neuroimmunology* 46:113-121.

Spahn, T. W., Issazadeh, S., Salvin, A. J., and Weiner, H. L. 1999. Decreased severity of myelin oligodendrocyte glycoprotein peptide 33-35-induced experimental autoimmune encephalomyelitis in mice with a disrupted TCR delta chain gene. *Eur. J. Immunol.* 29: 4060.

Suen, W. E., Bergman, C. M., Hjelmstrom, P., and Ruddle, N. H. 1997. A Critical Role for Lymphotoxin in Experimental Allergic Encephalomyelitis. *J. Exp. Med.* 186:1233.

Suter, T., Malipiero, U., Otten, L., Ludewig, B., Muelethaler-Mottet, A., Mach, B., Reith, W., and Fontana, A. 2000. Dendritic cells and differential usage of the MHC class II transactivator promoters in the central nervous system in experimental autoimmune encephalitis. *Eur. J. Immunol.* 30:794.

Takemura, S., Braun, A., Crowson, C., Kurtin, P. J., Cofield, R. H., O'Fallon, W. M., Goronz, J. J., and C. M. Weyand C M. 2001. Lymphoid neogenesis in rheumatoid synovitis. *J Immunol.* 167:1072.

Theise, N. D., Henegariu, O., Grove, J., Jagirdar, J., Kao, P. N., Crawford, J. M., Badve, S., Saxena, R., and Krause, D. S. 2002. Radiation pneumonitis in mice: a severe injury model for pneumocyte engraftment from bone marrow. *Exp. Hematol.* 30:1333.

Traugott, U., Reinherz, E. L., and Raine, C. S. 1983. Multiple sclerosis. Distribution of T-cells, T-cell subsets and Ia-positive macrophages in lesions of different ages. *Journal of Neuroimmunology* 4:201-221.

Traugott, U., Shevach, E., Chiba, J., Stone, H. J., and Raine, C. S. 1981. Autoimmune encephalomyelitis: simultaneous identification of T and B cells in the target organ. *Science* 214:1251-1253.

Tumanov, A. V., Kuprash, D. V., Lagarkova, M. A., et al. 2002. Distinct role of surface Lymphotoxin expressed by B Cells in the organization of secondary lymphoid tissues. *Immunity* 17: 239.

Ulvestad, E., Williams, K., Bjerkvig, R., Tiekotter, K., Antel, J., and Matre, R. Human microglial cells have phenotypic and functional characteristics in common with both macrophages and dendritic antigen-presenting cells. *J Leukoc Biol.* 1994 December; 56:732-40.

Vanderlugt, C. L., Neville, K. L., Nikcevich, K. M., Eager, T. N., Bluestone, J. A., and Miller, S. D. 2000. Pathologic role and temporal appearance of newly emerging autoepitopes in relapsing experimental autoimmune encephalomyelitis. *J. Immunol.* 164: 670.

Vissers, J. L. M., Hartgers, F. C., Lindhout, E., Figdor, C. G., and Adema, G. J. 2001. BLC (CXCL13) is expressed by different dendritic cell subsets in vitro and in vivo. *Eur. J. Immunol.* 31:1544.

Voskuhl, R. R., Martin, R., Bergman, C., Dalal, M., Ruddle, N. H., and McFarland, H. F. 1993. T helper 1 (Th1) functional phenotype of human myelin basic protein-specific T lymphocytes. *Autoimmunity* 15:137-143.

Wong, R. L., Lingenheld, E. G., Fitzgerald, L., and Clark, R. B. 1989. Murine T-cell helper clones secrete Granulocyte-macrophage stimulating factor (GmCSF) by both interleukin-2-dependent and interleukin-2-independent pathways. *Cell. Immunol.* 123:445.

Yoneyama, H., Matsuno, K., Zhang, Y., Murai, M., Itakura, M., Ishikawa, S., Hasegawa, G., Naito, M., Asakura, H., and Matsushima, K. 2001. Regulation by chemokines of circulating dendritic cell precursors, and the formation of portal tract-associated lymphoid tissue, in a granulomatous liver disease. *J Exp Med* 193:35-49.

What is claimed:

1. A method of treating a subject with multiple sclerosis comprising administering to said subject an effective amount of an antibody that specifically binds CXCL13, wherein said antibody prevents or inhibits the activity of CXCL13.

2. The method of claim 1, wherein said antibody is a monoclonal antibody.

3. A method of reducing exacerbation of multiple sclerosis in a subject comprising administering to said subject an effective amount of an antibody that specifically binds CXCL13, wherein said antibody prevents or inhibits the activity of CXCL13.

4. The method of claim 3, wherein said antibody is a monoclonal antibody.

5. A method of inhibiting progression of multiple sclerosis in a subject comprising administering to said subject an effective amount of an antibody that specifically binds CXCL13, wherein said antibody prevents or inhibits the activity of CXCL13.

6. The method of claim 5, wherein said antibody is a monoclonal antibody.

* * * * *

SEQUENCE LISTING

<160> NUMBER OF SEQ ID NOS: 21

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:/Note=
      Synthetic Construct

<400> SEQUENCE: 1

His Ser Leu Gly Lys Trp Leu Gly His Pro Asp Lys Phe
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:/Note=
      Synthetic Construct

<400> SEQUENCE: 2

Ala Ser Gln Lys Arg Pro Ser Gln Arg His Gly
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence:/Note=
      Synthetic Construct

<400> SEQUENCE: 3

Met Glu Val Gly Trp Tyr Arg Ser Pro Phe Ser Arg Val Val His Leu
1               5                   10                  15

Tyr Arg Asn Gly Lys
            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 4
tgaggctcag cacagcaacg                                              20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 5
cttgagcatt ccctctcagc t                                            21

<210> SEQ ID NO 6
<211> LENGTH: 21
<212> TYPE: DNA

```
<213> ORGANISM: Artificial Sequence
<220> FEATURE:
<223> OTHER INFORMATION: Description of Artificial Sequence:/Note=
      Synthetic Construct

<400> SEQUENCE: 6
ctgcctcaga ttatctgcca t                                                 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 7
gccagagtga ttcacatctc t                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 8
atgaactacc cactaaccct g                                                 21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 9
aggtgaacca ggctctagtt t                                                 21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 10
gtgctggtgg tggctctcct tgtc                                              24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 11
cgtgtcctcg ccgctgttct tc                                                22

<210> SEQ ID NO 12
<211> LENGTH: 24
<212> TYPE: DNA
<213> ORGANISM: Artificial Sequence
```

-continued

```
<220> FEATURE:
<223> OTHER INFORMATION: Description of Artificial Sequence:/Note=
      Synthetic Construct

<400> SEQUENCE: 12
gtgatgccct ggcccggaag attt                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 13
tcggggagac tggggatact gagg                                          24

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 14
gggagcccct tcaagataca agtgacc                                       27

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 15
cggggccagt tccctccaag ac                                            22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 16
gccagggggt ctagaagc                                                 18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 17
tcacttggca cccagtacaa                                               20

<210> SEQ ID NO 18
<211> LENGTH: 20
<212> TYPE: DNA
<213> ORGANISM: Artificial Sequence
<220> FEATURE:
```

```
<223> OTHER INFORMATION: Description of Artificial Sequence:/Note=
      Synthetic Construct

<400> SEQUENCE: 18
caggccaagg tctatgaacg                                                    20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 19
attgtatggc tgcagtgatg tc                                                 22

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 20
gttggataca ggccagactt tgttg                                              25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:/Note=
      Synthetic Construct

<400> SEQUENCE: 21
agggtaggct ggcctatagg ct                                                 22
```